US012076329B2

(12) United States Patent
Isacoff et al.

(10) Patent No.: US 12,076,329 B2
(45) Date of Patent: Sep. 3, 2024

(54) COMPOSITIONS AND METHODS FOR ENHANCING VISUAL FUNCTION

(71) Applicants: The Regents of the University of California, Oakland, CA (US); Max-Planck-Gesellschaft zur Foerderung der Wissenschaften e.V., Munich (DE); Cornell University, Ithaca, NY (US)

(72) Inventors: Ehud Y. Isacoff, Berkeley, CA (US); Johannes Broichhagen, Munich (DE); Joshua T. Levitz, Ithaca, NY (US)

(73) Assignees: Cornell Univerisity, Ithaca, NY (US); MAX-PLANCK-GESELLSCHAFT ZUR FÖRDERUNG DER WISSENSCHAFTEN E.V., Munich (DE); The Regents of the University of California, Oakland, CA (US)

( * ) Notice: Subject to any disclaimer, the term of this patent is extended or adjusted under 35 U.S.C. 154(b) by 191 days.

(21) Appl. No.: 17/332,865

(22) Filed: May 27, 2021

(65) Prior Publication Data

US 2021/0369744 A1 Dec. 2, 2021

Related U.S. Application Data

(60) Provisional application No. 63/032,241, filed on May 29, 2020.

(51) Int. Cl.

| | | |
|---|---|---|
| *A61K 31/655* | (2006.01) | |
| *A61F 9/00* | (2006.01) | |
| *A61K 9/00* | (2006.01) | |
| *A61K 31/52* | (2006.01) | |
| *A61K 35/76* | (2015.01) | |
| *A61K 38/16* | (2006.01) | |
| *A61K 47/40* | (2006.01) | |
| *A61K 47/60* | (2017.01) | |
| *A61K 47/65* | (2017.01) | |
| *A61K 47/68* | (2017.01) | |
| *A61P 27/02* | (2006.01) | |

(52) U.S. Cl.
CPC .......... *A61K 31/655* (2013.01); *A61F 9/0008* (2013.01); *A61K 9/0048* (2013.01); *A61K 31/52* (2013.01); *A61K 35/76* (2013.01); *A61K 38/16* (2013.01); *A61K 47/40* (2013.01); *A61K 47/60* (2017.08); *A61K 47/65* (2017.08); *A61K 47/6849* (2017.08); *A61P 27/02* (2018.01)

(58) Field of Classification Search
CPC ...... A61K 31/655; A61K 47/65; A61K 47/60; A61K 47/6849; A61K 9/0048; A61K 31/52; A61K 35/76; A61K 38/16; A61K 47/40; A61P 27/02; A61F 9/0008
See application file for complete search history.

(56) References Cited

U.S. PATENT DOCUMENTS

| | | | |
|---|---|---|---|
| 9,024,022 B2 | 5/2015 | Bourrier et al. | |
| 2005/0250737 A1* | 11/2005 | Hughes | A61P 27/02 514/171 |
| 2007/0128662 A1* | 6/2007 | Isacoff | G01N 33/53 435/7.1 |
| 2013/0272994 A1* | 10/2013 | Fu | A61K 47/59 424/78.17 |
| 2017/0014528 A1* | 1/2017 | Sengupta | A61K 47/6849 |

FOREIGN PATENT DOCUMENTS

| | | | |
|---|---|---|---|
| WO | WO 2019/060785 | 3/2019 | |
| WO | WO-2019060785 A1 * | 3/2019 | ........... A61K 47/555 |

OTHER PUBLICATIONS

Habrian, et al.; "Conformational pathway provides unique sensitivity to a synaptic mGluR"; Nature Communications; vol. 10, No. 5572, 13 pages (2019).
Nishiyama, et al.; "Virus-Mediated Genome Editing via Homology-Directed Repair in Mitotic and Postmitotic Cells in Mammalian Brain"; Neuron; vol. 96, No. 4, pp. 755-768 (Nov. 15, 2017).
Patel, et al.; "Ocular drug delivery systems: An overview"; World J Pharmacol; vol. 2, No. 2, pp. 47-64 (2013).
Acosta-Ruiz et al., "Branched Photoswitchable Tethered Ligands Enabled Ultra-Efficient Optical Control and Detection of G Protein-Coupled Receptors In Vivo" Neuron 105, Feb. 5, 2020, pp. 446-463.

* cited by examiner

*Primary Examiner* — Michael P Cohen
(74) *Attorney, Agent, or Firm* — Rudy J. Ng; Paula Borden; Bozicevic, Field & Francis LLP

(57) ABSTRACT

The present disclosure provides a conjugate comprising an affinity agent, a branched linker, and two or more photoisomerizable regulators. The present disclosure provides compositions comprising the conjugate, as well as devices comprising the compositions. The present disclosure provides methods for enhancing visual function, the methods comprising administering the conjugate to an individual in need thereof.

30 Claims, 41 Drawing Sheets

Specification includes a Sequence Listing.

BG-COOSu
DIPEA, DMF

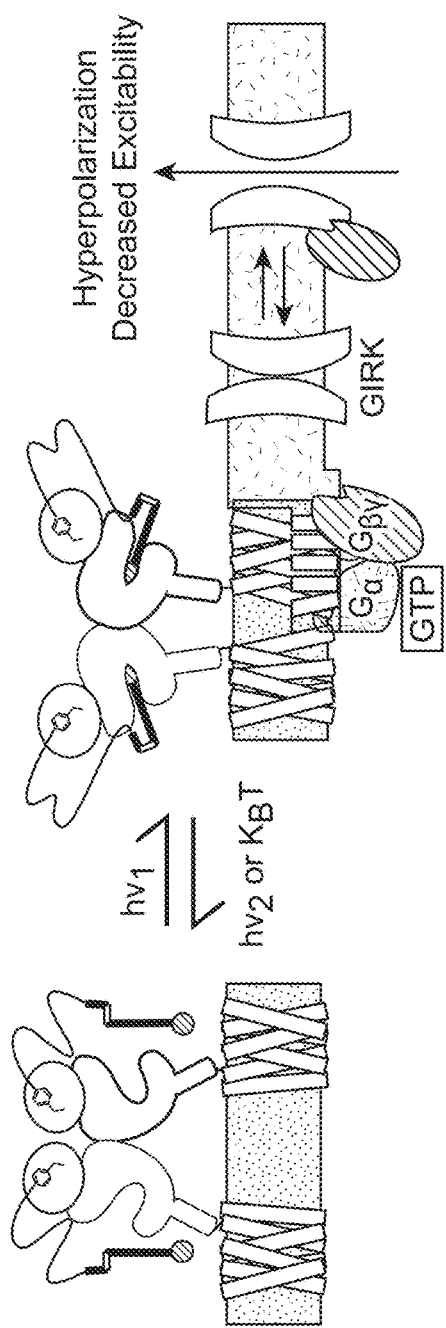
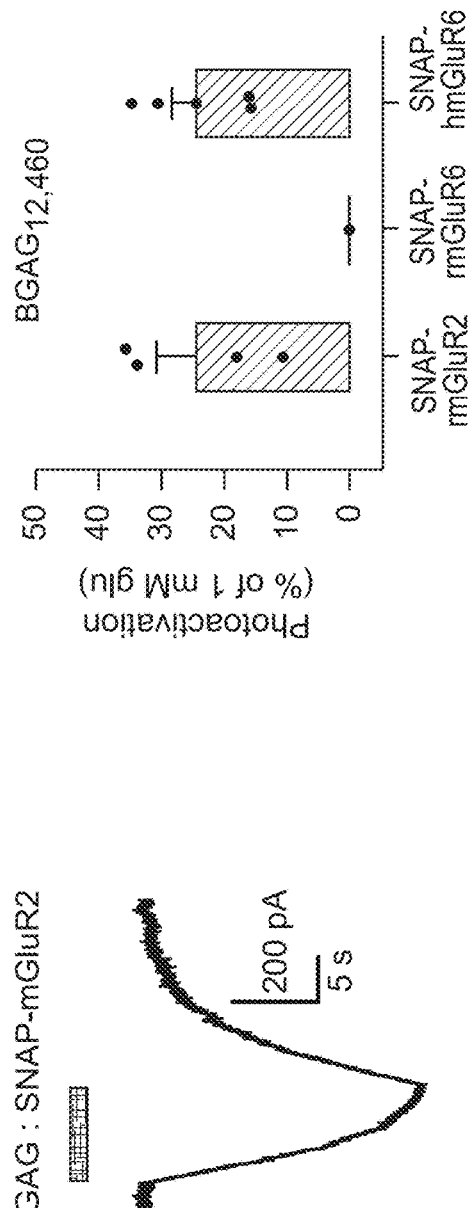
FIG. 3A
FIG. 3B
FIG. 3C

4xBGAG$_{12,460}$

β-CD

←0.70 nm→

Side view $^{4X}BGAG_{12,460}$

SNAP-mGluR2

←0.70 nm→

SEQUENCE LISTING

```
<160> NUMBER OF SEQ ID NOS: 4

<210> SEQ ID NO 1
<211> LENGTH: 182
<212> TYPE: PRT
<213> ORGANISM: Artificial sequence
<220> FEATURE:
<223> OTHER INFORMATION: synthetic sequence

<400> SEQUENCE: 1

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60
```

Trp Leu Asn Ala Tyr Phe His Gln Pro Glu Ala Ile Glu Glu Phe Pro
 65                  70                  75                  80

Val Pro Ala Leu His His Pro Val Phe Gln Gln Glu Ser Phe Thr Arg
                 85                  90                  95

Gln Val Leu Trp Lys Leu Leu Lys Val Val Lys Phe Gly Glu Val Ile
                100                 105                 110

Ser Tyr Ser His Leu Ala Ala Leu Ala Gly Asn Pro Ala Ala Thr Ala
            115                 120                 125

Ala Val Lys Thr Ala Leu Ser Gly Asn Pro Val Pro Ile Leu Ile Pro
        130                 135                 140

Cys His Arg Val Val Gln Gly Asp Leu Asp Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 2
<211> LENGTH: 182
<212> TYPE: PRT
<213> ORGANISM: Artificial sequence
<220> FEATURE:
<223> OTHER INFORMATION: synthetic sequence

<400> SEQUENCE: 2

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Ile Gln Ala Thr Ala
    50                  55                  60

Trp Leu Asn Ala Tyr Phe His Gln Pro Glu Ala Ile Glu Glu Phe Pro
 65                  70                  75                  80

Val Pro Ala Leu His His Pro Val Phe Gln Gln Glu Ser Phe Thr Arg
                 85                  90                  95

Gln Val Leu Trp Lys Leu Leu Lys Val Val Lys Phe Gly Glu Val Ile
                100                 105                 110

Ser Glu Ser His Leu Ala Ala Leu Val Gly Asn Pro Ala Ala Thr Ala
            115                 120                 125

Ala Val Asn Thr Ala Leu Asp Gly Asn Pro Val Pro Ile Leu Ile Pro
        130                 135                 140

Cys His Arg Val Val Gln Gly Asp Ser Asp Val Gly Pro Tyr Leu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 3
<211> LENGTH: 297
<212> TYPE: PRT
<213> ORGANISM: Artificial sequence
<220> FEATURE:
<223> OTHER INFORMATION: synthetic sequence

<400> SEQUENCE: 3

```
Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
                20                  25                  30

Thr Pro Val Leu Phe Leu His Gly Asn Pro Thr Ser Ser Tyr Val Trp
            35                  40                  45

Arg Asn Ile Ile Pro His Val Ala Pro Thr His Arg Cys Ile Ala Pro
        50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
                180                 185                 190

Phe Leu Asn Pro Val Asp Arg Glu Pro Leu Trp Arg Phe Pro Asn Glu
            195                 200                 205

Leu Pro Ile Ala Gly Glu Pro Ala Asn Ile Val Ala Leu Val Glu Glu
210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
                260                 265                 270

Leu Leu Gln Glu Asp Asn Pro Asp Leu Ile Gly Ser Glu Ile Ala Arg
                275                 280                 285

Trp Leu Ser Thr Leu Glu Ile Ser Gly
                290                 295

<210> SEQ ID NO 4
<211> LENGTH: 181
<212> TYPE: PRT
<213> ORGANISM: Artificial sequence
<220> FEATURE:
<223> OTHER INFORMATION: synthetic sequence

<400> SEQUENCE: 4

Asp Lys Asp Cys Glu Met Lys Arg Thr Thr Leu Asp Ser Pro Leu Gly
1               5                   10                  15

Lys Leu Glu Leu Ser Gly Cys Glu Gln Gly Leu His Glu Ile Lys Leu
                20                  25                  30

Leu Gly Lys Gly Thr Ser Ala Ala Asp Ala Val Glu Val Pro Ala Pro
            35                  40                  45
```

-continued

```
Ala Ala Val Leu Gly Gly Pro Glu Pro Leu Met Gln Ala Thr Ala Trp
    50              55                  60

Leu Asn Ala Tyr Phe His Gln Pro Glu Ala Ile Glu Glu Phe Pro Val
65              70                  75                  80

Pro Ala Leu His His Pro Val Phe Gln Gln Glu Ser Phe Thr Arg Gln
                85                  90                  95

Val Leu Trp Lys Leu Leu Lys Val Val Lys Phe Gly Glu Val Ile Ser
                100             105                 110

Tyr Gln Gln Leu Ala Ala Leu Ala Gly Asn Pro Ala Ala Thr Ala Ala
            115             120                 125

Val Lys Thr Ala Leu Ser Gly Asn Pro Val Pro Ile Leu Ile Pro Cys
    130             135                 140

His Arg Val Val Ser Ser Ser Gly Ala Val Gly Gly Tyr Glu Gly Gly
145             150                 155                 160

Leu Ala Val Lys Glu Trp Leu Leu Ala His Glu Gly His Arg Leu Gly
                165             170                 175

Lys Pro Gly Leu Gly
            180
```

COMPOSITIONS AND METHODS FOR ENHANCING VISUAL FUNCTION

CROSS-REFERENCE

This application claims the benefit of U.S. Provisional Patent Application No. 63/032,241, filed May 29, 2020, which application is incorporated herein by reference in its entirety.

STATEMENT REGARDING FEDERALLY SPONSORED RESEARCH

This invention was made with government support under EY018241 awarded by the National Institutes of Health. The government has certain rights in the invention.

INTRODUCTION

Retinitis pigmentosa (RP) results in blindness due to degeneration of photoreceptors, but spares other retinal cells, leading to the hope that expression of light-activated signaling proteins in the surviving cells could restore vision. While most efforts have employed light-activated ion channels, light-activated G-protein coupled receptors (GPCRs), such as the opsins of photoreceptor cells, represent an attractive alternative being native to the retina and functioning with high sensitivity, and possibly at low expression, because they activate channels downstream of an amplifying signal cascade. Indeed, recently ectopic expression of rhodopsin or melanopsin was shown to restore light responses under dim light. However, outside of photoreceptor cells, rhodopsin generates slow light responses and melanopsin generates even slower ones. In the case of rhodopsin, the kinetics are already too slow to support patterned vision, even with an immobile visual stimulus.

There is a need in the art for compositions and methods for enhancing visual function.

SUMMARY

The present disclosure provides a conjugate comprising an affinity agent, a branched linker, and two or more photoisomerizable regulators. The present disclosure provides compositions comprising the conjugate, as well as devices comprising the compositions. The present disclosure provides methods for enhancing visual function, the methods comprising administering the conjugate to an individual in need thereof.

BRIEF DESCRIPTION OF THE DRAWINGS

FIG. 3A-3C depict the effect of monovalent $BGAG_{12,460}$ on GIRK photo-currents in HEK293 cells expressing rat SNAP-mGluR2 or human SNAP-mGluR6.

DEFINITIONS

Figure 1A:
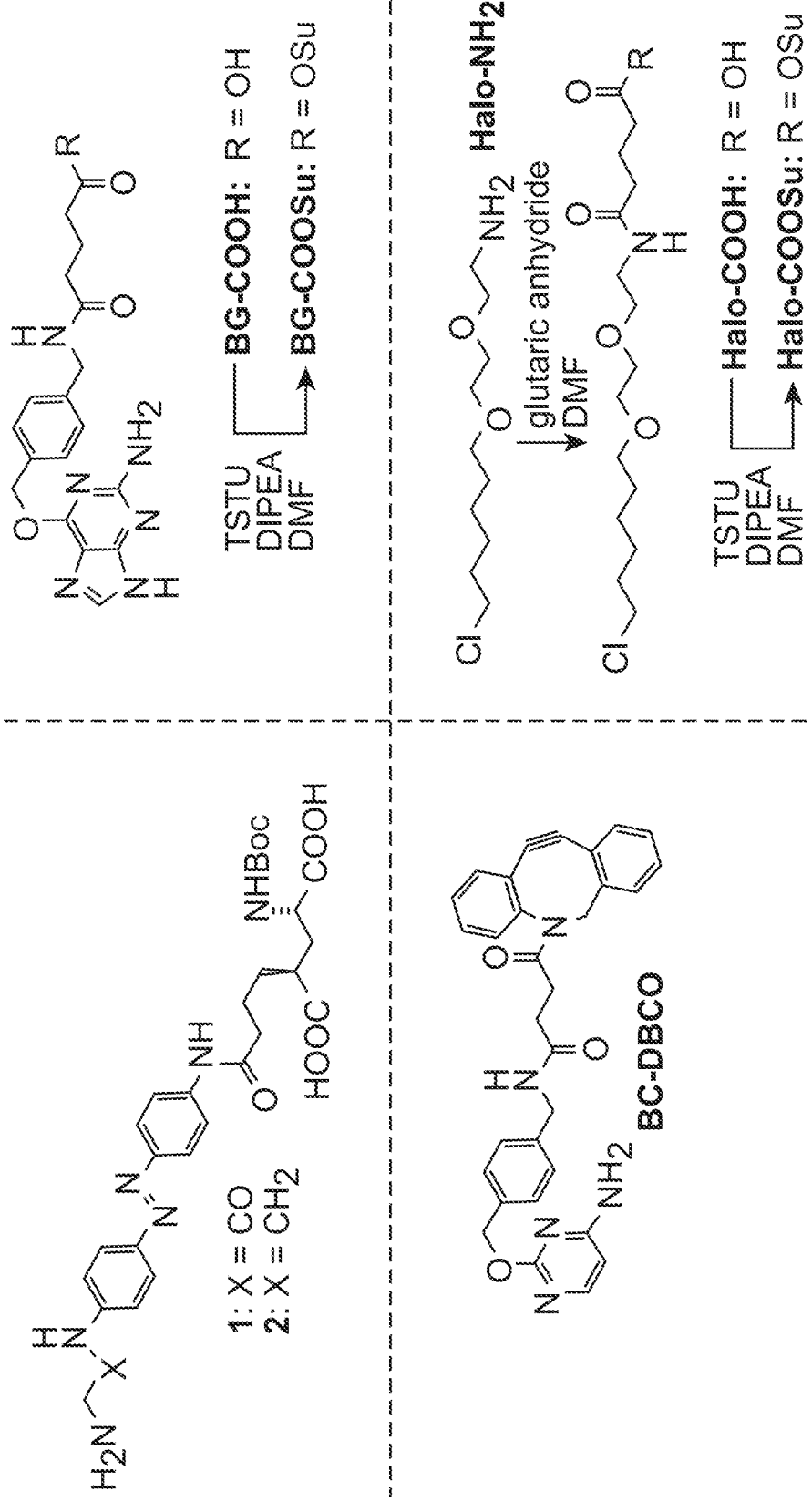
FIG. 1A-1K depict synthetic schemes for embodiments of conjugates of the present disclosure.
Figure 1B:
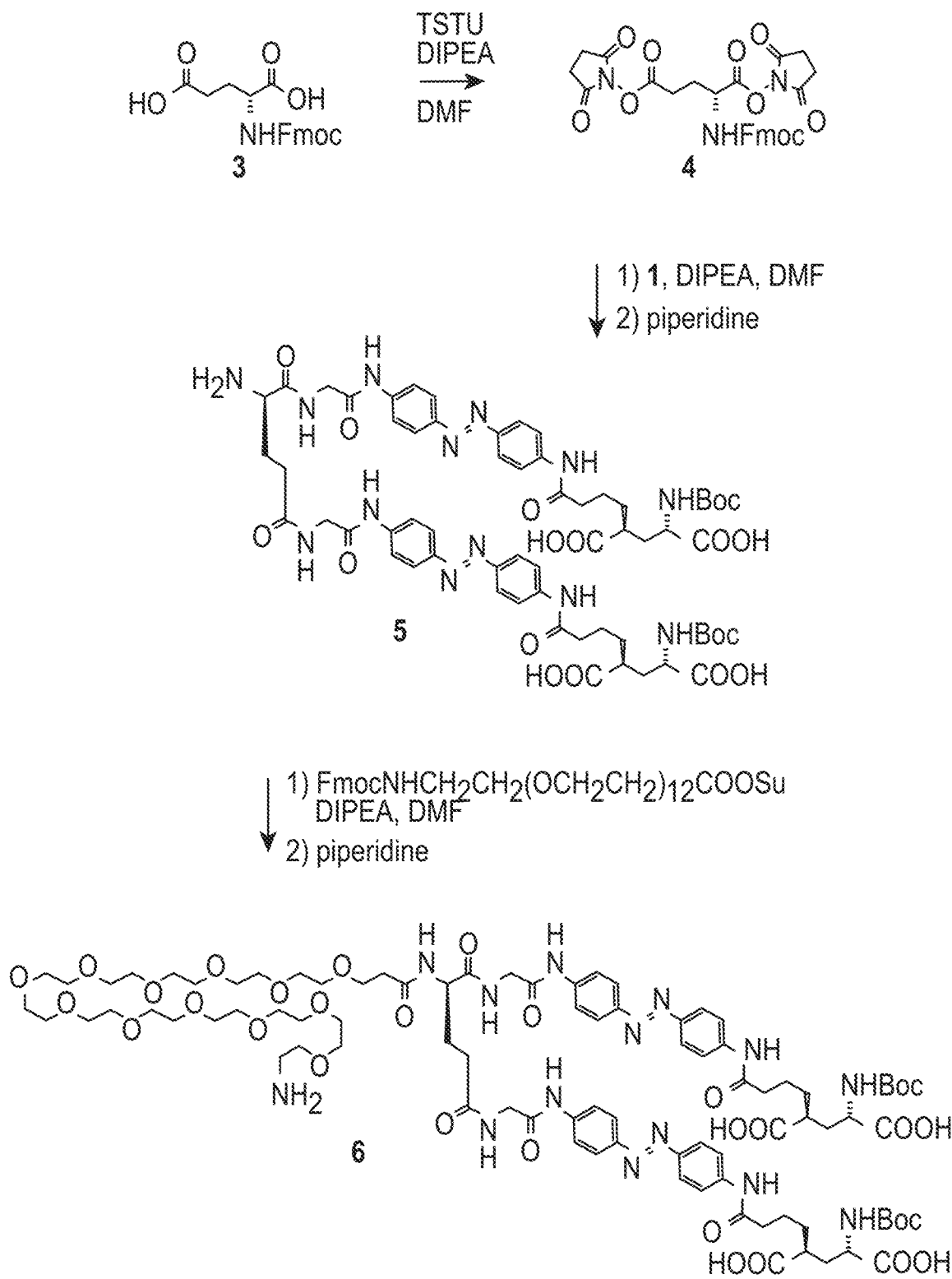
Figure 1B:
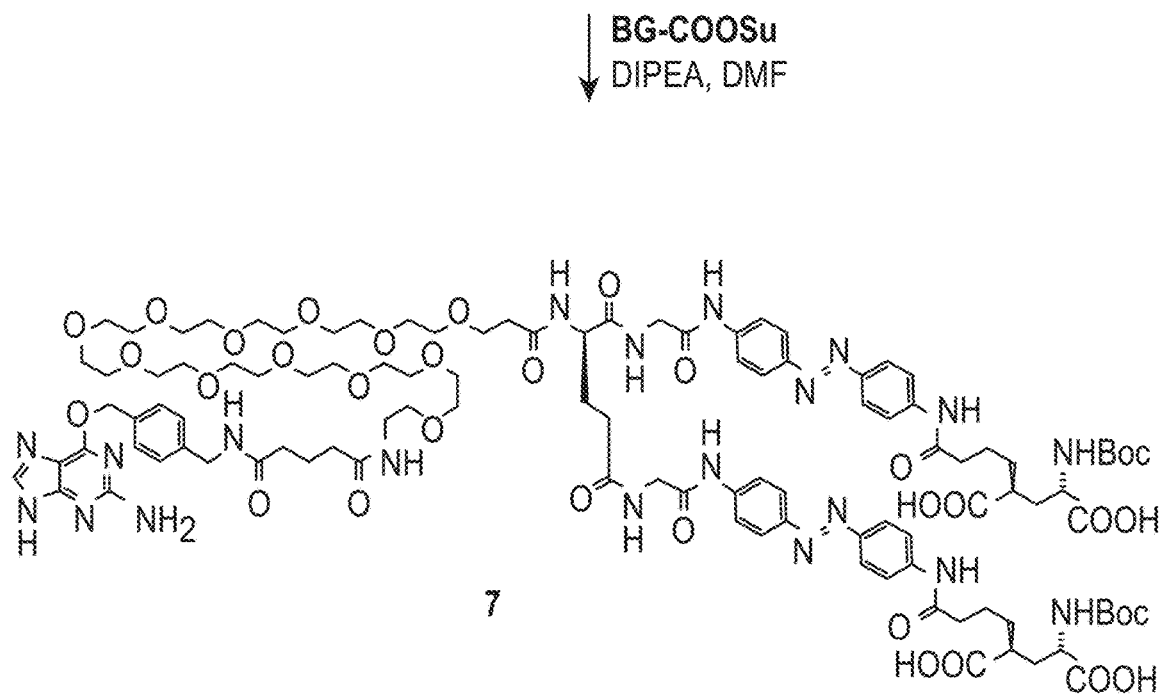
Figure 1B:
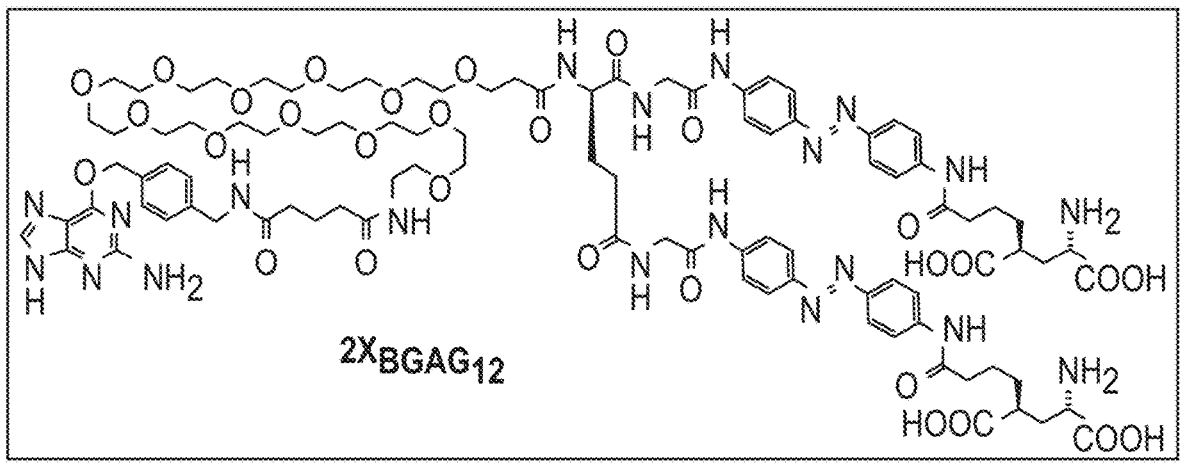
Figure 1C:
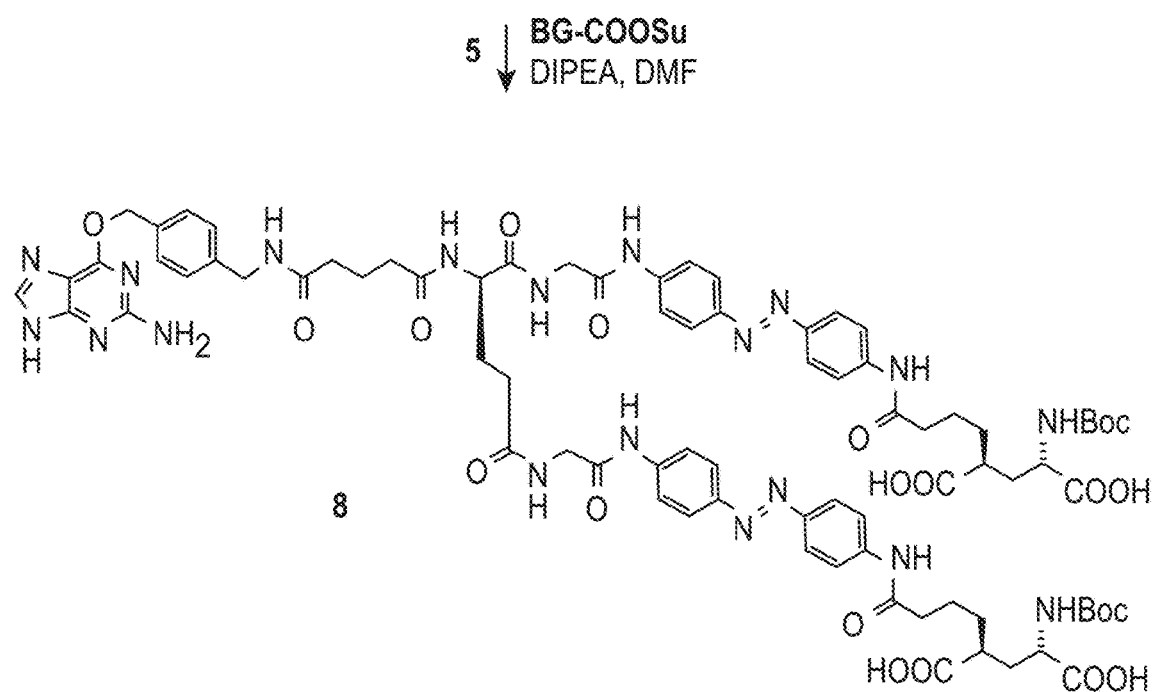
Figure 1C:
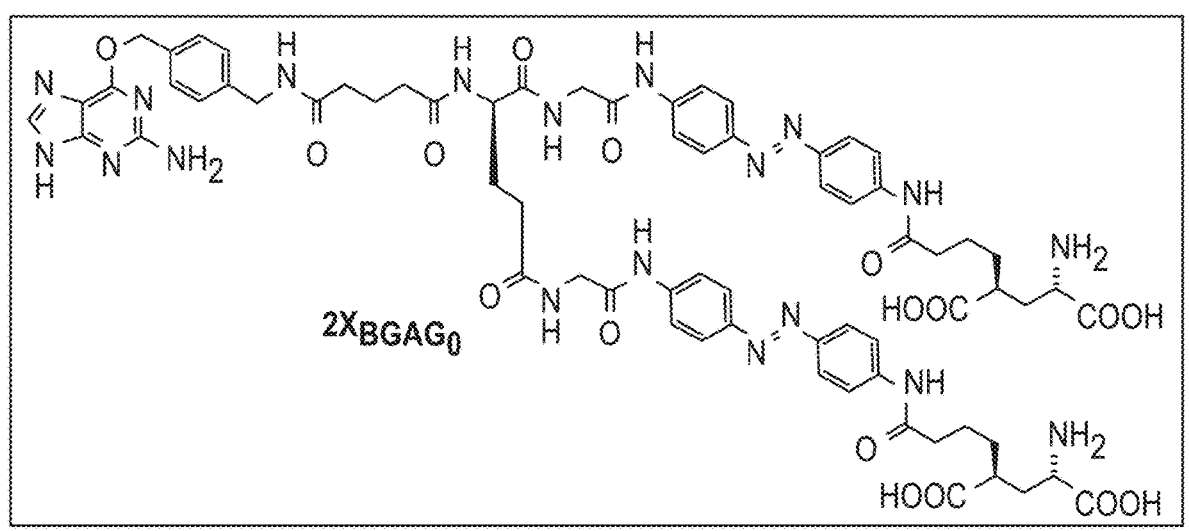
Figure 1D:
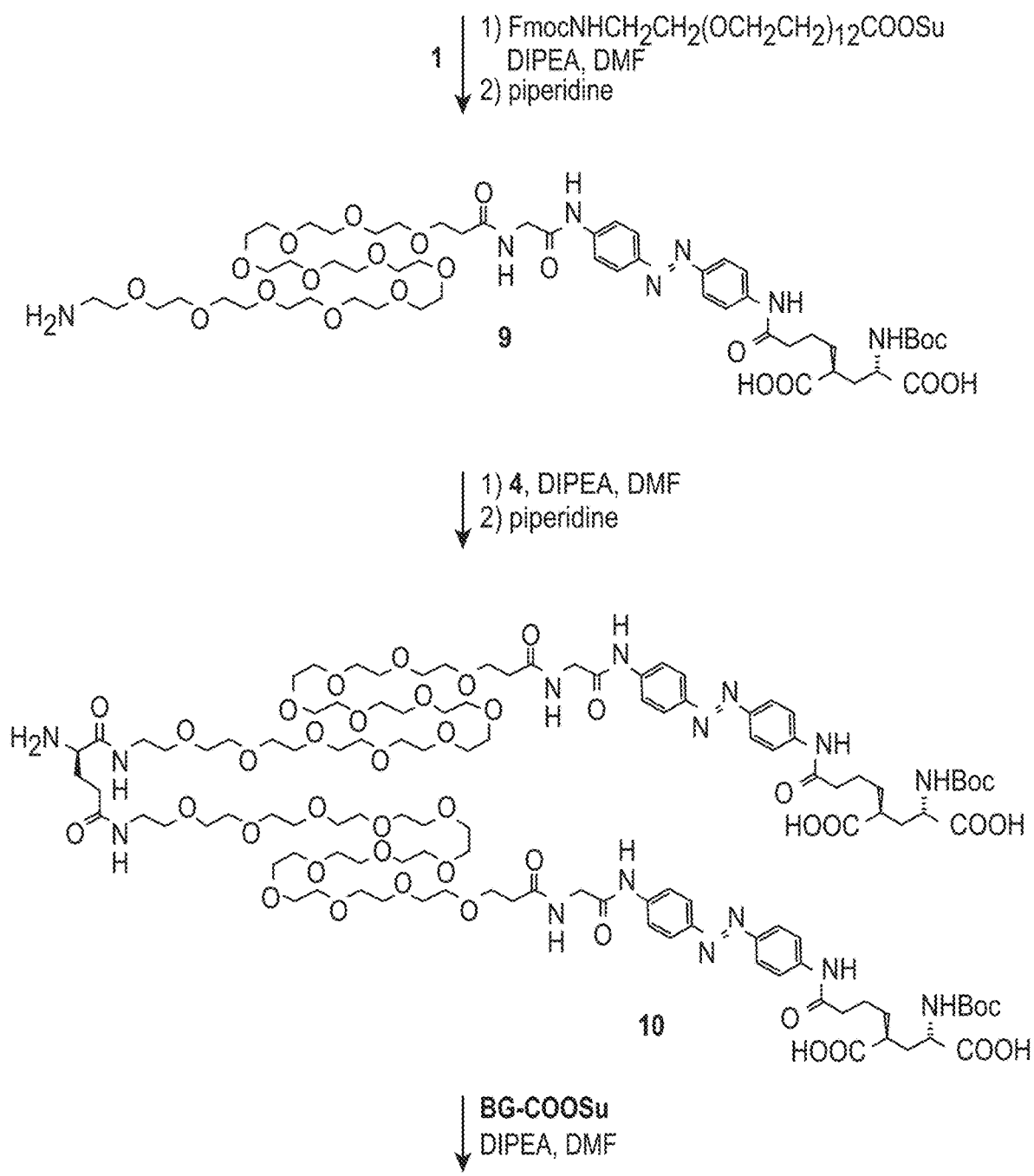
Figure 1D:
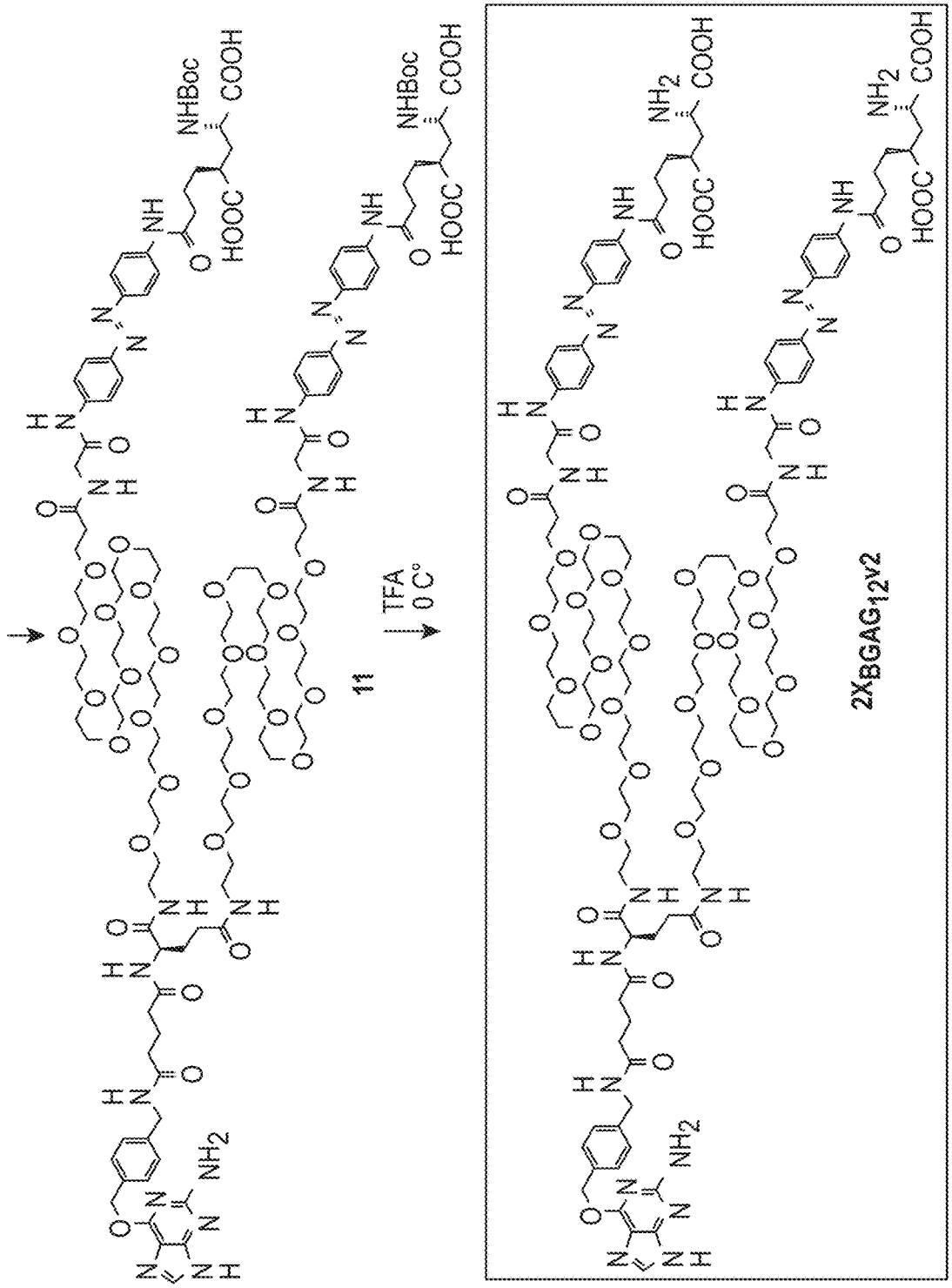
Figure 1E:
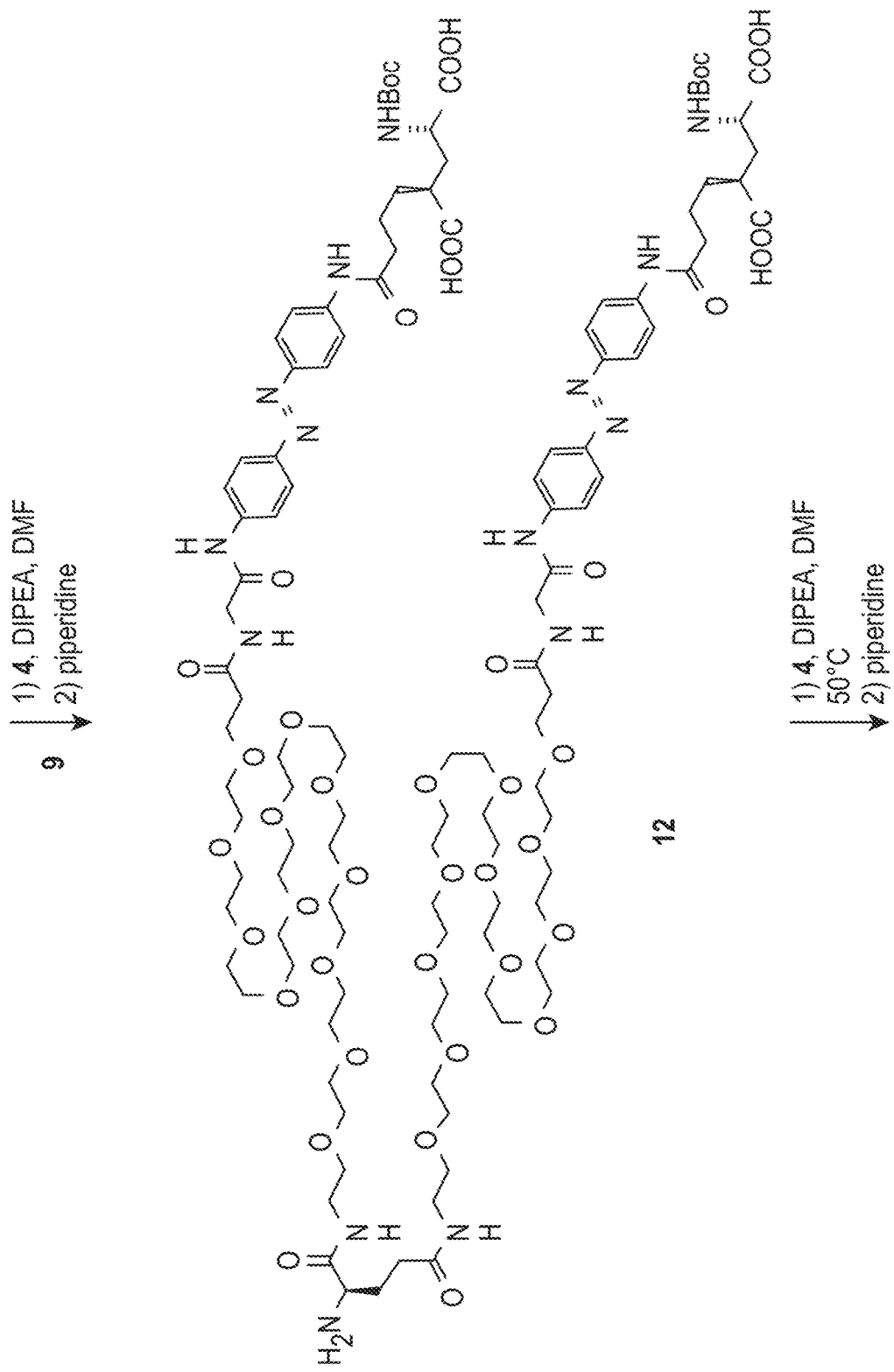
Figure 1E:
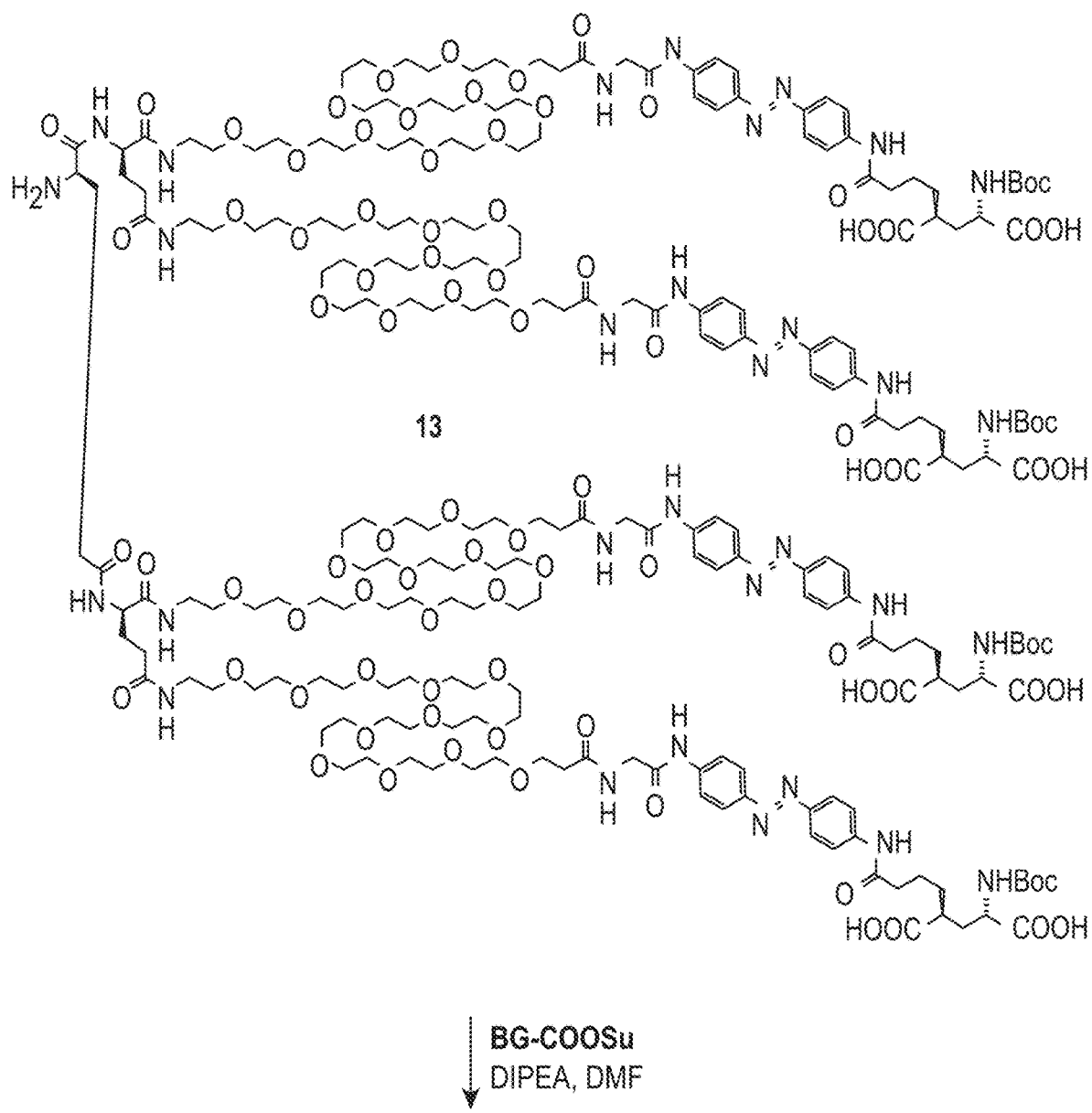
Figure 1E:
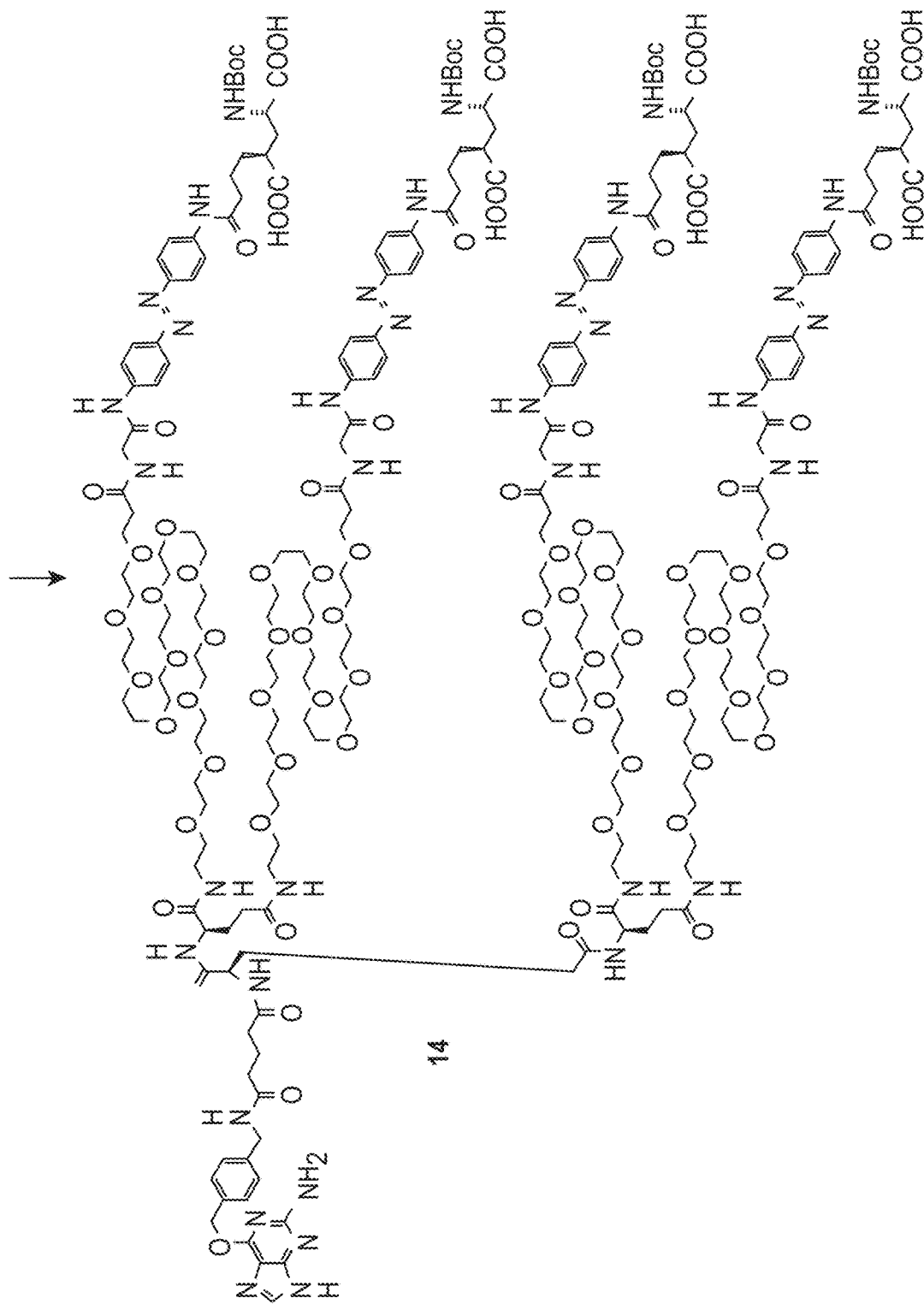
Figure 1E:
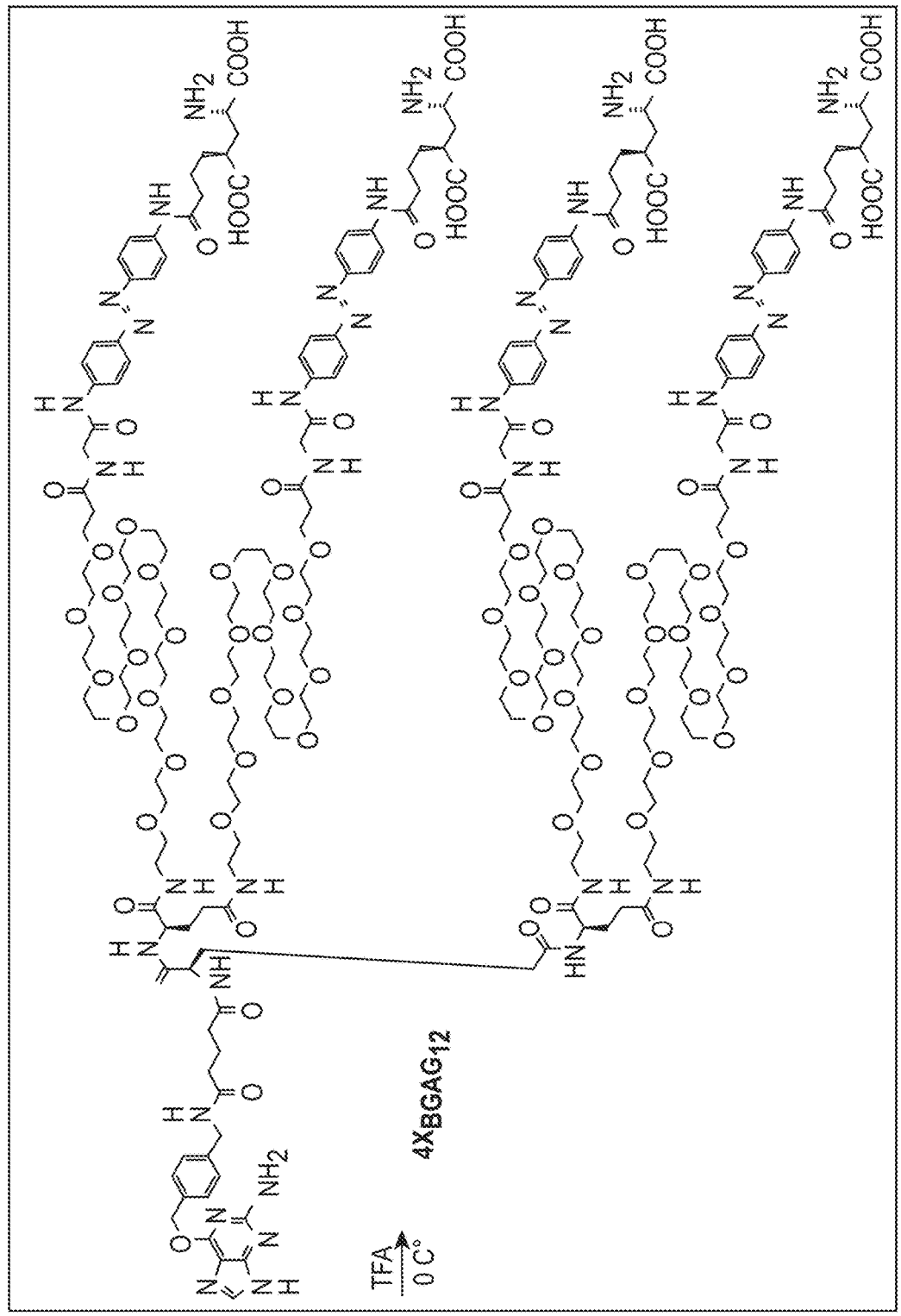
Figure 1F:
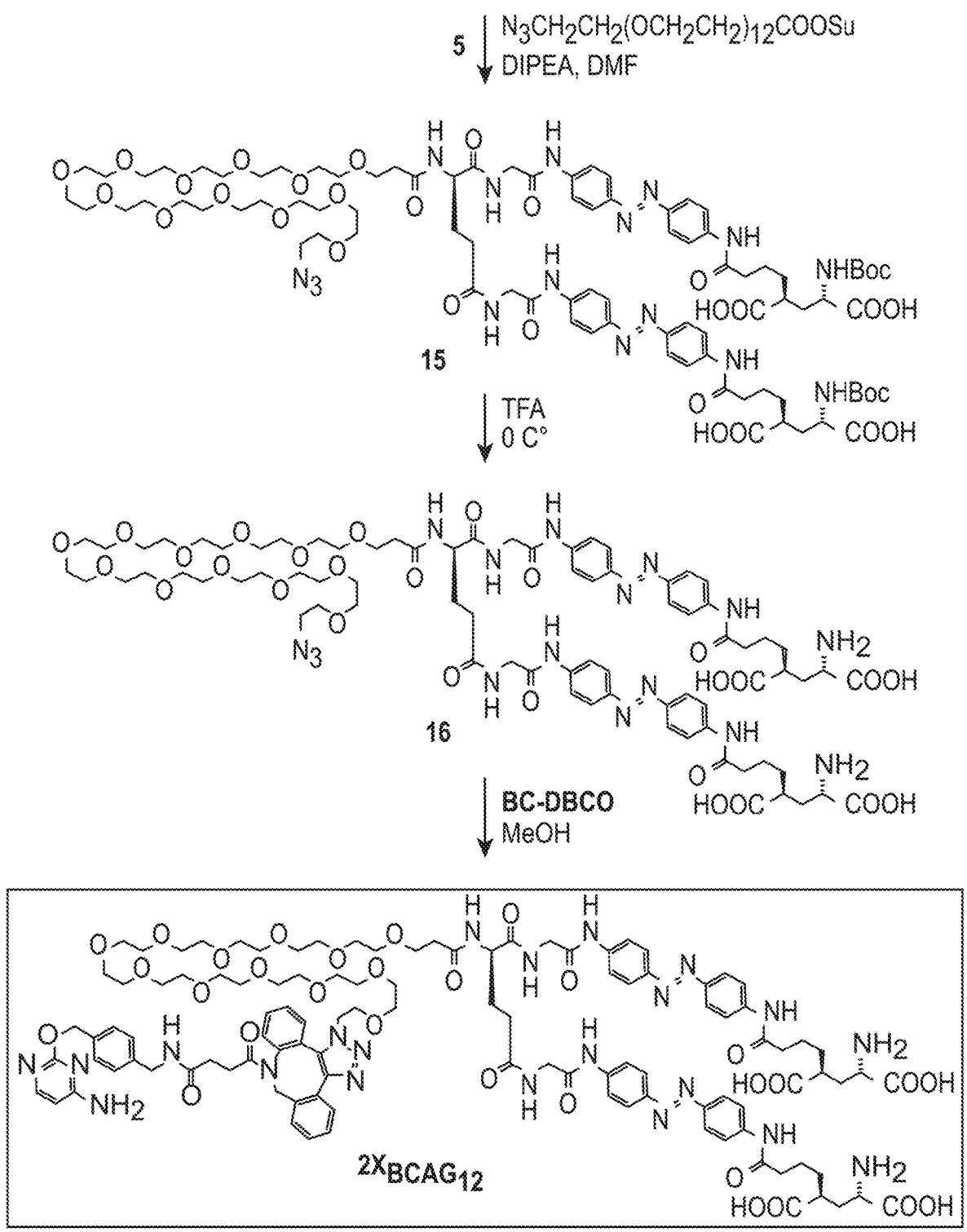
Figure 1G:
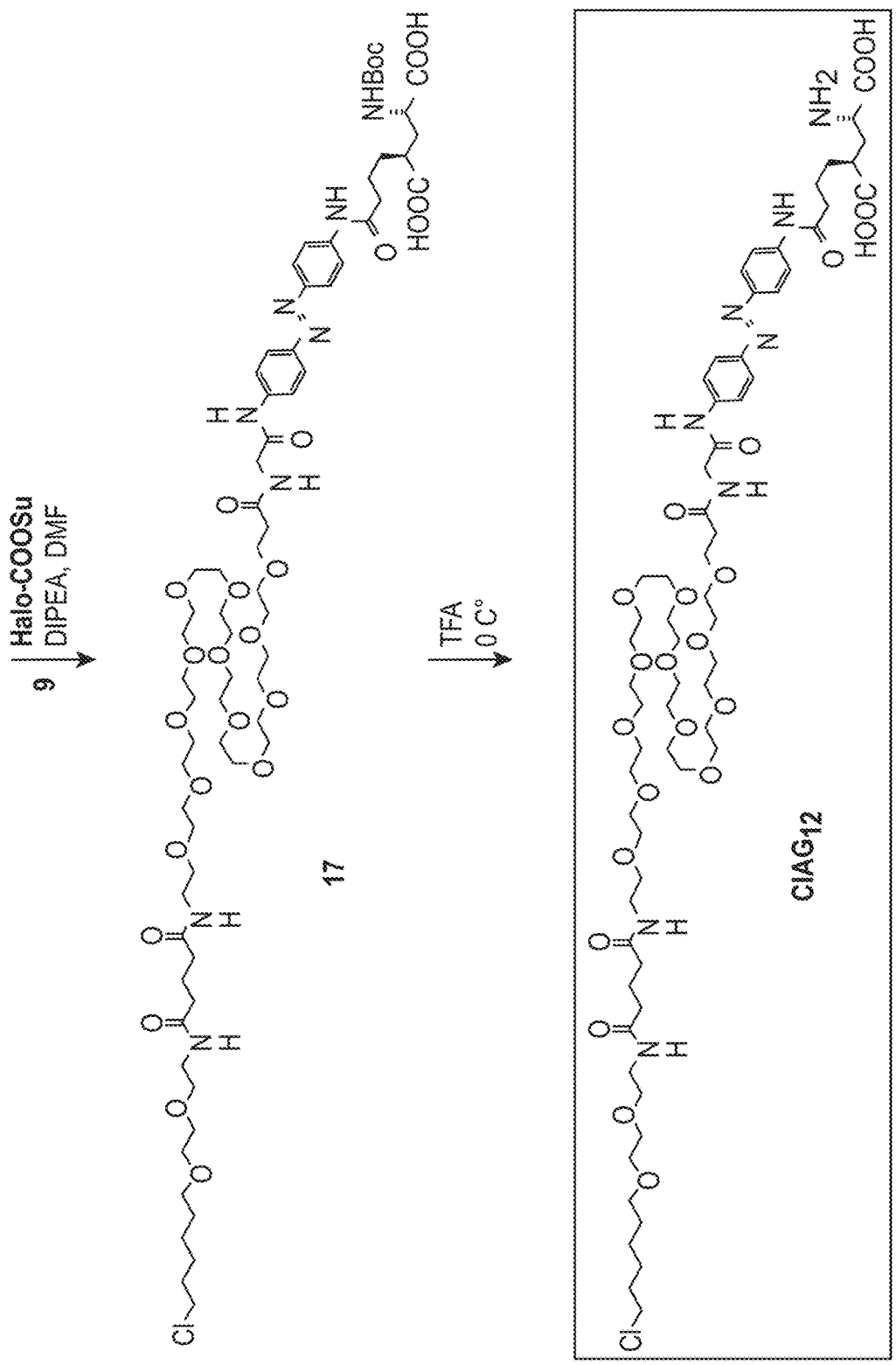

The following terms have the following meanings unless otherwise indicated. Any undefined terms have their art recognized meanings.

The term "alkyl" refers to a monoradical branched or unbranched saturated hydrocarbon chain, e.g., having from 1 to 40 carbon atoms, from 1 to 10 carbon atoms, or from 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above wherein one or more carbon atoms in the alkyl chain have been optionally replaced with a heteroatom such as —O—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$Rb, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "alkylaminoalkyl", "alkylaminoalkenyl" and "alkylaminoalkynyl" refers to the groups R$^a$NHR$^b$— where R$^a$ is alkyl group as defined above and R$^b$ is alkylene, alkenylene or alkynylene group as defined above.

The term "alkaryl" or "aralkyl" refers to the groups -alkylene-aryl and -substituted alkylene-aryl where alkylene, substituted alkylene and aryl are defined herein.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

The term "alkenyl" refers to a monoradical of a branched or unbranched unsaturated hydrocarbon group having from 2 to 40 carbon atoms, from 2 to 10 carbon atoms, or from 2 to 6 carbon atoms and having at least 1 site (e.g., from 1-6 sites) of vinyl unsaturation.

The term "substituted alkenyl" refers to an alkenyl group as defined above having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynyl" refers to a monoradical of an unsaturated hydrocarbon having from 2 to 40 carbon atoms, from 2 to 20 carbon atoms, or from 2 to 6 carbon atoms and having at least 1 site (e.g., from 1-6 sites) of acetylene (triple bond) unsaturation.

The term "substituted alkynyl" refers to an alkynyl group as defined above having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl, and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl, and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl, and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl, and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Exemplary aryls include phenyl, naphthyl and the like. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$— substituted alkyl, —SO$_2$-aryl, —SO$_2$-heteroaryl and trihalomethyl.

The term "aryloxy" refers to the group aryl-O— wherein the aryl group is as defined above including optionally substituted aryl groups as also defined herein.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O— alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl, and the like.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring). Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. Such heteroaralkyl groups are exemplified by pyridylmethyl, pyridylethyl, indolylmethyl, and the like.

The term "heteroaryloxy" refers to the group heteroaryl-O—.

The term "heterocycle" or "heterocyclic" refers to a monoradical saturated or unsaturated group having a single ring or multiple condensed rings, from 1 to 40 carbon atoms and from 1 to 10 hetero atoms, e.g., from 1 to 4 heteroatoms, selected from nitrogen, sulfur, phosphorus, and/or oxygen within the ring. Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

Examples of nitrogen heteroaryls and heterocycles include, but are not limited to, pyrrole, thiophene, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, pyrrolidine, piperidine, piperazine, indoline, morpholine, tetrahydrofuranyl, tetrahydrothiophene, and the like as well as N-alkoxynitrogen containing heterocycles.

The term "heterocyclooxy" refers to the group heterocyclic-O—.

The term "heterocyclothio" refers to the group heterocyclic-S—.

The term "heterocyclene" refers to the diradical group formed from a heterocycle, as defined herein, and is exemplified by the groups 2,6-morpholino, 2,5-morpholino and the like.

The term "heteroarylamino" refers to a 5 membered aromatic ring wherein one or two ring atoms are N, the remaining ring atoms being C. The heteroarylamino ring may be fused to a cycloalkyl, aryl or heteroaryl ring, and it may be optionally substituted with one or more substituents, e.g., one or two substituents, selected from alkyl, substituted alkyl, cycloalkyl, aryl, aralkyl, heteroaryl, heteroaralkyl, halo, cyano, acyl, amino, substituted amino, acylamino, —OR (where R is hydrogen, alkyl, alkenyl, cycloalkyl, acyl, aryl, heteroaryl, aralkyl, or heteroaralkyl), or —S(O)$_n$R where n is an integer from 0 to 2 and R is hydrogen (provided that n is 0), alkyl, alkenyl, cycloalkyl, amino, heterocyclo, aryl, heteroaryl, aralkyl, or heteroaralkyl.

The term "heterocycloamino" refers to a saturated monovalent cyclic group of 4 to 8 ring atoms, wherein at least one ring atom is N and optionally contains one or two additional ring heteroatoms selected from the group consisting of N, O, or S(O)n (where n is an integer from 0 to 2), the remaining ring atoms being C, where one or two C atoms may optionally be replaced by a carbonyl group. The heterocycloamino ring may be fused to a cycloalkyl, aryl or heteroaryl ring, and it may be optionally substituted with one or more substituents, e.g., one or two substituents, selected from alkyl, substituted alkyl, cycloalkyl, aryl, aralkyl, heteroaryl, heteroaralkyl, halo, cyano, acyl, amino, substituted amino, acylamino, —OR (where R is hydrogen, alkyl, alkenyl, cycloalkyl, acyl, aryl, heteroaryl, aralkyl, or heteroaralkyl), or —S(O)$_n$R [where n is an integer from 0 to 2 and R is hydrogen (provided that n is 0), alkyl, alkenyl, cycloalkyl, amino, heterocyclo, aryl, heteroaryl, aralkyl, or heteroaralkyl].

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" or "alkylthio" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of the embodiments include all stereochemical isomers arising from the substitution of these compounds.

The term "pharmaceutically-acceptable salt" refers to salts which retain biological effectiveness and are not biologically or otherwise undesirable. In many cases, the compounds of the embodiments are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component.

A polypeptide has a certain percent "sequence identity" to another polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. The sequence identity can be determined using the default parameters determined by the program. This program is available also from Genetics Computing Group (GCG) package, from Madison, Wisconsin, USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty: 30.0.

The term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. In some cases, the linker backbone includes a linking functional group, such as an ether, thioether, amino, amide, sulfonamide, carbamate, thiocarbamate, urea, thiourea, ester, thioester or imine. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The terms "polyethylene oxide", "PEO", "polyethylene glycol" and "PEG" are used interchangeably and refer to a polymeric group including a chain described by the formula —(CH$_2$—CH$_2$—O—)$_n$— or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15.

The term "retinal cell" can refer herein to any of the cell types that comprise the retina, such as retinal ganglion cells; amacrine cells; horizontal cells; bipolar cells; and photoreceptor cells including rods and cones.

The terms "antibodies" and "immunoglobulin" include antibodies or immunoglobulins of any isotype, fragments of antibodies that retain specific binding to antigen (e.g., to a target ligand-binding polypeptide), including, but not limited to, Fab, Fv, scFv, and Fd fragments, chimeric antibodies, humanized antibodies, single-chain antibodies (scAb), single domain antibodies (sdAb), single domain heavy chain antibodies, a single domain light chain antibodies, nanobodies, bi-specific antibodies, multi-specific antibodies, and fusion proteins comprising an antigen-binding (also referred to herein as antigen binding) portion of an antibody and a non-antibody protein. Also encompassed by the term are Fab', Fv, F(ab')$_2$, and or other antibody fragments that retain specific binding to antigen, and monoclonal antibodies.

The term "nanobody" (Nb), as used herein, refers to the smallest antigen binding fragment or single variable domain (V$_{HH}$) derived from naturally occurring heavy chain antibody and is known to the person skilled in the art. They are derived from heavy chain only antibodies, seen in camelids. In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a V$_{HH}$ antibody.

Cartilaginous fishes also have heavy-chain antibodies (IgNAR; "immunoglobulin new antigen receptor"), from which single-domain antibodies called V$_{NAR}$ fragments can be obtained. Thus, in some cases, an affinity agent is an IgNAR.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al. (1995) *Protein Eng.* 8(10): 1057-1062); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen. Antibody fragments include, e.g., scFv, sdAb, dAb, Fab, Fab', Fab'$_2$, F(ab')$_2$, Fd, Fv, Feb, and SMIP. Examples of sdAb are a camelid VHH and a cartilaginous fish VNAR.

"Fv" is the minimum antibody fragment that contains a complete antigen-recognition and -binding site. This region consists of a dimer of one heavy- and one light-chain variable domain in tight, non-covalent association. It is in this configuration that the three complementarity determining regions (CDRs) of each variable domain interact to define an antigen-binding site on the surface of the V$_H$-V$_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Single-chain Fv" or "sFv" or "scFv" antibody fragments comprise the V$_H$ and V$_L$ domains of antibody, wherein these domains are present in a single polypeptide chain. In some embodiments, the Fv polypeptide further comprises a polypeptide linker between the V$_H$ and V$_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (V$_H$) connected to a light-chain variable domain (V$_L$) in the same polypeptide chain (V$_H$-V$_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad Sci. USA* 90:6444-6448.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; (c) relieving the disease, i.e., causing regression of the disease; and (d) replacing a lost function that results from the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), lagomorphs, etc. In some cases, the individual is a human. In some cases, the individual is a non-human primate. In some cases, the individual is a rodent, e.g., a rat or a mouse. In some cases, the individual is a lagomorph, e.g., a rabbit.

The term "retinal cell" can refer herein to any of the cell types that comprise the retina, such as retinal ganglion cells; amacrine cells; horizontal cells; bipolar cells; photoreceptor cells including rods and cones; Müller glial cells; astrocytes (e.g., a retinal astrocyte); and retinal pigment epithelium.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), AAV type 10 (AAV-10), AAV type 11 (AAV-11), avian AAV, bovine AAV, canine AAV, equine AAV, primate AAV, non-primate AAV, and ovine AAV. See, e.g., Mori et al. (2004) *Virology* 330:375. The term "AAV" also includes chimeric AAV. "Primate AAV" refers to AAV isolated from a primate, "non-primate AAV" refers to AAV isolated from a non-primate mammal, "bovine AAV" refers to AAV isolated from a bovine mammal (e.g., a cow), etc.

An "rAAV vector" as used herein refers to an AAV vector comprising a polynucleotide not of AAV origin (i.e., a polynucleotide heterologous to AAV), e.g., where the heterologous polynucleotide comprises a nucleotide sequence encoding a gene product (a polypeptide or a polynucleotide) of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a conjugate" includes a plurality of such conjugates and reference to "the photoisomerizable moiety" includes reference to one or more photoisomerizable moieties and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a conjugate comprising: i) a target ligand-binding polypeptide; or ii) a polypeptide that binds to a target ligand-binding polypeptide; b) a branched linker; and c) two or more photoisomerizable regulators, wherein each of the two or more photoisomerizable regulators independently comprises: i) a photoisomerizable group; and ii) a ligand that binds to the target ligand-binding polypeptide. The present disclosure provides systems and compositions comprising a conjugate of the present disclosure. The present disclosure provides methods of using a conjugate of the present disclosure to modulate activity of a target polypeptide, and to modulate activity of a target cell or cell population.

Photoswitch Conjugates

The present disclosure provides a conjugate comprising: a) an affinity agent that specifically binds: i) a target ligand-binding polypeptide; or ii) a polypeptide that binds to a target ligand-binding polypeptide; b) a branched linker; and c) two or more photoisomerizable regulators, wherein each of the two or more photoisomerizable regulators independently comprises: i) a photoisomerizable group; and ii) a ligand that binds to the target ligand-binding polypeptide. A conjugate of the present disclosure is also referred to herein as an "affinity-tagged photoswitch." A photoisomerizable regulator is also referred to herein as a "photoswitch."

A conjugate of the present disclosure modulates activity of a target ligand-binding polypeptide. Each of the photoisomerizable regulators in the conjugate can independently interact with the target ligand-binding polypeptide, and the ligand present in each of the photoisomerizable regulators is capable of binding to the ligand-binding site in the target ligand-binding polypeptide in a manner that is controlled by light. Depending on factors such as the ligand, the design of the photoisomerizable regulator, and the wavelength of light, a conjugate of the present disclosure can increase or decrease activity of the target ligand-binding polypeptide, can modulate (increase or decrease) its sensitivity to other stimuli, can stabilize the target ligand-binding polypeptide in a particular conformation, or can induce a conformational change in the target ligand-binding polypeptide.

The affinity agent present in a conjugate of the present disclosure binds to a target ligand-binding polypeptide, and thereby brings the ligands present in the conjugate into proximity with the target ligand-binding polypeptide such that one of the ligands can bind, in a light-dependent manner, to the ligand-binding site in the target ligand-binding polypeptide. When a conjugate of the present disclosure binds to a target ligand-binding polypeptide, the target ligand-binding polypeptide becomes a light-regulated polypeptide.

A change in the wavelength and/or intensity of light ($\Delta\lambda$) to which the light-regulated polypeptide is exposed results in a change in ligand binding to a ligand-binding site of the light-regulated polypeptide, e.g., results in a change in binding of one of the ligand portions of a conjugate of the present disclosure to the ligand-binding site of the light-regulated polypeptide. A "change in the wavelength of light to which the light-regulated polypeptide is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. Repetitive changing from $\lambda_1$ to $\lambda_2$, then from $\lambda_2$ to $\lambda_1$, and back, e.g., switching from a first wavelength to a second wavelength, and back again repeatedly, is also contemplated. Repetitive changing from light to darkness, from darkness to light, etc., is also contemplated.

As indicated above, a conjugate of the present disclosure includes: a) an affinity agent; b) a branched linker; and c) two or more photoisomerizable regulators. In conjugates according to the present disclosure, the branched linker connects the affinity agent to the two or more photoisomerizable regulators. For example, the branched linker can be a linker between the affinity agent and the two or more photoisomerizable regulators, where the branched linker includes two or more arms, such as 3 or more arms, 4 or more arms, 5 or more arms, 6 or more arms, 7 or more arms, 8 or more arms, 9 or more arms, or 10 or more arms. Each arm of the branched linker can be attached to a photoisomerizable regulator. Embodiments of the conjugates of the present disclosure can include two or more photoisomerizable regulators, such as 3 or more, 4 or more, 5 or more, 6 or more, 7 or more, 8 or more, 9 or more, or 10 or more photoisomerizable regulators connected to the affinity agent through the branched linker. As described above, each of the photoisomerizable regulators in the conjugate includes a ligand that binds to the target ligand-binding polypeptide. Correspondingly, conjugates of the present disclosure can include two or more ligands, such as 3 or more, 4 or more, 5 or more, 6 or more, 7 or more, 8 or more, 9 or more, or 10 or more ligands connected to the affinity agent through the branched linker. For example, in some embodiments, a branched linker can include two arms, where each arm is connected to a photoisomerizable regulator. In these embodiments, the affinity agent is connected to each of the two photoisomerizable regulators, and thus connected to each of the two ligands, through separate arms of the branched linker. In other embodiments, a branched linker can include four arms, where each arm is connected to a photoisomerizable regulator. In these embodiments, the affinity agent is connected to each of the four photoisomerizable regulators, and thus connected to each of the four ligands, through separate arms of the branched linker.

In some cases, the change in wavelength (from $\lambda_1$ to $\lambda_2$; from light to darkness; or from darkness to light) results in a change in binding of one of the ligands to a ligand-binding site. As used herein, a "change in binding of a ligand to a ligand-binding site" or "change in binding of one of the ligands to a ligand binding site" includes increased binding and decreased binding. As used herein, "increased binding" includes one or more of: an increased probability of binding of one of the ligands in the photoisomerizable regulators in the conjugate to the ligand-binding site; an increased binding affinity of one or more of the ligands for the ligand-binding site; an increased local concentration of the ligands at the ligand-binding site; and an increased occupancy of one of the ligands in the ligand-binding site. As used herein, "decreased binding" includes one or more of: a decreased probability of binding of one of the ligands in the photoisomerizable regulators in the conjugate to the ligand-binding site; a decreased binding affinity of one or more of the ligands for the ligand-binding site; a decreased local concentration of the ligands at the ligand-binding site; and a decreased occupancy of one of the ligands in the ligand-binding site. As used herein, the term "change in wavelength" to which a conjugate of the present disclosure regulator is exposed, or to which a receptor/synthetic light regulator complex is exposed, refers to a change in wavelength from $\lambda_1$ to $\lambda_{12}$; a change from light to darkness; or a change from darkness to light. An increase in binding includes an increase of from about 10% to about 20%, from about 20% to about 50%, from about 50% to about 2-fold, from about 2-fold to about 5-fold, from about 5-fold to about 10-fold, from about 10-fold to about 50-fold, from about 50-fold to about $10^2$-fold, from about $10^2$-fold to about $10^4$-fold, from about $10^4$-fold to about $10^6$-fold, from about $10^6$-fold to about $10^8$-fold, or a greater than $10^8$-fold increase in binding. A decrease in binding includes a decrease of from about 5% to about 10% to about 20% to about 30%, from about 30% to about 40%, from about 40% to about 50%, from about 50% to about 60%, from about 60% to about 70%, from about 70% to about 80%, from about 80% to about 90%, or from about 90% to 100% decrease in binding.

For example, in some cases, the ligands of the conjugate have a first probability of binding to the ligand binding site at a first wavelength of light; the ligands have a second probability of binding to the ligand binding site at a second wavelength of light; and the second probability is lower than the first probability. In other cases, the ligands of the conjugate have a first probability of binding to the ligand binding site at a first wavelength of light; the ligands have a second probability of binding to the ligand binding site at a second wavelength of light; and the second probability is higher than the first probability. In other cases, the ligands of the conjugate have a first probability of binding to the ligand binding site when exposed to light; the ligands have a second probability of binding to the ligand binding site in the absence of light (e.g., in darkness); and the second probability is lower than the first probability. In other cases, the ligands of the conjugate have a first probability of binding to the ligand binding site when exposed to light; the ligands have a second probability of binding to the ligand binding site in the absence of light and the second probability is higher than the first probability.

In some embodiments, because a conjugate of the present disclosure includes two or more photoisomerizable regulators, and thus includes two or more ligands, the probability of a ligand binding to the ligand site is higher than a conjugate that has only one photoisomerizable regulator, and thus only one ligand. Since the conjugate of the present disclosure includes two or more photoisomerizable regulators, the local concentration of ligands in proximity to the ligand binding site may be higher as compared to a conjugate that has only one photoisomerizable regulator, and thus only one ligand. The increased local concentration of ligands of the conjugates of the present disclosure near the ligand binding site may result in an increase in binding as described above.

The local concentration of the ligands of a conjugate of the present disclosure at the ligand binding site in a light-regulated polypeptide is high. For example, the local concentration of the ligands of a conjugate of the present disclosure at the ligand binding site in a subject light-regulated polypeptide ranges from about 500 nM to about 50 mM, e.g., from about 500 nM to about 10 mM, from about 750 nM to about 1 mM, from about 1 μM to about 750 μM, from about 10 μM to about 500 μM, from about 10 μM to about 250 μM, from about 50 μM to about 200 μM, or from about 50 μM to about 150 μM, such as about 100 μM. In some embodiments, the local concentration of the ligands of a conjugate of the present disclosure at the ligand binding site in a subject light-regulated polypeptide ranges from about 500 nM to about 50 mM, e.g., from about 500 nM to about 750 nM, from about 750 nM to about 1 mM, from about 1 mM to about 5 mM, from about 5 mM to about 10 mM, from about 10 mM to about 20 mM, from about 20 mM to about 30 mM, or from about 30 mM to about 50 mM.

Change in Wavelength Resulting in Binding of a Ligand to the Ligand-Binding Site or Higher Affinity Ligand Binding to Ligand-Binding Site In some cases, a change in the wavelength of light to which a light-regulated polypeptide is exposed results in an increase in binding affinity of one or more of the ligands of a conjugate of the present disclosure for a ligand-binding site the light-regulated polypeptide. For example, in some cases, a change in wavelength of light to which a light-regulated polypeptide is exposed results in an at least about 10%, at least about 20%, at least about 30%, at least about 50%, at least about 75%, at least about 2-fold, at least about 5-fold, at least about 10-fold, at least about 25-fold, at least about 50-fold, at least about 100-fold, at least about 250-fold, at least about 500-fold, at least about $10^3$-fold, at least about $5 \times 10^3$-fold, at least about $10^4$-fold, at least about $5 \times 10^4$-fold, or greater, increase in binding affinity.

Where the ligand is an agonist, the change in wavelength will in some cases result in activation of a light-regulated polypeptide. Where the ligand is an agonist, the change in wavelength will in some cases result in desensitization of a light-regulated polypeptide. Conversely, where the ligand is an antagonist, the change in wavelength will in some cases result in a block of activation of a light-regulated polypeptide, e.g., block of the ability to activate a light-regulated polypeptide with free agonist. Where the ligand is a blocker (e.g., a pore blocker of an ion channel, or an interaction domain that binds to other biological macromolecules such as polypeptides or nucleic acids), the change in wavelength will in some cases result in block of polypeptide activity.

Expressed another way, where the ligand is an agonist, and where a change in the wavelength of light to which a light-regulated polypeptide is exposed results in a higher binding affinity of the ligand moiety of the conjugate to the ligand-binding site of the light-regulated polypeptide, the change in wavelength results in transition from an inactive state to an active state, or to a desensitized state. Where the ligand is an antagonist, the change in wavelength results in transition from a responsive state to an unresponsive state. Where the ligand is a blocker, the change in wavelength results in transition from an active state to an inactive state.

Change in Wavelength Resulting in Removal of a Ligand from Ligand-Binding Site, or Reduced Binding Affinity In some cases, a change in the wavelength of light to which a light-regulated polypeptide is exposed results in removal of a ligand of a conjugate of the present disclosure from a ligand-binding site of the light-regulated polypeptide, e.g., the ligand is not bound to the ligand-binding site. In some cases, a change in the wavelength of light to which the light-regulated polypeptide is exposed results in reduced binding affinity of one or more of the ligands of conjugate of the present disclosure for a ligand-binding site of the light-regulated polypeptide, e.g., the ligand has reduced binding affinity for the ligand-binding site. For example, in some cases, a change in the wavelength of light to which a light-regulated polypeptide is exposed results in a reduction of binding affinity of at least about 10%, at least about 20%, at least about 25%, at least about 30%, at least about 40%, at least about 50%, at least about 60%, at least about 70%, at least about 80%, at least about 90%, at least about 95%, or more.

Where the ligand is an agonist, the change in wavelength will in some cases result in activation of a light-regulated polypeptide. Where the ligand is an agonist, the change in wavelength will in some cases result in deactivation of a light-regulated polypeptide. Where the ligand is an agonist, the change in wavelength will in some cases result in recovery from desensitization of the light-regulated polypeptide. Conversely, where the ligand is an antagonist, the change in wavelength will in some cases result in occupancy of the ligand binding site and a reduction in background activity of the polypeptide, or, alternatively, in loss of activation by physiological stimuli. Where the ligand is an antagonist, the change in wavelength will in some cases result in removal of antagonism to permit activation by physiological stimuli. Where the ligand is a negative allosteric modulator, the change in wavelength that causes binding can result in increased sensitivity to or efficacy of another stimulus. Where the ligand is a positive allosteric modulator, the change in wavelength that causes binding can result in decreased sensitivity to or efficacy of another stimulus. In some cases, the ligand binding site will be a modulatory site where binding by the ligand increases or decreases the sensitivity to or efficacy of another stimulus, so that light regulates this process by controlling the binding of the photoswitched regulator. In some cases, the ligand is a blocker of an active site of the polypeptide (e.g., a pore blocker of an ion channel, or an interaction domain that binds to other biological macromolecules such as polypeptides or nucleic acids, or a blocker of an enzyme active site), and the change in wavelength results in block or relief of block in polypeptide activity to prevent or permit the receptor to function normally.

Expressed another way, where the ligand is an agonist, and where a change in the wavelength of light to which the light-regulated polypeptide is exposed results in removal (or non-binding) of the ligand of conjugate of the present disclosure from the ligand-binding site of the light-regulated polypeptide, the change in wavelength results in transition from a more active state to a less active state, or from a desensitized state to a responsive state. Where the ligand is a negative allosteric modulator, the change in wavelength that causes un-binding results in increased sensitivity to or efficacy of another stimulus. Where the ligand is a positive allosteric modulator, the change in wavelength that causes un-binding results in decreased sensitivity to or efficacy of another stimulus. Where the ligand is an antagonist, the change in wavelength that causes un-binding results in transition from an unresponsive state to a responsive state or from an inactive state to a state with some background "basal" (unliganded) activity. Where the ligand is a blocker, the change in wavelength that causes un-binding results in transition from an inactive state to an active state.

Affinity Agents

The affinity agent present in a conjugate of the present disclosure targets the photoisomerizable regulator to a target ligand-binding polypeptide, by binding directly to the target ligand-binding polypeptide or by binding to a polypeptide that binds to the target ligand-binding polypeptide, or by binding to a fusion partner expressed in fusion with the target ligand binding polypeptide.

In some cases, the affinity agent binds specifically to a target ligand-binding polypeptide. Thus, for example, in some cases, the affinity agent binds to a target ligand-binding polypeptide with an affinity of at least $10^{-6}$ M, at least $10^{-7}$ M, at least $10^{-8}$ M, at least $10^{-9}$ M, or at least $10^{-10}$ M. In some cases, the affinity agent binds directly to the target ligand-binding polypeptide. In some cases, the affinity agent binds to a polypeptide that binds to the target ligand-binding polypeptide.

Suitable affinity agents include, but are not limited to, agents that bind to self-labelling polypeptides; antibodies; aptamers; peptides; and small molecules.

Agents that Bind to Self-Labelling Polypeptides

Suitable affinity agents include nucleoside base derivatives. In some cases, the nucleoside base of the nucleoside base derivative is selected from guanine, cytosine, uracil, thymine, xanthine, and hypoxanthine. For example, the nucleoside base of the nucleoside base derivative can be guanine, xanthine or hypoxanthine. In some cases, the nucleoside base of the nucleoside base derivative is guanine. In other instances, the nucleoside base of the nucleoside base derivative can be cytosine, thymine or uracil. In some cases, the nucleoside base of the nucleoside base derivative is cytosine. The nucleoside base can be derivatized to provide the nucleoside base derivative of the affinity agent of a conjugate of the present disclosure. In some cases, the nucleoside base derivative of the affinity agent is a benzyl-nucleoside base, such as benzylguanine or benzylcytosine. In some cases, the affinity agent is benzylguanine. In embodiments where the affinity agent is benzylguanine, the benzylguanine affinity agent may provide for covalent binding to a SNAP tag. In some cases, the affinity agent is benzylcytosine.

In embodiments where the affinity agent is benzylcytosine, the benzylcytosine affinity agent may provide for covalent binding to a CLIP tag. In some cases, the affinity agent is a chloropyrimidine; a chloropyrimidine can bind to a SNAP tag.

Suitable affinity agents also include alkyl derivatives, such as haloalkyl derivatives where one or more hydrogen atoms in an alkyl or alkyl derivative is replaced by a halogen, e.g., fluoro, chloro, or bromo. In some cases, the haloalkyl derivative is a fluoroalkane. In some cases, the haloalkyl derivative is a chloroalkane. In some cases, the haloalkyl derivative is a bromoalkane. In some cases, the affinity agent is chloroalkane, such as $Cl(CH_2)_6(OCH_2CH_2)_2$. In embodiments where the affinity agent is chloroalkane, the chloroalkane affinity agent may provide for covalent binding to a HALO tag.

Antibodies

In some cases, an affinity agent present in a conjugate of the present disclosure is an antibody. In some cases, an antibody suitable for inclusion in a conjugate of the present disclosure binds to a target ligand-binding polypeptide. Examples of target ligand-binding polypeptides are provided below. An antibody suitable for inclusion in a conjugate of the present disclosure does not inhibit binding of the ligand present in the photoisomerizable regulator to the target ligand-binding polypeptide. Generally, an antibody suitable for inclusion in a conjugate of the present disclosure does not substantially alter activity of the target ligand-binding polypeptide. In some cases, the affinity agent is a single-chain Fv (scFv). In some cases, the affinity agent is a nanobody.

In some cases, the affinity agent is an antibody that binds specifically to a target ligand-binding polypeptide, where the target ligand-binding polypeptide is selected from a transcription regulator, an ion channel, a cation channel, a ligand-gated ion channel, a voltage-gated ion channel, a quorum sensor, a pheromone receptor, a neurotransmitter receptor, a G-protein-coupled receptor, and an enzyme.

In some cases, the affinity agent is an antibody that binds specifically to a target ligand-binding polypeptide, where the target ligand-binding polypeptide is selected from a potassium channel, a sodium channel, or a calcium channel.

In some cases, the affinity agent is an antibody that binds specifically to a target ligand-binding polypeptide, where the target ligand-binding polypeptide is selected from a glutamate receptor, a metabotropic glutamate receptor (mGluR), an ionotropic glutamate receptor (e.g., a kainate receptor; an AMPA receptor; an NMDA receptor), an ionotropic nicotinic acetylcholine receptor, an ionotropic GABA-A receptor, a metabotropic GABA-B receptor, a metabotropic dopamine receptor, an ionotropic purinergic P2X receptor, a metabotropic purinergic P2Y receptor, a metabotropic serotonin receptor, an ionotropic serotonin receptor, an ionotropic glycine receptor, a cation channel, a potassium channel, a calcium channel, a sodium channel, a proton channel, an anion channel, and a chloride channel. In some cases, the affinity agent is an antibody that binds specifically to a metabotropic glutamate receptor, where metabotropic glutamate receptors include, e.g., mGluR2, mGluR3, mGluR5, mGluR6, and the like.

As one non-limiting example, the affinity agent is a scFv that binds specifically to mGluR2. As another non-limiting example, the affinity agent is a nanobody that binds specifically to mGluR2. As another non-limiting example, the affinity agent is a scFv that binds specifically to mGluR3. As another non-limiting example, the affinity agent is a nanobody that binds specifically to mGluR3. As another non-limiting example, the affinity agent is a scFv that binds specifically to mGluR5. As another non-limiting example, the affinity agent is a nanobody that binds specifically to mGluR5. As another non-limiting example, the affinity agent is a scFv that binds specifically to mGluR6. As another non-limiting example, the affinity agent is a nanobody that binds specifically to mGluR6.

Small Molecules

Small molecules that are suitable for use as affinity agent in a conjugate of the present disclosure include small molecules having a molecular weight of less than 2 kDa, less than 1 kDa, less than 500 Daltons, less than 250 Daltons, less than 200 Daltons, less than 100 Daltons, less than 75 Daltons, or less than 50 Daltons. For example, a small molecule that is suitable for use as affinity agent in a conjugate of the present disclosure can have a molecular weight of from 10 Daltons to 2 kDa, e.g., from 10 Daltons to 25 Daltons, from 25 Daltons to 50 Daltons, from 50 Daltons to 100 Daltons, from 100 Daltons to 150 Daltons, from 150 Daltons to 250 Daltons, from 250 Daltons to 500 Daltons, from 500 Daltons to 1 kDa, or from 1 kDa to 2 kDa.

A small molecule that is suitable for use as affinity agent in a conjugate of the present disclosure is generally not a ligand for a target ligand-binding polypeptide. A small molecule that is suitable for use as affinity agent in a conjugate of the present disclosure generally binds to the target ligand-binding polypeptide at a site other than the site at which the ligand binds, and does not substantially inhibit binding of the ligand to the target ligand-binding polypeptide.

Aptamers

Aptamers that are suitable for use as affinity agent include RNA aptamers, DNA aptamers, and peptide aptamers. An aptamer suitable for inclusion in a conjugate of the present disclosure does not inhibit binding of the ligand present in the photoisomerizable regulator to the target ligand-binding polypeptide. Generally, an aptamer suitable for inclusion in a conjugate of the present disclosure does not substantially alter activity of the target ligand-binding polypeptide.

Nucleic acid aptamers can have a length of from about 10 nucleotides to about 200 nucleotides, e.g., from 10 nucleotides (nt) to 15 nt, from 10 nt to 15 nt, from 15 nt to 20 nt, from 20 nt to 25 nt, from 25 nt to 50 nt, from 50 nt to 75 nt, form 75 nt to 100 nt, from 100 nt to 150 nt, or from 150 nt to 200 nt. Nucleic acid aptamers can have a length of from about 10 nucleotides to about 50 nucleotides. Nucleic acid aptamers can have a length of from about 10 nucleotides to about 25 nucleotides.

A DNA aptamer can be prepared using any known method. For example, a DNA-SELEX method can be used. In the SELEX method, by setting strict selection conditions by increasing the number of rounds or using a competing substance, an aptamer exhibiting a stronger binding potential for a target polypeptide is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained. The SELEX method comprises a process of amplification by polymerase chain reaction; by causing a mutation by using manganese ions and the like in the process, it is possible to perform SELEX with higher diversity. Aptamers specific for a polypeptide (or portion of a polypeptide) can be produced using standard techniques, such as, for example, those described in Ogawa, A., et al., Bioorg. Med. Chem, Lett, 14: 4001-4004, 2004; and Jayasena, S. D., Clinical Chemistry 45: 1628-1650, 1999.

A nucleic acid aptamer can include naturally-occurring nucleotides, and may also include non-naturally-occurring nucleotides. DNA aptamers that include only naturally-occurring nucleotides include DNA aptamers composed of deoxyribonucleotides having any of the natural bases adenine, guanine, cytosine, and thymine. RNA aptamers that include only naturally-occurring nucleotides include RNA aptamers composed of RNAs composed of ribonucleotides having any of the natural bases adenine, guanine, cytosine, and uracil. A non-naturally-occurring nucleotide comprises a non-naturally occurring base, a phosphate group, and a sugar. A non-naturally-occurring base (or "artificial base") refers to an artificially constructed base analog having properties similar to those of the natural base constituting the natural nucleotide and that can form artificial base pairing with its partner base analog (referred to as a "complementary artificial base"), as in the natural base. The term "artificial base pairing" refers to base pairing formed between a pair of complementary artificial bases, as in a pair of complementary natural bases adenine and thymine, adenine and uracil, or guanine and cytosine.

Artificial base pairing includes a chemical bond via a hydrogen bond found in the base pairing between natural bases, a physical bond via the molecular structure-based association between artificial bases, and stacking effects via hydrophobic interaction.

Aptamers can be modified to comprise one or more moieties such as: a 2'-O-methyl moiety; a 2'-NH$_2$ moiety; and the like.

Aptamers that bind a variety of polypeptides are known in the art. For example, an aptamer database is available on the internet at www(dot)aptagen(dot)com/aptamer-index/aptamer-list. In addition, as noted above, those skilled in the art can readily design aptamers that bind a target ligand-binding polypeptide of interest.

Branched Linkers

As noted above, a conjugate of the present disclosure includes: a) an affinity agent; b) a branched linker; and c) two or more photoisomerizable regulators. A branched linker is a linker that connects the affinity agent to the two or more photoisomerizable regulators of the conjugate.

As such, the branched linker can be connected to the affinity agent and can include two or more arms, each independently comprising a photoisomerizable regulator. For instance, the branched linker can be connected to the affinity agent at a first end and can include two or more arms at a second end, where each of the two of more arms is independently connected to a photoisomerizable regulator. In some cases, the branched linker includes two or more arms, such as 3 or more arms, 4 or more arms, 5 or more arms, 6 or more arms, 7 or more arms, 8 or more arms, 9 or more arms, or 10 or more arms, where each of the arms is independently connected to a photoisomerizable regulator. Furthermore, as described above, each photoisomerizable regulator of the conjugate of the present disclosure includes a photoisomerizable group. As such, the branched linker can include two or more arms, such as 3 or more arms, 4 or more arms, 5 or more arms, 6 or more arms, 7 or more arms, 8 or more arms, 9 or more arms, or 10 or more arms, where each of the arms is independently connected to a photoisomerizable group. In addition, as described above, each photoisomerizable regulator of the conjugate of the present disclosure includes a ligand that binds to the target ligand-binding polypeptide. As such, the branched linker can include two or more arms, such as 3 or more arms, 4 or more arms, 5 or more arms, 6 or more arms, 7 or more arms, 8 or more arms, 9 or more arms, or 10 or more arms, where each of the arms independently comprises a ligand. In some instances, the branched linker includes two arms. In some cases, the branched linker includes four arms. Moreover, in some cases, a branched linker of a conjugate of the present disclosure will comprise between 4-10 arms, or 4-9 arms, or 4-8 arms, or 4-7 arms, or 4-6 arms, or 4-5 arms, or 5-10 arms, or 5-9 arms, or 5-8 arms, or 5-7 arms, or 5-6 arms, or 6-10 arms, or 6-9 arms, or 6-8 arms, or 6-7 arms, where each of the arms independently comprises a ligand. In other more particular embodiments, a branched linker of a conjugate of the present disclosure will comprise 4 arms, where each of the arms independently comprises a ligand that binds a target ligand-binding polypeptide of interest.

Branched linkers of the conjugates of the present disclosure can be any suitable branched linker that connects the affinity agent to the two or more photoisomerizable regulators. The branched linker may include suitable functional groups that provide for convenient linking chemistry to the affinity agent and respective photoisomerizable regulators. For instance, any type of functional group may be used to connect the branched linker to the affinity agent and/or to the photoisomerizable regulators, such as, but not limited to, amide, ether, amine, ester functional groups, and the like. In some embodiments, amide functional groups provide for convenient linking chemistry between the branched linker and the affinity agent and/or the photoisomerizable regulators.

In some instances, the branched linker comprises a moiety of formula (BL):

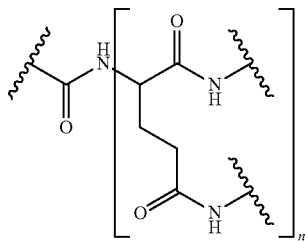

wherein n is an integer from 1 to 10.

In some cases, the affinity agent is attached to the branched linker of formula (BL) on the left side of the moiety, i.e., attached to the amide group on the left side of the moiety at the position indicated by the wavy line. As discussed above, branched linkers of the present disclosure can include two or more arms, where each arm is connected to a separate photoisomerizable regulator. In some cases, n is 1 and the branched linker is attached to 2 photoisomerizable regulators. In some cases, n is 2 and the branched linker is attached to 3 photoisomerizable regulators. In some cases, n is 3 and the branched linker is attached to 4 photoisomerizable regulators. In some cases, n is 4 and the branched linker is attached to 5 photoisomerizable regulators. In some cases, n is 5 and the branched linker is attached to 6 photoisomerizable regulators. In some cases, n is 6 and the branched linker is attached to 7 photoisomerizable regulators. In some cases, n is 7 and the branched linker is attached to 8 photoisomerizable regulators. In some cases, n is 8 and the branched linker is attached to 9 photoisomerizable regulators. In some cases, n is 9 and the branched linker is attached to 10 photoisomerizable regulators. In some cases, n is 10 and the branched linker is attached to 11 photoisomerizable regulators.

For example, in the moiety of formula (BL) where n is 1, the moiety includes one glutaramide group, i.e., the group denoted within the brackets in formula (BL). In this case, when n is 1, two arms are shown on the right side of the moiety, where each arm includes an amide functional group. In the moiety of formula (BL), each of the arms of the glutaramide group includes an amide functional group that can be connected to a photoisomerizable regulator at the respective attachment points indicated by the wavy lines on the right side of the moiety. As such, when n is 1, each arm comprises a photoisomerizable regulator so that the branched linker is attached to two photoisomerizable regulators.

In other embodiments, n can be 3. In this case, the moiety of formula (BL) includes three glutaramide groups, where a second glutaramide group is attached to the upper right side amide functional group of the first glutaramide group of the moiety of formula (BL) at the attachment point indicated by the wavy line, and a third glutaramide group is attached to the lower right side amide functional group of the first glutaramide group of the moiety of formula (BL) at the attachment point indicated by the wavy line. In addition, the second glutaramide group includes two arms, where each arm is attached to a respective photoisomerizable regulator, the third glutaramide group includes two arms, where each arm is attached to a respective photoisomerizable regulator. As such, when n is 3, the branched linker of formula (BL) includes four arms, each comprising a photoisomerizable regulator so that the branched linker is attached to four photoisomerizable regulators.

In other cases, in the moiety of formula (BL), n will be between 1-10, or 1-9, or 1-8, or 1-7, or 1-6, or 1-5, or 1-4. In other cases, in the moiety of formula (BL), n will be between 2-10, or 2-9, or 2-8, or 2-7, or 2-6, or 2-5, or 2-4. In other cases, in the moiety of formula (BL), n will be between 3-10, or 3-9, or 3-8, or 3-7, or 3-6, or 3-5, or 3-4. In other cases, in the moiety of formula (BL), n will be between 4-10, or 4-9, or 4-8, or 4-7, or 4-6, or 4-5. In other cases, in the moiety of formula (BL), n will be between 5-10, or 5-9, or 5-8, or 5-7, or 5-6. In other cases, in the moiety of formula (BL), n will be between 6-10, or 6-9, or 6-8, or 6-7.

Photoisomerizable Regulators

As noted above, a photoisomerizable regulator present in a conjugate of the present disclosure comprises: i) a photoisomerizable group; and ii) a ligand that binds to the target ligand-binding polypeptide.

Photoisomerizable Groups

As noted above, a photoisomerizable regulator present in a conjugate of the present disclosure comprises: i) a photoisomerizable group; and ii) a ligand that binds to the target ligand-binding polypeptide.

Photoisomerizable groups are known in the art, and any known photoisomerizable group can be included in the photoisomerizable regulator present in a conjugate of the present disclosure. Suitable photoisomerizable groups include, but are not limited to, azobenzene, cyclic azobenzenes and azoheteroarenes and derivatives thereof; spiropyran and derivatives thereof; triphenyl methane and derivatives thereof; 4,5-epoxy-2-cyclopentene and derivatives thereof; fulgide and derivatives thereof; thioindigo and derivatives thereof; diarylethene and derivatives thereof; diallylethene and derivatives thereof; overcrowded alkenes and derivatives thereof; and anthracene and derivatives thereof. In some cases, a suitable photoisomerizable group is a photoisomerizable group as shown in the examples herein.

Suitable spiropyran derivatives include, but are not limited to, 1,3,3-trimethylindolinobenzopyrylospiran; 1,3,3-trimethylindolino-6'-nitrobenzopyrylospiran; 1,3,3-trimethylindolino-6'-bromobenzopyrylospiran; 1-n-decyl-3,3-dimethylindolino-6'-nitrobenzopyrylospiran; 1-n-octadecy-1-3,3-dimethylindolino-6'-nitrobenzopyrylospiran; 3',3'-dimethyl-6-nitro-1'-[2-(phenylcarbamoyl)ethyl]spiro; [2H-1-benzopyran-2,2'-indoline]; 1,3,3-trimetnylindolino-8'-methoxybenzopyrylospiran; and 1,3,3-trimethylindolino-(3-naphthopyrylospiran. Also suitable for use is a merocyanine form corresponding to spiropyran or a spiropyran derivative.

Suitable triphenylmethane derivatives include, but are not limited to, malachite green derivatives, specifically, there can be mentioned, for example, bis[dimethylamino)phenyl] phenylmethanol, bis[4-(diethylamino)phenyl]phenylmethanol, bis[4-(dibuthylamino)phenyl]phenylmethanol and bis [4-(diethylamino)phenyl]phenylmethane.

Suitable 4,5-epoxy-2-cyclopentene derivatives include, for example, 2,3-diphenyl-1-indenone oxide and 2',3'-dimethyl-2,3-diphenyl-1-indenone oxide.

Suitable azobenzene compounds include, e.g., compounds having azobenzene residues crosslinked to a side chain, e.g., compounds in which 4-carboxyazobenzene is ester bonded to the hydroxyl group of polyvinyl alcohol or 4-carboxyazobenzene is amide bonded to the amino group of polyallylamine. Also suitable are azobenzene compounds having azobenzene residues in the main chain, for example, those formed by ester bonding bis(4-hydroxyphenyl)dimethylmethane (also referred to as bisphenol A) and 4,4'-dicarboxyazobenzene or by ester bonding ethylene glycol and 4,4'-dicarboxyazobenzene.

Suitable cyclic azobenzene and azoheteroarene compounds which can be adapted for use in the subject conjugates and photoisomerizable regulators include, but are not limited to, 11,12-dihydrodibenzo[c,g][1,2]diazocine-5-oxide,

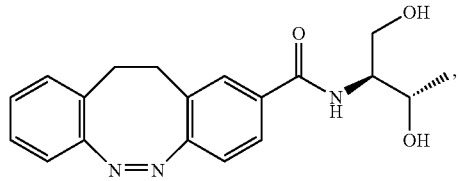 [SMILES: C[C@H](O)[C@H](CO)NC(=O)c1ccc2c(c1)CCc1ccccc1/N=N\2]

heterodiazocines, such as those photoswitches described by Hammerich et al. J. Am. Chem. Soc., 2016, 138 (40), pp 13111-13114), and azoheteroarene photoswitches such as 3-pyrazoles (3pzH or 3pzMe), 5-pyrazoles (5pzH or 5pzMe), 3-pyrrroles (3pyH or 3pyMe), triazole and tetrazoles (tet or 3tri) as describes by Calbo et al. J. Am. Chem. Soc., 2017, 139 (3), pp 1261-1274, the disclosure of which is herein incorporated by reference.

Suitable fulgide derivatives include, but are not limited to, isopropylidene fulgide and adamantylidene fulgide.

Suitable diallylethene derivatives include, for example, 1,2-dicyano-1,2-bis(2,3,5-trimethyl-4-thienyl)ethane; 2,3-bis(2,3,5-trimethyl-4-thiethyl) maleic anhydride; 1,2-dicyano-1,2-bis(2,3,5-trimethyl-4-selenyl)ethane; 2,3-bis(2,3,5-trimethyl-4-selenyl) maleic anhydride; and 1,2-dicyano-1,2-bis(2-methyl-3-N-methylindole)ethane.

Suitable diarylethene derivatives include but are not limited to, substituted perfluorocylopentene-bis-3-thienyls and bis-3-thienylmaleimides.

Suitable overcrowded alkenes include, but are not limited to, cis-2-nitro-7-(dimethylamino)-9-(2',3'-dihydro-1'H-naphtho[2,1-b]thiopyran-1'-ylidene)-9H-thioxanthene and toms-dimethyl-[1-(2-nitro-thioxanthen-9-ylidene)-2,3-dihydro-1H-benzo[f]thiochromen-8-yl]amine. Overcrowded alkenes are described in the literature. See, e.g., terWiel et al. (2005) Org. Biomol. Chem. 3:28-30; and Geertsema et al. (1999) Agnew CHem. Int. Ed. Engl. 38:2738.

Other suitable photoisomerizable groups include, e.g., reactive groups commonly used in affinity labeling, including diazoketones, aryl azides, diazerenes, and benzophenones.

In some instances, the photoisomerizable group of the conjugate (e.g., as defined herein) is an azobenzene (e.g., an azobenzene photoswitch) of the following formula:

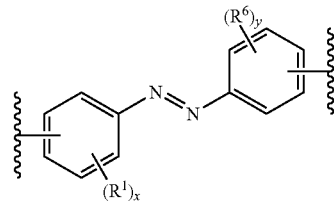

wherein:
R$^1$ and R$^6$ are one or more optional substituents selected from hydrogen, $C_{1-10}$ alkyl, substituted $C_{1-10}$ alkyl, —NR$^{10}$R$^{11}$, —NR$^{12}$C(O)R$^{13}$, —NR$^{12}$C(O)OR$^{13}$, —NR$^{12}$C(O)NR$^{12}$R$^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted C4-10 cycloalkyl, $C_{4-10}$ cycloalkenyl, substituted $C_{4-10}$ cycloalkenyl, cyano, halo, —OR$^{10}$, —C(O)OR$^{10}$, —SR$^{10}$, —S(O)R$^{10}$, —S(O)$_2$R$^{10}$;
x is an integer from 1 to 5;
y is an integer from 1 to 5; and
wherein R$^{10}$-R$^{13}$ are as defined below,
or a pharmaceutically acceptable salt thereof.

In some cases, a photoisomerizable group present in a conjugate of the present disclosure is a compound of Formula 1:

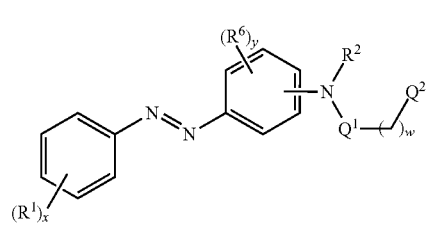

(Formula 1)

wherein:
Q$^1$ is —CH$_2$— or —C(=O)—;
Q$^2$ is a ligand (or a label or reactive group or second affinity agent), as described according to the present disclosure;
each R$^1$ is independently selected from hydrogen, $C_{1-10}$alkyl, substituted $C_{1-10}$alkyl, —NR$^{10}$R$^{11}$, —NR$^{12}$C(O)R$^{13}$, —NR$^{12}$C(O)OR$^{13}$, —NR$^{12}$C(O)NR$^{12}$R$^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted C4-10 cycloalkyl, $C_{4-10}$cycloalkenyl, substituted $C_{4-10}$cycloalkenyl, cyano, halo, —OR$^{10}$, —C(O)OR$^{10}$, —SR$^{10}$, —S(O)R$^{10}$, —S(O)$_2$R$^{10}$;
w is an integer from 1 to 10;
x is an integer from 1 to 5;
y is an integer from 1 to 4;
R$^2$ is selected from hydrogen, $C_{1-10}$alkyl, substituted $C_{1-10}$alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

each $R^6$ is independently selected from hydrogen, $C_{1-10}$ alkyl, substituted $C_{1-10}$ alkyl, $-NR^{10}R^{11}$, $-NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$) cycloalkyl, substituted $C_{4-10}$ cycloalkyl, $C_{4-10}$ cycloalkenyl, substituted $C_{4-10}$ cycloalkenyl, cyano, halo, $-OR^{10}$, $-C(O)OR^{10}$, $-SR^{10}$, $-S(O)R^{10}$, $-S(O)_2R^{10}$;

$R^{10}$ and $R^{11}$ are each independently selected from hydrogen, $C_{1-10}$ alkyl, substituted $C_{1-10}$alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$) cycloalkyl, substituted $C_{4-10}$ cycloalkyl, $C_{4-10}$cycloalkenyl, and substituted $C_{4-10}$ cycloalkenyl;

$R^{12}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl; and $R^{13}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_6$-$C_{10}$ aryl, substituted $C_{6-20}$ aryl, $C_{4-10}$ cycloalkyl, substituted $C_{4-10}$ cycloalkyl, $C_{4-10}$cycloalkenyl, substituted $C_{4-10}$cycloalkenyl, $-CH_2-N(CH_2CH_3)_3{}^+$, and $-CH_2-SO_3{}^-$;

or a pharmaceutically acceptable salt thereof.

In certain embodiments of Formula 1, $Q^1$ is $-CH_2-$. In certain embodiments of Formula 1, $Q^1$ is $-C(=O)-$.

In some instances of Formula 1, one of $R^1$ is linked via a linker to an affinity agent (e.g., as described herein). In some cases, the linker includes a branched linker (e.g., as described herein).

In some cases, a photoisomerizable group present in a conjugate of the present disclosure is a compound of Formula 2:

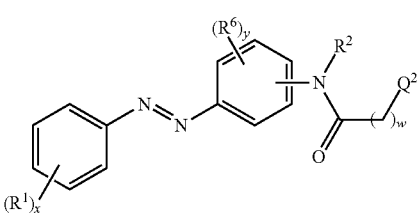

(Formula 2)

wherein
$Q^2$ is a ligand (or a label or reactive group or second affinity agent), as described according to the present disclosure;

each $R^1$ is independently selected from hydrogen, $C_{1-10}$alkyl, substituted $C_{1-10}$alkyl, $-NR^{10}R^{11}$, $-NR^{12}C(O)R^{13}$, $-NR^{12}C(O)OR^{13}$, $-NR^{12}C(O)NR^{12}R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$cycloalkyl, $C_{4-10}$cycloalkenyl, substituted $C_{4-10}$ cycloalkenyl, cyano, halo, $-OR^{10}$, $-C(O)OR^{10}$, $-SR^{10}$, $-S(O)R^{10}$, $-S(O)_2R_{10}$;

w is an integer from 1 to 10;

x is an integer from 1 to 5;

y is an integer from 1 to 4;

$R^2$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

each $R^6$ is independently selected from hydrogen, $C_{1-10}$ alkyl, substituted $C_{1-10}$ alkyl, $-NR^{10}R^{11}$, $-NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $-OR^{10}$, $-C(O)OR^{10}$, $-SR^{10}$, $-S(O)R^{10}$, $-S(O)_2R^{10}$;

$R^{10}$ and $R^{11}$ are each independently selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$cycloalkenyl, and substituted $C_{4-10}$ cycloalkenyl;

$R^{12}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, C6-20 aryl, substituted C6-20 aryl, $C_{4-10}$ cycloalkyl, substituted $C_{4-10}$ cycloalkyl, $C_{4-10}$cycloalkenyl, and substituted $C_{4-10}$ cycloalkenyl; and $R^{13}$ is selected from hydrogen, $C_{1-10}$alkyl, substituted $C_{1-10}$alkyl, $C_{2-10}$ alkenyl, substituted $C_{2-10}$ alkenyl, $C_{2-10}$ alkynyl, substituted $C_{2-10}$ alkynyl, $C_6$-$C_{10}$ aryl, substituted $C_{6-20}$ aryl, $C_{4-10}$cycloalkyl, substituted $C_{4-10}$cycloalkenyl, $C_{4-10}$ cycloalkenyl, substituted $C_{4-10}$ cycloalkenyl, $-CH_2-N(CH_2CH_3)_3{}^{3+}$, and $-CH_2-SO_3{}^-$;

or a pharmaceutically acceptable salt thereof.

In some instances of Formula 2, one of the $R^1$ groups is linked via a linker to an affinity agent (e.g., as described herein). In some cases, the linker includes a branched linker (e.g., as described herein).

In some cases, a photoisomerizable group present in a conjugate of the present disclosure is a compound of Formula 3:

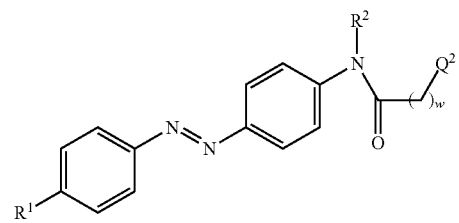

(Formula 3)

wherein:

Q² is a ligand (or a label or reactive group or second affinity agent), as described according to the present disclosure;

w is an integer from 1 to 10;

R¹ is selected from hydrogen, $C_{1-10}$alkyl, —NR$^{10}$R$^{11}$, —NR$^{12}$C(O)R$^{13}$, —NR$^{12}$C(O)OR$^{13}$ and —NR$^{12}$C(O)NR$^{12}$R$^{13}$;

R² is hydrogen or $C_{1-10}$alkyl;

R$^{10}$ and R$^{11}$ are independently selected from hydrogen and $C_{1-10}$alkyl;

R$^{12}$ is hydrogen or $C_{1-10}$alkyl; and

R$^{13}$ is selected from hydrogen, $C_{1-10}$alkyl, $C_{1-8}$ alkenyl, $C_{6-10}$ aryl, and substituted $C_{1-10}$alkyl, or a pharmaceutically acceptable salt thereof.

In certain embodiments of Formula 3, R¹ is $C_{1-10}$alkyl, such as $C_{1-8}$ alkyl, e.g., $C_{1-6}$ alkyl, $C_{1-5}$ alkyl or $C_{1-4}$ alkyl. In some embodiments of Formula 3, R¹ is $C_{1-4}$ alkyl.

In certain embodiments of Formula 3, R¹ is —NR$^{10}$R$^{11}$.

In certain embodiments of Formula 3, R¹ is —NR$^{12}$C(O)R$^{13}$.

In certain embodiment, R² is H.

In some instances of Formula 3, the R¹ group is linked via a linker to an affinity agent (e.g., as described herein). In some cases, the linker includes a branched linker (e.g., as described herein). For example, in embodiments where R¹ is —NR$^{10}$R$^{11}$, the R¹ group can be linked via a linker to an affinity agent through either the R$^{10}$ group or the R$^{11}$ group. In other cases, where R¹ is —NR$^{12}$C(O)R$^{13}$, the R¹ group can be linked via a linker to an affinity agent through the R$^{13}$ group.

In some instances of Formulae 1, 2 or 3, Q² is a ligand, as described according to the present disclosure.

In some instances of Formulae 1, 2 or 3, Q² is a label, as described according to the present disclosure. For example, the label can be a detectable label, such as a fluorophore, as described herein.

In some instances of Formulae 1, 2 or 3, Q² is a reactive group, as described according to the present disclosure.

In some instances of Formulae 1, 2 or 3, Q² is a second affinity agent, as described according to the present disclosure.

In some cases, a photoisomerizable group present in a conjugate of the present disclosure is an azobenzene compound as shown below:

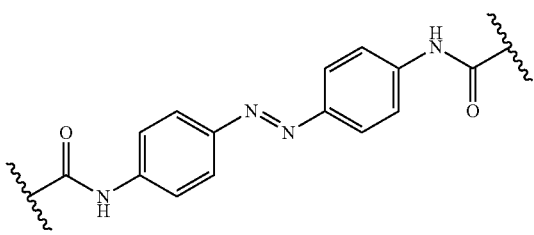

("azobenzene 380)"

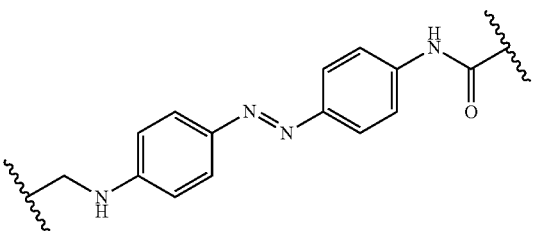

("azobenzene 460)"

where the wavy lines indicate the attachment points to the rest of the conjugate. For instance, the wavy line on the left side of the azobenzene may indicate the attachment point to a linker (e.g., a branched linker as described herein) and the wavy line on the right side of theazobenzene may indicate the attachment point to a ligand as described herein.

In some cases, the photoisomerizable group is an azobenzene, such as an azobenzene photoisomerizable groups are found in WO 2019/060785, the disclosure of which is incorporated herein by reference in its entirety.

Ligands

As noted above, a photoisomerizable regulator present in a conjugate of the present disclosure comprises: i) a photoisomerizable group; and ii) a ligand that binds to the target ligand-binding polypeptide.

As used herein, the term "ligand" refers to a molecule (e.g., a small molecule, a peptide, or a protein) that binds to a polypeptide and effects a change in an activity of the polypeptide, and/or effects a change in conformation of the polypeptide, and/or affects binding of another polypeptide to the polypeptide, or affects the impact of another ligand on the polypeptide.

Ligands include agonists, partial agonists, inverse agonists, antagonists, allosteric modulators, and blockers.

In some cases, the ligand is a naturally-occurring ligand. In other cases, the ligand is a synthetic ligand. In some cases, the ligand is an endogenous ligand. In some cases, the ligand is an agonist. In some cases, the ligand is an inverse agonist. In other cases, the ligand is a partial agonist. In other cases, the ligand is an antagonist. In other cases, the ligand is an allosteric modulator. In other cases, the ligand is a blocker. The term "antagonist" generally refers to an agent that binds to a ligand-binding polypeptide and inhibits the binding of the ligand-binding polypeptide. An "antagonist" may be an agent that binds to or near the orthosteric site (same site where an agonist binds) or an allosteric site but does not activate the ligand-binding polypeptide; instead, the antagonist generally excludes binding by an agonist or hinders activation by the agonist and thus prevents or hinders activation. An "allosteric modulator" may be an agent that binds to an allosteric site away from an orthosteric ligand binding site where binding of an allosteric ligand either decreases the sensitivity to or efficacy of an orthosteric ligand (negative allosteric modulator) or increases the sensitivity to or efficacy of an orthosteric ligand (positive allosteric modulator). The term "blocker" refers to an agent that acts directly on the active site, pore, or allosteric site. Ligands suitable for use herein bind reversibly to a ligand-binding site of a ligand-binding polypeptide.

The ligand is selected based in part on the target ligand-binding polypeptide, and the desired effect on the target ligand-binding polypeptide. For example, a ligand for a hormone-binding transcription factor will in some cases be a hormone, or a synthetic analog of the hormone, or a ligand that interferes with or modulates positively or negatively hormone binding or action. A ligand for a tetracycline transactivator will in some cases be tetracycline or a synthetic analog thereof. A ligand for an enzyme will in some cases be a synthetic agonist or antagonist of the enzyme. In some cases, a ligand will block the ligand-binding site. A ligand for an enzyme or ion channel will in some case be a blocker of the enzyme active site or ion channel pore. A ligand for a ligand-gated ion channel or a G protein coupled receptor or other membrane associated or soluble receptors will in some cases be a naturally-occurring ligand, or a synthetic version of the ligand, e.g., a synthetic analog of the ligand, or a ligand that interferes with or modulates positively or negatively the binding or action of that ligand.

In some cases, a ligand is a small molecule ligand. Small molecule ligands can have a molecular weight in a range of from about 50 daltons to about 3000 daltons, e.g., from about 50 daltons to about 75 daltons, from about 75 daltons to about 100 daltons, from about 100 daltons to about 250 daltons, from about 250 daltons to about 500 daltons, from about 500 daltons to about 750 daltons, from about 750 daltons to about 1000 daltons, from about 1000 daltons to about 1250 daltons, from about 1250 daltons to about 1500 daltons, from about 1500 daltons to about 2000 daltons, from about 2000 daltons to about 2500 daltons, or from about 2500 daltons to about 3000 daltons.

In other cases, a ligand is a peptide ligand. Peptide ligands can have a molecular weight in a range of from about 1 kDa to about 20 kDa, e.g., from about 1 kDa to about 2 kDa, from about 2 kDa to about 5 kDa, from about 5 kDa to about 7 kDa, from about 7 kDa to about 10 kDa, from about 10 kDa to about 12 kDa, from about 12 kDa to about 15 kDa, or from about 15 kDa to about 20 kDa. Peptide ligands can have a length of from 2 amino acids to 20 amino acids, e.g., a peptide ligand can have a length of 2, 3, 4, 5, 6, 7, 8, 9, 10, 11, 12, 13, 14, 15, 16, 17, 18, 19, or 20 amino acids. Peptide ligands can have a length of from 2 amino acids to 5 amino acids, from 5 amino acids to 10 amino acids, from 10 amino acids to 15 amino acids, or from 15 amino acids to 20 amino acids. Peptide ligands can be longer than 20 amino acids, e.g., up to 200 amino acids.

Suitable ligands include, but are not limited to, ligands that block or activate the function of a ligand-binding protein, where ligand-binding proteins include ion and macromolecule permeant channels; receptors (including, but not limited to, ionotropic receptors that bind transmitters; ionotropic receptors that bind hormones; metabotropic receptors and other G protein coupled receptors (including but not limited to mGluR receptors, such as mGluR2, mGluR3, mGluR5 and mGluR6); receptor tyrosine kinases; growth factor receptors; and other membrane receptors that signal by binding to soluble or membrane-bound or extracellular small molecules or proteins); transporters (including but not limited to ion transporters, organic molecule transporters, peptide transporters, and protein transporters); enzymes (including but not limited to kinases; phosphatases; ubiquitin ligases; acetylases; oxo-reductases; lipases; enzymes that add lipid moieties to proteins or remove them; proteases; and enzymes that modify nucleic acids, including but not limited to ligases, helicases, topoisomerases, and telomerases); motor proteins (including kinesins, dyenins and other microtubule-based motors, myosins and other actin-based motors, DNA and RNA polymerases and other motors that track along polynucleotides); scaffolding proteins; adaptor proteins; cytoskeletal proteins; and other proteins that localize or organize protein domains and superstructures within cells.

Suitable ligands include, but are not limited to, ligands that function as general anesthetics; ligands that function as local anesthetics; ligands that function as analgesics; synthetic and semi-synthetic opioid analgesics (e.g., phenanthrenes, phenylheptylamines, phenylpiperidines, morphinans, and benzomorphans) where exemplary opioid analgesics include morphine, oxycodone, fentanyl, pentazocine, hydromorphone, meperidine, methadone, levorphanol, oxymorphone, levallorphan, codeine, dihydrocodeine, hydrocodone, propoxyphene, nalmefene, nalorphine, naloxone, naltrexone, buprenorphine, butorphanol, nalbuphine, and pentazocine; ionotropic glutamate receptor agonists and antagonists, e.g., N-methyl-D-aspartate (NMDA) receptor agonists, antagonists, and allosteric modulators, kainate (KA) receptor agonists and antagonists, and allosteric modulators, α-amino-3-hydroxy-5-methylisoxazole-4-propionic acid (AMPA) receptor agonists and antagonists and allosteric modulators, and metabotropic glutamate receptor agonists and antagonists and allosteric modulators; non-opioid analgesics, e.g., acetylsalicylic acid, choline magnesium trisalicylate, acetaminophen, ibuprofen, fenoprofen, diflusinal, and naproxen; muscarinic receptor agonists; muscarinic receptor antagonists; acetylcholine receptor agonists; acetylcholine receptor antagonists; serotonin receptor agonists; serotonin receptor antagonists; enzyme inhibitors; a benzodiazepine, e.g. chlordiazepoxide, clorazepate, diazepam, flurazepam, lorazepam, oxazepam, temazepam or triazolam; a barbiturate sedative, e.g. amobarbital, aprobarbital, butabarbital, butabital, mephobarbital, metharbital, methohexital, pentobarbital, phenobartital, secobarbital, talbutal, theamylal, or thiopental; an $H_1$ antagonist having a sedative action, e.g. diphenhydramine, pyrilamine, promethazine, chlorpheniramine, or chlorcyclizine; an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, topiramate, neramexane, or perzinfotel; an alpha-adrenergic, e.g. doxazosin, tamsulosin, clonidine, guanfacine, dexmetatomidine, modafinil, phentolamine, terazasin, prazasin or 4-amino-6,7-dimethoxy-2-(5-methane-sulfonamido-1,2,3,4-tetrahydroisoquinol-2-yl)-5-(2-pyridyl) quinazoline; a tricyclic antidepressant, e.g. desipramine, imipramine, amitriptyline, or nortriptyline; an anticonvulsant, e.g. carbamazepine, lamotrigine, topiratmate, or valproate; a tachykinin (NK) antagonist, particularly an NK-3, NK-2 or NK-1 antagonist, e.g. (α-R,9R)-7-[3,5-bis(trifluoromethyl) benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl) phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy) phenyl]-methylamino]-2-phenylpiperidine (2S,3S); a muscarinic antagonist, e.g. oxybutynin, tolterodine, propiverine, tropsium chloride, darifenacin, solifenacin, temiverine, or ipratropium; a cyclooxygenase-2 (COX-2) selective inhibitor, e.g. celecoxib, rofecoxib, parecoxib, valdecoxib, deracoxib, etoricoxib, or lumiracoxib; a vanilloid receptor agonist (e.g. resinferatoxin) or antagonist (e.g. capsazepine); a beta-adrenergic such as propranolol; a 5-HT receptor agonist or antagonist, e.g., a 5-$HT_1B/_1D$ agonist such as eletriptan, sumatriptan, naratriptan, zolmitriptan or rizatriptan; a 5-HT$_2$A receptor antagonist such as R(+)-α-(2,3-dimethoxyphenyl)-1-[2-(4-fluorophenylethyl)]-4-piperidinemethanol (MDL-100907); and the like.

Suitable ligands for Na$^+$ channels include, but are not limited to, lidocaine, novocaine, xylocaine, lignocaine, novocaine, carbocaine, etidocaine, procaine, prontocaine, prilocaine, bupivacaine, cinchocaine, mepivacaine, quinidine, flecainide, procaine, N-[[2'-(aminosulfonyl)biphenyl-4-yl]methyl]-N'-(2,2'-bithien-5-ylmethyl)succinamide (BPBTS), QX-314, saxitoxin, tetrodotoxin, and a type III conotoxin. Suitable ligands for Na$^+$ channels also include, but are not limited to, tetrodotoxin, saxitoxin, guanidinium, polyamines (e.g. spermine, cadaverine, putrescine, μ-conotoxin, and δ-conotoxin.

Suitable ligands for K$^+$ channels include, but are not limited to, quaternary ammonium (e.g., tetraethyl ammonium, tetrabutylammonium, tetrapentylammonium), 4-aminopyridine, sulfonylurea, Glibenclamide; Tolbutamide; Phentolamine, qiunine, qunidine, peptide toxins (e.g., charybdotoxin, agitoxin-2, apamin, dendrotoxin, VSTX1, hanatoxin-1, hanatoxin-2, and Tityus toxin K-α.

Suitable ligands for CNG and HCN channels include, but are not limited to, 1-cis diltiazem and ZD7288. Suitable ligands for glycine receptors include, but are not limited to, strychnine and picrotoxin.

Suitable ligands for nicotinic acetylcholine receptors include, but are not limited to, (+)-tubocurarine, Methyllycaconitine, gallamine, Nicotine; Anatoxin A, epibatidine, ABT-94, Lophotoxin, Cytisine, Hexamethonium, Mecamylamine, and Dihydro-β-erythroidine. Suitable ligands for muscarinic acetylcholine receptors include, but are not limited to, a muscarinic acetylcholine receptor antagonist as described in U.S. Pat. No. 7,439,255; AF267B (see, e.g., U.S. Pat. No. 7,439,251); phenylpropargyloxy-1,2,5-thiadiazole-quinuclidine; carbachol; pirenzapine; migrastatin; a compound as described in U.S. Pat. No. 7,232,841; etc.

Suitable ligands for GABA receptors include, but are not limited to, Muscimol, THIP, Procabide, bicuculine, picrotoxin, gabazine, gabapentin, diazepam, clonazepam, flumazenil, a β-carboline carboxylate ethyl ester, baclofen, faclofen, and a barbiturate.

In some cases, e.g., where the target ligand-binding polypeptide is an mGluR, the ligand is glutamate. In some cases, where the target ligand-binding polypeptide is an mGluR receptor, the ligand will be a naturally occurring or synthetic ligand of an mGluR receptor (including but not limited to mGluR2, mGluR3, mGluR5 and mGluR6).

Many suitable ligands will be known to those skilled in the art; and the choice of ligand will depend, in part, on the target (e.g., receptor, ion channel, enzyme, etc.) to which the ligand binds.

Fluorophores

In some cases, a conjugate of the present disclosure comprises a fluorophore. For example, as noted above, Q$^2$ can be a label, such as a fluorophore. Examples of fluorophores include, but are not limited to: an Alexa Fluor® dye (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like), an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine isothiocyanate (TRITC), tetramethylrhodamine (TMR), Silicon Rhodamine (SiR), Texas Red, Oregon Green, Pacific Blue, Pacific Green, and Pacific Orange.

Target Ligand-Binding Polypeptides

As noted above, a conjugate of the present disclosure includes a ligand that binds to a target ligand-binding polypeptide.

Suitable target ligand-binding proteins include ion and macromolecule permeant channels; receptors (including, but not limited to, ionotropic receptors that bind transmitters; ionotropic receptors that bind hormones; metabotropic receptors and other G protein coupled receptors; receptor tyrosine kinases; growth factor receptors; and other membrane receptors that signal by binding to soluble or membrane-bound or extracellular small molecules or proteins); transporters (including but not limited to ion transporters, organic molecule transporters, peptide transporters, and protein transporters); enzymes (including but not limited to kinases; phosphatases; ubiquitin ligases; acetylases; oxoreductases; lipases; enzymes that add lipid moieties to proteins or remove them; proteases; and enzymes that modify nucleic acids, including but not limited to ligases, helicases, topoisomerases, and telomerases); motor proteins (including kinesins, dyenins and other microtobule-based motors, myosins and other actin-based motors, DNA and RNA polymerases and other motors that track along polynucleotides); scaffolding proteins; adaptor proteins; cytoskeletal proteins; and other proteins that localize or organize protein domains and superstructures within cells.

In some cases, the target ligand-binding polypeptide is a transcription regulator, an ion channel, a cation channel, a ligand-gated ion channel, a voltage-gated ion channel, a quorum sensor, a pheromone receptor, a neurotransmitter receptor, a G-protein-coupled receptor (GPCR), or an enzyme. In some cases, the target ligand-binding polypeptide is a cation channel, e.g., a potassium channel, a sodium channel, or a calcium channel. In some cases, the target ligand-binding polypeptide is a glutamate receptor, a metabotropic glutamate receptor, an ionotropic glutamate receptor, an ionotropic nicotinic acetylcholine receptor, an ionotropic GABA-A receptor, or an ionotropic purinergic P2X receptor. In some cases, the target ligand-binding polypeptide is selected from a glutamate receptor, a metabotropic glutamate receptor (mGluR) an ionotropic glutamate receptor (e.g., a kainate receptor; an AMPA receptor; an NMDA receptor), an ionotropic nicotinic acetylcholine receptor, an ionotropic GABA-A receptor, a metabotropic GABA-B receptor, a metabotropic dopamine receptor, an ionotropic purinergic P2X receptor, a metabotropic purinergic P2Y receptor, a metabotropic serotonin receptor, an ionotropic serotonin receptor, an ionotropic glycine receptor, a cation channel, a potassium channel, a calcium channel, a sodium channel, a proton channel, an anion channel and a chloride channel.

In some cases, the target ligand-binding polypeptide is selected from a metabotropic glutamate receptor, where metabotropic glutamate receptors include, e.g., mGluR2, mGluR3, mGluR5, mGluR6, and the like.

Polypeptides that Bind Target Ligand-Binding Polypeptides

As noted above, a conjugate of the present disclosure includes an affinity agent that binds: i) a target ligand-binding polypeptide; or ii) a polypeptide that binds a target ligand-binding polypeptide.

In some cases, a polypeptide that binds a target ligand-binding polypeptide is a fusion polypeptide comprising: i) an antibody that binds the target ligand-binding polypeptide; and ii) a polypeptide that binds the affinity agent present in the conjugate. For example, a polypeptide that binds the affinity agent present in the conjugate can be a SNAP polypeptide (where the affinity agent is benzylguanine), a CLIP polypeptide (where the affinity agent is benzylcytosine), or a HALO polypeptide (where the affinity agent is a chloroalkane).

Exemplary Conjugates

In some cases, a conjugate of the present disclosure is a compound having Formula I:

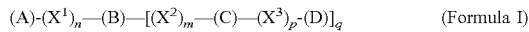
(Formula I)

wherein:
A is an affinity agent;
$X^1$, when present, is a first linker, wherein n is 0 or 1;
B is a branched linker;
$X^2$, when present, is a second linker, wherein m is 0 or 1;
C is a photoisomerizable group;
$X^3$, when present, is a third linker, wherein p is 0 or 1;
D is a ligand; and
q is an integer from 2 to 10.

Suitable affinity agents are those described in the present disclosure. For example, as described in the present disclosure, the affinity agent can be, but is not limited to, benzylguanine, benzylcytosine, chloroalkane, an antibody, an aptamer, a small molecule or a peptide, and the like. In some cases, the affinity agent is an antibody specific for a target ligand-binding polypeptide. Non-limiting examples of suitable antibodies include, e.g., a nanobody specific for a target ligand-binding polypeptide (e.g., a nanobody that specifically binds mGluR2); and a scFv antibody specific for a target ligand-binding polypeptide (e.g., a scFv that specifically binds mGluR2).

$X^1$, when present, is a first linker, wherein n is 0 or 1. For instance, when n is 0, then $X^1$ is not present, and A is connected directly to B. In other instances, n is 1 and $X^1$ is present. Similarly, $X^2$, when present, is a second linker, wherein m is 0 or 1. For instance, when m is 0, then $X^2$ is not present, and B is connected directly to C. In other instances, m is 1 and $X^2$ is present. Similarly, $X^3$, when present, is a third linker, wherein p is 0 or 1. For instance, when p is 0, then $X^3$ is not present, and C is connected directly to D. In other instances, p is 1 and $X^3$ is present. In some cases, at least one of $X^1$, $X^2$ and $X^3$ is present. In some cases, only one of $X^1$, $X^2$ and $X^3$ is present. In some cases, $X^1$ and $X^2$ are present and $X^3$ is absent. In some cases, $X^1$ and $X^3$ are present and $X^2$ is absent. In some cases, $X^2$ and $X^3$ are present and $X^1$ is absent. In some cases, $X^1$, $X^2$ and $X^3$ are present.

Suitable linkers for $X^1$, $X^2$ and/or $X^3$ include, but are not limited to, a polycarbon chain; poly(ethylene glycol); a peptide; and the like. In some cases, the linker is a $C_1$-$C_{25}$ alkyl. In some cases, the linker is a substituted $C_1$-$C_{25}$ alkyl. In some cases, the linker is poly(ethylene glycol) (PEG), where the PEG comprises from 2 to 50 ethylene glycol monomers; e.g., the PEG comprises from 2 to 5, from 5 to 10, from 10 to 15, from 15 to 20, from 20 to 25, from 25 to 30, from 30 to 35, from 35 to 40, from 40 to 45, or from 45 to 50, ethylene glycol units. For example, the linker can be PEG, where the PEG comprises 12 ethylene glycol monomers (i.e., PEG12). In some cases, the linker is a peptide of from 2 amino acids to 50 amino acids; e.g., from 2 amino acids to 5 amino acids, from 5 amino acids to 10 amino acids, from 10 amino acids to 15 amino acids, from 15 amino acids to 20 amino acids, from 20 amino acids to 25 amino acids, from 25 amino acids to 30 amino acids, or from 30 amino acids to 50 amino acids. In some cases, the linker is a peptide of 2, 3, 4, 5, 6, 7, 8, 9, or 10 amino acids in length.

Suitable branched linkers include those described in the present disclosure. For example, suitable branched linkers include branched linkers comprising 1 or more (e.g., 1 to 10) glutaramide groups, as described herein. Other suitable branched linkers include, but are not limited to dendrimeric structures, such as polyamidoamine (PAMAM) dendrimers, poly ethyleneglycol (PEG) dendrimers, and the like.

Suitable photoisomerizable groups include those described in the present disclosure, such as, but not limited to a moiety selected from an azobenzene, a cyclic azobenzene, an azoheteroarene, a fulgide, a spiropyran, a triphenyl methane, a thioindigo, a diarylethene, and an overcrowded alkene. In some cases, the photoisomerizable group is an azobenzene (e.g., as described herein).

Suitable ligands include those described in the present disclosure. In some cases, the ligand is an agonist, an antagonist, an allosteric modulator, or a blocker (e.g., as described herein).

In other embodiments of Formula I, D is a label, a reactive group, or a second affinity agent as described in the present disclosure.

In some cases, the conjugate has the formula (A)-$(X^1)_n$—(B)—$[(X^2)_m$—(C)-(D)$]_q$.

In some cases, the conjugate has the formula (A)-$(X^1)_n$—(B)—$[(C)-(D)]_q$.

In some cases, the conjugate has the formula (A)-(B)—$[(X^2)_m$—(C)—$(X^3)_p$-(D)$]_q$.

In some cases, the conjugate has the formula (A)-(B)—$[(X^2)_m$—(C)-(D)$]_q$.

In some cases, the conjugate has the formula (A)-$(X^1)_n$—(B)—$[(X^2)_m$—(C)—$(X^3)_p$-(D)$]_q$.

Any combination of suitable A, B, C and D moieties, with or without the first linker ($X^1$), the second linker ($X^2$) or the third linker ($X^3$), may be used in a conjugate according to the present disclosure. Examples of conjugates include, but are not limited to conjugates where:

(i) A is benzylcytosine, B is a branched linker comprising glutaramide, C is an azobenzene, D is glutamate, and q is 2;

(ii) A is benzylcytosine, $X^1$ is PEG (e.g., PEG12), B is a branched linker comprising glutaramide, C is an azobenzene, D is glutamate, and q is 2;

(iii) A is benzylcytosine, $X^1$ is PEG (e.g., PEG12), B is a branched linker comprising glutaramide, C is azobenzene 380, D is glutamate, and q is 2;

(iv) A is benzylcytosine, $X^1$ is PEG (e.g., PEG12), B is a branched linker comprising glutaramide, C is azobenzene 460, D is glutamate, and q is 2;

(v) A is chloroalkane, B is a branched linker comprising glutaramide, C is an azobenzene, D is glutamate, and q is 2;

(vi) A is chloroalkane, $X^1$ is PEG (e.g., PEG12), B is a branched linker comprising glutaramide, C is an azobenzene, D is glutamate, and q is 2;

(vii) A is chloroalkane, $X^1$ is PEG (e.g., PEG12), B is a branched linker comprising glutaramide, C is azobenzene 380, D is glutamate, and q is 2;

(viii) A is chloroalkane, $X^1$ is PEG (e.g., PEG12), B is a branched linker comprising glutaramide, C is azobenzene 460, D is glutamate, and q is 2;

(ix) A is benzylguanine, B is a branched linker comprising glutaramide, C is an azobenzene, D is glutamate, and q is 2;

(x) A is benzylguanine, B is a branched linker comprising glutaramide, $X^2$ is PEG (e.g., PEG12), C is an azobenzene, D is glutamate, and q is 2;

(xi) A is benzylguanine, B is a branched linker comprising glutaramide, $X^2$ is PEG (e.g., PEG12), C is azobenzene 380, D is glutamate, and q is 2;

(xii) A is benzylguanine, B is a branched linker comprising glutaramide, $X^2$ is PEG (e.g., PEG12), C is azobenzene 460, D is glutamate, and q is 2;

(xiii) A is benzylguanine, B is a branched linker comprising three glutaramide moieties, C is an azobenzene, D is glutamate, and q is 4;

(xiv) A is benzylguanine, B is a branched linker comprising three glutaramide moieties, $X^2$ is PEG (e.g., PEG12), C is an azobenzene, D is glutamate, and q is 4;

(xv) A is benzylguanine, B is a branched linker comprising three glutaramide moieties, $X^2$ is PEG (e.g., PEG12), C is azobenzene 380, D is glutamate, and q is 4;

(xvi) A is benzylguanine, B is a branched linker comprising three glutaramide moieties, $X^2$ is PEG (e.g., PEG12), C is azobenzene 460, D is glutamate, and q is 4;

and the like.

Any combination of suitable A, B, C and D moieties, with or without the first linker ($X^1$), the second linker ($X^2$) or the third linker ($X^3$), may be used in a conjugate according to the present disclosure. Examples of conjugates include, but are not limited to conjugates where:

(i) A is an antibody specific for a target ligand-binding polypeptide, B is a branched linker comprising glutaramide, C is azobenzene 460, D is glutamate, and q is 2;

(ii) A is an antibody specific for a target ligand-binding polypeptide, B is a branched linker comprising glutaramide, $X^2$ is PEG (e.g., PEG12 or PEG28), C is azobenzene 460, D is glutamate, and q is 2;

(iii) A is an antibody specific for a target ligand-binding polypeptide, B is a branched linker comprising three glutaramide moieties, C is azobenzene 460, D is glutamate, and q is 4;

(iv) A is an antibody specific for a target ligand-binding polypeptide, B is a branched linker comprising three glutaramide moieties, $X^2$ is PEG (e.g., PEG12 or PEG28), C is azobenzene 460, D is glutamate, and q is 4;

(v) A is an antibody specific for a metabotropic glutamate receptor (mGluR), B is a branched linker comprising glutaramide, C is azobenzene 460, D is glutamate, and q is 2;

(vi) A is an antibody specific for a mGluR (e.g., mGluR2, mGluR3, mGluR4, mGluR5, or mGluR6), B is a branched linker comprising glutaramide, $X^2$ is PEG (e.g., PEG12 or PEG28), C is azobenzene 460, D is glutamate, and q is 2;

(vii) A is an antibody specific for a mGluR (e.g., mGluR2, mGluR3, mGluR4, mGluR5, or mGluR6), B is a branched linker comprising three glutaramide moieties, C is azobenzene 460, D is glutamate, and q is 4;

(vii) A is an antibody specific for a mGluR (e.g., mGluR2, mGluR3, mGluR4, mGluR5, or mGluR6), B is a branched linker comprising three glutaramide moieties, $X^2$ is PEG (e.g., PEG12 or PEG28), C is azobenzene 460, D is glutamate, and q is 4;

(vii) A is an antibody specific for a mGluR2 (e.g., mGluR2, mGluR3, mGluR4, mGluR5, or mGluR6), B is a branched linker comprising glutaramide, C is azobenzene 460, D is glutamate, and q is 2;

(ix) A is an antibody specific for mGluR2, B is a branched linker comprising glutaramide, $X^2$ is PEG (e.g., PEG12 or PEG28), C is azobenzene 460, D is glutamate, and q is 2;

(x) A is an antibody specific for mGluR2, B is a branched linker comprising three glutaramide moieties, C is azobenzene 460, D is glutamate, and q is 4;

(xi) A is an antibody specific for mGluR2, B is a branched linker comprising three glutaramide moieties, $X^2$ is PEG (e.g., PEG12 or PEG28), C is azobenzene 460, D is glutamate, and q is 4;

(xii) A is a nanobody specific for mGluR2, B is a branched linker comprising glutaramide, C is azobenzene 460, D is glutamate, and q is 2;

(xiii) A is a nanobody specific for mGluR2, B is a branched linker comprising glutaramide, $X^2$ is PEG (e.g., PEG12 or PEG28), C is azobenzene 460, D is glutamate, and q is 2;

(xiv) A is a nanobody specific for mGluR2, B is a branched linker comprising three glutaramide moieties, C is azobenzene 460, D is glutamate, and q is 4;

(xv) A is a nanobody specific for mGluR2, B is a branched linker comprising three glutaramide moieties, $X^2$ is PEG (e.g., PEG12 or PEG28), C is azobenzene 460, D is glutamate, and q is 4;

(xii) A is a scFv specific for mGluR2, B is a branched linker comprising glutaramide, C is azobenzene 460, D is glutamate, and q is 2;

(xiii) A is a scFv specific for mGluR2, B is a branched linker comprising glutaramide, $X^2$ is PEG (e.g., PEG12 or PEG28), C is azobenzene 460, D is glutamate, and q is 2;

(xiv) A is a scFv specific for mGluR2, B is a branched linker comprising three glutaramide moieties, C is azobenzene 460, D is glutamate, and q is 4;

(xv) A is a scFv specific for mGluR2, B is a branched linker comprising three glutaramide moieties, $X^2$ is PEG (e.g., PEG12 or PEG28), C is azobenzene 460, D is glutamate, and q is 4;

(xvi) A is an antibody specific for a mGluR (e.g., mGluR2, mGluR3, mGluR4, mGluR5, or mGluR6), $X^1$ is PEG (e.g., PEG12 or PEG28), B is a branched linker comprising three glutaramide moieties, C is azobenzene 460, D is glutamate, and q is 4;

(xvii) A is an scFv specific for a mGluR (e.g., mGluR2, mGluR3, mGluR4, mGluR5, or mGluR6), $X^1$ is PEG (e.g., PEG12 or PEG28), B is a branched linker comprising three glutaramide moieties, C is azobenzene 460, D is glutamate, and q is 4;

(xviii) A is a nanobody specific for a mGluR (e.g., mGluR2, mGluR3, mGluR4, mGluR5, or mGluR6), $X^1$ is PEG (e.g., PEG12 or PEG28), B is a branched linker comprising three glutaramide moieties, C is azobenzene 460, D is glutamate, and q is 4;

(xix) A is a nanobody specific for mGluR4, B is a branched linker comprising three glutaramide moieties, C is azobenzene 460, D is glutamate, and q is 4;

(xx) A is a nanobody specific for mGluR4, B is a branched linker comprising three glutaramide moieties, $X^2$ is PEG (e.g., PEG12 or PEG28), C is azobenzene 460, D is glutamate, and q is 4;
(xxi) A is a nanobody specific for mGluR4, $X^1$ is PEG (e.g., PEG12 or PEG28), B is a branched linker comprising three glutaramide moieties, C is azobenzene 460, D is glutamate, and q is 4;
(xxii) A is a nanobody specific for mGluR5, B is a branched linker comprising three glutaramide moieties, C is azobenzene 460, D is glutamate, and q is 4;
(xxiii) A is a nanobody specific for mGluR5, B is a branched linker comprising three glutaramide moieties, $X^2$ is PEG (e.g., PEG12 or PEG28), C is azobenzene 460, D is glutamate, and q is 4;
(xxiv) A is a nanobody specific for mGluR5, $X^1$ is PEG (e.g., PEG12 or PEG28), B is a branched linker comprising three glutaramide moieties, C is azobenzene 460, D is glutamate, and q is 4;
(xxv) A is a nanobody specific for mGluR6, B is a branched linker comprising three glutaramide moieties, C is azobenzene 460, D is glutamate, and q is 4;
(xxvi) A is a nanobody specific for mGluR6, B is a branched linker comprising three glutaramide moieties, $X^2$ is PEG (e.g., PEG12 or PEG28), C is azobenzene 460, D is glutamate, and q is 4;
(xxvii) A is a nanobody specific for mGluR6, $X^1$ is PEG (e.g., PEG12 or PEG28), B is a branched linker comprising three glutaramide moieties, C is azobenzene 460, D is glutamate, and q is 4;
and the like.

Compositions and Combination Comprising a Photoswitch Conjugate and a Fusion Polypeptide In some cases, the present disclosure provides compositions and/or combinations comprising: a) a photoswitch conjugate of the present disclosure; and b) a fusion polypeptide that comprises a polypeptide that binds to the affinity agent present in the photoswitch conjugate, or a polynucleotide comprising a nucleotide sequence encoding the fusion polypeptide. The photoswitch conjugate and the fusion polypeptide or fusion polynucleotide can be a part of the same composition and administered to a subject together. Alternatively, the photoswitch conjugate and the fusion polypeptide or fusion polynucleotide can be a part of a therapeutic approach comprising a combination of agents administered at different times and/or by different means or modes of administration. In some cases, a composition of the present disclosure comprises: a) a photoswitch conjugate of the present disclosure; and b) a fusion polypeptide (or a polynucleotide encoding the fusion polypeptide) comprising: i) a receptor for a ligand (e.g., a ligand present in a photoswitch conjugate of the present disclosure); and ii) a fusion partner, where the fusion partner is a polypeptide that binds the affinity moiety present in the photoswitch conjugate. In some cases, a composition of the present disclosure comprises: a) a photoswitch conjugate of the present disclosure; and b) a first fusion polypeptide (or a polynucleotide encoding it) comprising: i) a receptor for a ligand (e.g., a ligand present in a photoswitch conjugate of the present disclosure); and ii) a fusion partner, where the fusion partner displays an epitope that is bound by an antibody present in a second fusion polypeptide, the second fusion polypeptide comprising: i) an antibody that binds the epitope present in the fusion partner of the first fusion polypeptide; and ii) a polypeptide binds the affinity moiety present in the photoswitch conjugate.

Composition Comprising a Photoswitch Conjugate and a Single Fusion Polypeptide

In some cases, a composition or combination of the present disclosure comprises: a) a photoswitch conjugate of the present disclosure; and b) a fusion polypeptide (or a polynucleotide comprising a nucleotide sequence encoding the fusion polypeptide) that comprises a polypeptide that binds to the affinity agent present in the photoswitch conjugate. In some cases, the fusion polypeptide comprises: a) a receptor for a ligand (e.g., a ligand present in a photoswitch conjugate of the present disclosure); and b) a fusion partner, where the fusion partner is a SNAP polypeptide, a CLIP polypeptide, or a HALO polypeptide. For example, in some cases, the receptor for the ligand is a glutamate receptor, a metabotropic glutamate receptor (mGluR), an ionotropic glutamate receptor (e.g., a kainate receptor; an AMPA receptor; an NMDA receptor), an ionotropic nicotinic acetylcholine receptor, an ionotropic GABA-A receptor, a metabotropic GABA-B receptor, a metabotropic dopamine receptor, an ionotropic purinergic P2X receptor, a metabotropic purinergic P2Y receptor, a metabotropic serotonin receptor, an ionotropic serotonin receptor, an ionotropic glycine receptor, a cation channel, a potassium channel, a calcium channel, a sodium channel, a proton channel, an anion channel, and a chloride channel.

In some cases, a composition or combination of the present disclosure comprises: a) a conjugate of the present disclosure; and b) a nucleic acid comprising a nucleotide sequence encoding the fusion polypeptide. The nucleic acid can be an expression vector. The nucleotide sequence can be operably linked to a promoter. The expression vector can be, e.g., a recombinant viral expression vector. As a non-limiting example, the expression vector can be an adeno-associated virus (AAV) vector, where the recombinant AAV vector comprises a heterologous nucleotide sequence encoding the fusion polypeptide. The recombinant AAV vector can also comprise a nucleotide sequence encoding a variant capsid protein, where the variant capsid protein provides for infection of a retinal cell. In some cases, the recombinant AAV vector will be administered to the eye. In some cases, the recombinant AAV vector will be administered to the eye intravitreally.

In some cases, a composition or combination of the present disclosure comprises: a) a photoswitch conjugate of the present disclosure, where the affinity agent is a nucleoside base derivative as described above (e.g., benzylguanine; benzylcytosine; chloroalkane; a chloropyrimidine; etc.); and b) a fusion polypeptide that comprises: i) an antibody (e.g., a scFv or a nanobody) specific for a target ligand-binding polypeptide; and ii) a polypeptide (e.g., a SNAP polypeptide; a CLIP polypeptide; a HALO polypeptide; and the like) that binds to the affinity agent present in the conjugate. In some cases, a composition or combination of the present disclosure comprises: a) a photoswitch conjugate of the present disclosure, where the affinity agent is a nucleoside base derivative as described above (e.g., benzylguanine; benzylcytosine; chloroalkane; a chloropyrimidine; etc.); and b) a fusion polypeptide that comprises: i) a nanobody or an scFv specific for an mGluR; and ii) a polypeptide (e.g., a SNAP polypeptide; a CLIP polypeptide; a HALO polypeptide; and the like) that binds to the affinity agent present in the conjugate. In some cases, a composition or combination of the present disclosure comprises: a) a photoswitch conjugate of the present disclosure, where the affinity agent is a nucleoside base derivative as described above (e.g., benzylguanine; benzylcytosine; chloroalkane; a chloropyrimidine; etc.); and b) a fusion polypeptide that comprises: i) a nanobody or an scFv specific for mGluR2, mGluR3, mGluR5, or mGluR5; and ii) a polypeptide (e.g., a SNAP polypeptide; a CLIP polypeptide; a HALO polypeptide; and the like) that binds to the affinity agent present in the conjugate.

Composition Comprising a Photoswitch Conjugate and Two Fusion Polypeptides

In some cases, the fusion polypeptide comprises: a) a receptor for a ligand (e.g., a ligand present in a photoswitch conjugate of the present disclosure); and b) a fusion partner, where the fusion partner is an antigen that is bound specifically by an antibody. In some cases, the antibody is a fusion polypeptide comprising: a) the antibody; and b) a fusion partner, where the fusion partner is a SNAP polypeptide, a CLIP polypeptide, or a HALO polypeptide. Other suitable fusion partners include, e.g., an epitope tag (e.g., a hemagglutinin tag, a FLAG tag, a poly(His) tag, and the like). Also suitable for use is a halo-based oligonucleotide binder (HOB) polypeptide. See, e.g., Kossman et al. (2016) *Chembiochem.* 17:1102. A HOB polypeptide binds chlorohexyl moieties. Also suitable for use is a trimethoprim (TMP) tag, an engineered form of *E. coli* dihydrofolate reductase (DHFR) that forms a non-covalent high-affinity complex with trimethoprim derivatives. See, e.g., Gallagher et al. (2009) *ACS Chem. Biol.* 4:547; and Jing and Cornish (2013) *ACS Chem. Biol.* 8:1704.

SNAP

In some cases, a SNAP polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence: MDKDCEMKRTTLD-SPLGKLELSGCEQGLHRIIFLGKGTSAADAVEVPA-PAAVLGGPEPL MQATAWLNAY-FHQPEAIEEFPVPALHHPVFQQESFTRQVLWKLLKV-VKFGEVISYSHLA AFAGNPAATAAVKTAFSGNPVPI-FIPCHRVVQGDFDVGGYEGGFAVKEWEEAHEGHRF GKPGEG (SEQ ID NOG). A SNAP polypeptide binds $O^6$-benzylguanine (BG).

In some cases, a SNAP polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

```
                                           (SEQ ID NO: 4)
DKDCEMKRTTLDSPLGKLELSGCEQGLHEIKLLGKGTSAADAVEVPAPAA

VLGGPEPLMQATAWLNAYFHQPEAIEEFPVPALHHPVFQQESFTRQVLWK

LLKVVKFGEVISYQQLAALAGNPAATAAVKTALSGNPVPILIPCHRVVSS

SGAVGGYEGGLAVKEWLLAHEGHRLGKPGLG.
```

In some cases, the SNAP polypeptide or variant thereof binds to benzylguanine.

CLIP

A CLIP polypeptide can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence: MDKDCEMKRTTLD-SPLGKLELSGCEQGLHRIIFLGKGTSAADAVEVPA-PAAVLGGPEPL IQATAWLNAY-FHQPEAIEEFPVPALHHPVFQQESFTRQVLWKLL-KVVKFGEVISESHLA ALVGNPAATAAVN-TALDGNPVPILIPCHRVVQGDSDVGPYLGGLAVKEW-LLAHEGHRL GKPGLG (SEQ ID NO:2). A CLIP polypeptide can bind $O^2$-benzylcytosine (BC).

HALO

A HALO polypeptide can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence: MAEIGTGFPFDPHYVEVLGERM-HYVDVGPRDGTPVLFLHGNPTSSYVWRNIIPHVAPTH RCIAPDLIGMGKSDKPDLGYFFDDHVRFMDAFIEAL-GLEEVVLVIHDWGSALGFHWAK RNPERVKGIAFME-FIRPIPTWDEWPEFARETFQAFRTTDVGRKLI-IDQNVFIEGTLPMGVV RPLTEVEMDHYREPFLNPVDREPLWRFPNELPI-AGEPANIVALVEEYMDWLHQSPVPKL LFWGTPGVLIPPAEAARLAKSLPNCKAV-DIGPGLNLLQEDNPDLIGSEIARWLSTLEISG (SEQ ID NOG). A HALO polypeptide binds chloroalkane.

Vectors

The present disclosure also provides expression vectors, delivery vectors and other vectors comprising the compositions and/or combinations described herein.

Expression vectors include, but are not limited to, any vector suitable for in vitro or ex vivo delivery of a composition of the disclosure to a cell of the disclosure, by any means. In some embodiments, an expression vector comprises a plasmid. In some cases, the plasmid is electroporated into a cell of the disclosure. Expression vectors of the disclosure may also comprise delivery vectors of the disclosure when used to introduce a composition in vitro or ex vivo.

Delivery vectors include, but are not limited to, any vector suitable for in vivo delivery of a composition of the disclosure to a cell of the disclosure when in vivo or in situ (in the context of an intact eye). Delivery vectors of the disclosure include, but are not limited, to viral vectors and non-viral vectors. Exemplary viral vectors include, but are not limited to, adeno-associated vectors of any serotype. Exemplary non-viral vectors include, but are not limited to, lipid vectors, polymer vectors and particle vectors. Lipid vectors include, but are not limited to, liposomes, lipid nanoparticles, micelles, lipid polymersomes, and exosomes. Polymer vectors include, but are not limited to, polymersomes, lipid nanoparticles, and nanoparticles. Particle vectors include, but are not limited to, nanoparticles of all geometries and compositions.

In some cases, a delivery vector of the disclosure comprises a composition of the disclosure, including a composition comprising a sequence encoding a promoter operably linked to a polynucleotide encoding a polypeptide of interest. In some embodiments of the delivery vectors of the disclosure, the vector is a viral vector. In some cases, the viral vector is an adeno-associated vector (AAV). In some cases, the AAV is a recombinant AAV (rAAV). In some cases, the rAAV comprises a sequence isolated or derived from an AAV of a first serotype and a sequence isolated or derived from an AAV of a second serotype. In some cases, the rAAV comprises a capsid sequence isolated or derived from an AAV of a first serotype and a capsid insert sequence isolated or derived from an AAV of a second serotype. Exemplary AAV serotypes include, but are not limited to, AAV1, AAV2, AAV3, AAV4, AAV5, AAV6, AAV7, AAV8, AAV9, and any combination thereof. In some cases, an AAV vector of the disclosure comprises a sequence isolated or derived from one or more of AAV2, AAV4, AAV5 and AAV8.

In some cases, an AAV vector of the disclosure comprises a wild type sequence from one or more of AAV1, AAV2, AAV3, AAV4, AAV5, AAV6, AAV7, AAV8 and AAV9. In some cases, an AAV vector of the disclosure comprises a capsid sequence isolated or derived from one or more of AAV1, AAV2, AAV3, AAV4, AAV5, AAV6, AAV7, AAV8 and AAV9. In some cases, an AAV vector of the disclosure comprises a capsid sequence isolated or derived from AAV2 and AAV4. In some cases, an AAV vector of the disclosure comprises a capsid sequence isolated or derived from AAV2 and AAV5. In some cases, an AAV vector of the disclosure comprises a capsid sequence isolated or derived from AAV2 and AAV8. In some cases, an AAV vector of the disclosure comprises a recombinant or chimeric capsid sequence comprising two or more sequences isolated or derived from AAV1, AAV2, AAV3, AAV4, AAV5, AAV6, AAV7, AAV8 and AAV9.

In certain specific embodiments of the present disclosure, modified adeno-associated vectors (AAV) are used as described in WO2018/022905 and/or U.S. Application Ser. No. 63/032,206, the contents of which are incorporated herein by reference in their entireties.

In some cases, delivery vectors, including AAV vectors, target a retinal cell type. In some cases, delivery vectors, including AAV vectors, have a tropism for a retinal cell type. In some cases, the retinal cell type is a neuron. In some cases, the retinal cell type is a retinal ganglion cell. In some cases, the retinal cell type is a horizontal cell. In some cases, the retinal cell type is an amacrine cell. In some cases, the retinal cell type is a bipolar cell. In some cases, the retinal cell type is a photoreceptor cell. In some cases, the retinal cell type is not a photoreceptor. Photoreceptor cells include rod cells and cone cells.

In some cases, the cell is a retinal neuron or a progenitor cell thereof. In some embodiments, the progenitor cell is a neural fold cell, an early retinal progenitor cell (RPC), a late RPC, an embryonic stem cell (ESC), an induced pluripotent stem cell (iPSC), or a retinal pigmented epithelial (RPE) cell. In some embodiments, ESCs of the disclosure are neither isolated nor derived from a human embryo or human tissue.

In some cases, a composition of the disclosure may be delivered to a differentiated cell and/or a progenitor cell capable of becoming the differentiated cell type.

Regulatory Elements

In some cases, a nucleotide sequence encoding a polypeptide of the disclosure will be operably linked to one or more transcriptional regulatory elements. For example, in some cases, a nucleotide sequence encoding a gene product of interest is operably linked to a promoter, such as a constitutive promoter. In other cases, a nucleotide sequence encoding a gene product of interest is operably linked to an inducible promoter. In some instances, a nucleotide sequence encoding a gene product of interest is operably linked to a tissue-specific or cell type-specific regulatory element. For example, in some instances, a nucleotide sequence encoding a gene product of interest is operably linked to a retinal cell-specific promoter. For example, in some instances, a nucleotide sequence encoding a gene product of interest is operably linked to a photoreceptor-specific regulatory element (e.g., a photoreceptor-specific promoter), e.g., a regulatory element that confers selective expression of the operably linked gene in a photoreceptor cell. Suitable photoreceptor-specific regulatory elements include, e.g., a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225).

Suitable promoters include, but are not limited to, a CAG promoter (Miyazaki et al. (1989) Gene 79:269); a cytomegalovirus (CMV) promoter; a glutamate metabotropic receptor-6 (grm6) promoter (Cronin et al. (2014) EMBO Mol. Med. 6:1175); a Pleiades promoter (Portales-Casamar et al. (2010) Proc. Natl. Acad. Sci. USA 107:16589); a choline acetyltransferase (ChAT) promoter (Misawa et al. (1992) J. Biol. Chem. 267:20392); a vesicular glutamate transporter (V-glut) promoter (Zhang et al. (2011) Brain Res. 1377:1); a glutamic acid decarboxylase (GAD) promoter (Rasmussen et al. (2007) Brain Res. 1144:19; Ritter et al. (2016) J. Gene Med. 18:27); a cholecystokinin (CCK) promoter (Ritter et al. (2016) J. Gene Med. 18:27); a parvalbumin (PV) promoter; a somatostatin (SST) promoter; a neuropeptide Y (NPY) promoter; and a vasoactive intestinal peptide (VIP) promoter. Suitable promoters include, but are not limited to, a red cone opsin promoter, rhodopsin promoter, a rhodopsin kinase promoter, and a GluR promoter (e.g., a GluR6 promoter; also referred to as grm6). Suitable promoters include, but are not limited to, a vitelliform macular dystrophy 2 (VMD2) gene promoter, and an interphotoreceptor retinoid-binding protein (IRBP) gene promoter. Also suitable for use is an L7 promoter (Oberdick et al. (1990) Science 248:223), a thy-1 promoter, a recoverin promoter (Wiechmann and Howard (2003) Curr. Eye Res. 26:25); a calbindin promoter; and a beta-actin promoter. Suitable promoters include synthetic (non-naturally occurring) promoter/enhancer combinations.

Other suitable promoters useful in accordance with the present disclosure include, for example, a gamma-synuclein (SNCG) promoter (e.g., Chaffiol et al. (2017) Mol. Ther. 25(11) 2546), a CBh promoter (e.g., Grey et al. (2011) Hum. Gene Ther. 22(9): 1143-53), a miniCAG promoter (e.g., Grey et al. (2011) Hum. Gene Ther. 22(9): 1143-53), a neurofilament heavy (NEFH) promoter (Millington-Ward et al. (2020) Sci. Rep. 10:16515), a G protein-coupled receptor kinase 1 (GRK1) promoter (e.g., Khani et al. (2007) Invest. Ophthalmol. Vis. Sci. 48(9):3954-61), a retinaldehyde-binding protein 1 (RLBP1) promoter (e.g., Choi et al. (2015) Mol. Ther. Methods Clin. Dev. 2: 15022; Vogel et al. (2007) Invest. Ophthalmol. Vis. Sci. 48, 3872-3877), a vitelliform muscular dystrophy-2 (VMD2) promoter (e.g., Conlon et al. (2013) Hum. Gene Ther. Clin. Dev. 24, 23-28), a synapsin I (Syn1) promoter (e.g., Kugler et al. (2003)), an enhSyn1 promoter (e.g., Hioki et al. (2007) Gene Ther. 14(11):872-82), or a functional fragment or variant thereof.

In some embodiments of the disclosure, the composition further comprises one or more of a sequence comprising an enhancer, a sequence comprising an intron or any portion thereof, a sequence comprising an exon or any portion thereof, a sequence comprising a Kozak sequence, a sequence comprising a post-transcriptional response element (PRE), a sequence comprising an inverted terminal repeat (ITR) sequence, a sequence comprising a long terminal repeat (LTR) sequence, and a poly-A sequence.

In some embodiments of the compositions of the disclosure, the composition further comprises a linking element. A linking element of the disclosure may link the sequence encoding the promoter to the sequence encoding the polypeptide of interest. Alternatively, or in addition, a linking element of the disclosure may link, reversible or irreversibly the composition to one or more of a surface, a tag, a label (detectable or sequence barcode), a ligand, an epitope, a capture probe, a selectable marker, or a delivery vehicle of the disclosure.

Compositions

The embodiments further provide compositions comprising a conjugate of the present disclosure. Compositions comprising a conjugate of the present disclosure can include one or more of: a salt, e.g., NaCl, $MgCl_2$, KCl, $MgSO_4$, etc.; a buffering agent, e.g., a Tris buffer, N-(2-Hydroxyethyl) piperazine-N'-(2-ethanesulfonic acid) (HEPES), 2-(N-morpholino)ethanesulfonic acid (MES), 2-(N-morpholino)ethanesulfonic acid sodium salt (MES), 3-(N-Morpholino) propanesulfonic acid (MOPS), N-tris[hydroxymethyl] methyl-3-aminopropanesulfonic acid (TAPS), etc.; a solubilizing agent; a detergent, e.g., a non-ionic detergent such as Tween-20, Nonidet-P40, etc.; a protease inhibitor; and the like.

Pharmaceutical Compositions

The present disclosure provides pharmaceutical compositions comprising a conjugate of the present disclosure or a composition of the present disclosure. In some cases, the pharmaceutical composition is suitable for administering to an individual in need thereof. In some cases, the pharmaceutical composition is suitable for administering to an individual in need thereof, where the individual is a human.

A pharmaceutical composition comprising a conjugate or a composition of the present disclosure may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

A pharmaceutical composition comprising a conjugate or a composition of the present disclosure can optionally include a pharmaceutically acceptable carrier(s) that facilitate processing of an active ingredient into pharmaceutically acceptable compositions. As used herein, the term "pharmacologically acceptable carrier" refers to any carrier that has substantially no long-term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent.

Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in "Pharmaceutical Dosage Forms and Drug Delivery Systems" (Howard C. Ansel et al., eds., Lippincott Williams & Wilkins Publishers, $7^{th}$ ed. 1999); "Remington: The Science and Practice of Pharmacy" (Alfonso R. Gennaro ed., Lippincott, Williams & Wilkins, $20^{th}$ 2000); "Goodman & Gilman's The Pharmacological Basis of Therapeutics" Joel G. Hardman et al., eds., McGraw-Hill Professional, 10.sup.th ed. 2001); and "Handbook of Pharmaceutical Excipients" (Raymond C. Rowe et al., APhA Publications, $4^{th}$ edition 2003).

A subject pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a subject pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a subject pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or poly anhydrides; and (22) other nontoxic compatible substances employed in pharmaceutical formulations.

A conjugate or a composition of the present disclosure can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In a method of the present disclosure (described below), a conjugate or a composition of the present disclosure may be administered to the host using any convenient means capable of resulting in the desired reduction in disease condition or symptom. Thus, a conjugate or a composition of the present disclosure can be incorporated into a variety of formulations for therapeutic administration. More particularly, a conjugate or a composition of the present disclosure can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

A conjugate or a composition of the present disclosure can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A conjugate or a composition of the present disclosure can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some cases, a conjugate or a composition of the present disclosure is administered via intravitreal injection. In some cases, a conjugate or a composition of the present disclosure is administered via intraocular administration. In some cases, a conjugate or a composition of the present disclosure is administered via subretinal injection.

A conjugate or a composition of the present disclosure can be utilized in aerosol formulation to be administered via inhalation. A conjugate or a composition of the present disclosure can be formulated into pressurized acceptable propellants such as dichlorodifluoromethane, propane, nitrogen and the like.

Furthermore, a conjugate or a composition of the present disclosure can be made into suppositories by mixing with a variety of bases such as emulsifying bases or water-soluble bases. A conjugate or a composition of the present disclosure can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a conjugate of the present disclosure in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a conjugate of the present disclosure calculated in an amount sufficient to produce the desired effect in association with a pharmaceutically acceptable diluent, carrier or vehicle. The specifications for a conjugate of the present disclosure depend on the particular compound employed and the effect to be achieved, and the pharmacodynamics associated with each compound in the host.

A conjugate or a composition of the present disclosure can be administered as injectables. Injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

A conjugate or a composition of the present disclosure can be formulated in a pharmaceutical composition together with a pharmaceutically acceptable excipient. In some cases, a subject pharmaceutical composition will be suitable for administration to a subject, e.g., will be sterile. For example, in some cases, a subject pharmaceutical composition will be suitable for administration to a human subject, e.g., where the composition is sterile and is free of detectable pyrogens and/or other toxins.

A conjugate or a composition of the present disclosure can be formulated in a pharmaceutical composition that is suitable for administration to the eye of an individual. For example, a conjugate or a composition of the present disclosure can be formulated in a pharmaceutical composition that is suitable for intravitreal administration.

A conjugate or a composition of the present disclosure can be formulated in a pharmaceutical composition together with a pharmaceutically acceptable excipient that increases the in vivo half life of the conjugate. For example, in some cases, a composition of the present disclosure comprises: i) a conjugate or a composition of the present disclosure; and ii) a cyclodextrin.

Suitable cyclodextrins include, e.g., α-cyclodextrin, β-cyclodextrin, γ-cyclodextrin, 2-hydroxypropyl-β-cyclodextrin, hydroxypropyl-γ-cyclodextrin 2,6-di-O-ethyl-β-cyclodextrin, sulfobutylether-β-cyclodextrin, methylated cyclodextrin (e.g., methylated β-cyclodextrin; e.g., β-cyclodextrin with methyl groups on all of the C-2 and C-6 positions, referred to as DIMEB); CRYSMEB; RAMEB; etc.), heptakis-(2,3,6-tri-O-methyl)-β-cyclodextrin (TRIMEB), maltosyl-β-cyclodextrin, and the like. In some cases, a composition of the present disclosure comprises: i) a conjugate or a composition of the present disclosure; and ii) a cyclodextrin. In some cases, a composition of the present disclosure comprises: i) a conjugate or a composition of the present disclosure; and ii) β-cyclodextrin. In some cases, the present disclosure provides methods for administration of an agent intravitreally to a subject in need of the agent by formulating the agent in combination with a cyclodextrin. As demonstrated herein, superior in vivo efficacy and/or persistence of a therapeutic effect can be achieved following intravitreal administration of a conjugate of the present disclosure formulated in conjunction with a cyclodextrin.

In some cases, a composition of the present disclosure comprises: i) a conjugate or a composition of the present disclosure; and ii) an alkyl glycoside. In some cases, the alkyl glycoside is selected from the group consisting of undecyl maltoside, dodecyl maltoside, tridecyl maltoside, tetradecyl maltoside, sucrose mono-dodecanoate, sucrose mono-tridecanoate, and sucrose mono-tetradecanoate.

In some cases, a conjugate or a composition of the present disclosure is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

In some cases, a conjugate or a composition of the present disclosure is present in (e.g., encapsulated within) a micelle (e.g., a nanomicelle), a nanoparticle, or a liposome. For example, in some cases, a conjugate of the present disclosure is present in (e.g., encapsulated within) a nanomicelle that comprises a copolymer of polyhydroxyethylaspartamide (PHEA) and pegylated PHEA. As another example, in some cases, a conjugate of the present disclosure is present in (e.g., encapsulated within) a nanomicelle that comprises a poly(ethylene oxide)-poly(propylene oxide)-poly(ethylene oxide) copolymer. As another example, in some cases, a conjugate of the present disclosure is present in (e.g., encapsulated within) a nanoparticle that comprises one or more of albumin, sodium alginate, chitosan, poly(lactide-co-glycolide) (PLGA), poly(lactic acid) (PLA), and polycaprolactone. As another example, in some cases, a conjugate of the present disclosure is present in (e.g., encapsulated within) a liposome that comprises didodecyldimethylammonium bromide, stearylamine, or N-[1-(2,3-diolcoyloxy)propyl]-N,N,N-trimethylammonium chloride.

Methods

A conjugate of the present disclosure finds use in modulating activity of a target ligand-binding polypeptide. A conjugate of the present disclosure finds use in modulating activity of a cell comprising a conjugate of the present disclosure, where the cell comprises a target ligand-binding polypeptide. The present disclosure thus provides a method of modulating activity of a target ligand-binding polypeptide; and a method of modulating activity of a cell comprising a conjugate of the present disclosure, where the cell comprises a target ligand-binding polypeptide. In some cases, a method of the present disclosure comprises exposing the conjugate (or a cell or tissue comprising the conjugate) to appropriate light conditions such that the ligand binds to the ligand-binding site of the target ligand-binding polypeptide. In some cases, a method of the present disclosure comprises exposing the conjugate (or a cell or tissue comprising the conjugate) to appropriate light conditions such that the ligand does not bind to the ligand-binding site of the target ligand-binding polypeptide.

The present disclosure provides a method of modulating activity of a target ligand-binding polypeptide, the method comprising: a) contacting the target ligand-binding polypeptide with a conjugate of the present disclosure, generating a light-regulatable polypeptide; and b) exposing the light-regulatable polypeptide to light of a wavelength that results in binding of the ligand to the light-regulatable polypeptide, wherein binding of the ligand to the light-regulatable polypeptide modulates activity of the light-regulatable polypeptide. The present disclosure provides a method of modulating activity of a target ligand-binding polypeptide, the method comprising: a) contacting the target ligand-binding polypeptide with a conjugate of the present disclosure, generating a light-regulatable polypeptide; and b) exposing the light-regulatable polypeptide to light of a wavelength that results in release of the ligand from the ligand-binding site of the light-regulatable polypeptide, wherein release of the ligand from the ligand-binding site of the light-regulatable polypeptide modulates activity of the light-regulatable polypeptide.

"Modulating activity" of a target ligand-binding polypeptide (or a light-regulatable polypeptide) includes increasing an activity of the polypeptide; inhibiting an activity of the polypeptide; sensitizing the polypeptide to another (e.g., non-light) stimulus); reducing the sensitivity of the polypeptide to another stimulus; increasing the efficacy by which another stimulus activates the polypeptide; and decreasing the efficacy by which another stimulus activates the polypeptide. The activity depends on the polypeptide being modulated. For example, in some cases, the ligand is an agonist, and binding of the ligand to the target ligand-binding polypeptide (or light-regulatable polypeptide) results in activation of the target ligand-binding polypeptide (or light-regulatable polypeptide). In other instances, the ligand is an antagonist, and binding of the ligand to the target ligand-binding polypeptide (or light-regulatable polypeptide) results in inhibition, desensitization, or inactivation of the target ligand-binding polypeptide (or light-regulatable polypeptide).

Target ligand-binding polypeptides include, but are not limited to, a transcription regulator, an ion channel, a cation channel, a ligand-gated ion channel, a voltage-gated ion channel, a quorum sensor, a pheromone receptor, a neurotransmitter receptor, an enzyme, enzyme, a motor protein, a transporter, a membrane transport protein, a G protein-coupled receptor, a G protein, a receptor tyrosine kinase, a scaffolding protein, an adaptor protein, a cytoskeletal protein, an adhesion protein, a membrane-targeting protein, a protein that direct secretion, and a localization or protein interaction domain of a protein. In some cases, the target ligand-binding polypeptide is a cation channel. In some cases, the target ligand-binding polypeptide is an anion channel. In some cases, the target ligand-binding polypeptide is a potassium channel. In some cases, the target ligand-binding polypeptide is a sodium channel. In some cases, the target ligand-binding polypeptide is a calcium channel.

In some cases, the target ligand-binding polypeptide is in a cell-free composition; i.e., the target ligand-binding polypeptide is not present in a cell.

In some cases, the target ligand-binding polypeptide is present in a cell in vitro. In some cases, the target ligand-binding polypeptide is present in a cell in vivo.

Where the target ligand-binding polypeptide is present in a cell, the cell can be any type of cell. For example, the cell can be a mammalian cell, e.g., a human cell, a non-human primate cell, a rodent cell, and the like. The cell can be a retinal cell, a muscle cell, a neuronal cell, a blood cell (e.g., a nucleated blood cell), an epithelial cell, an endothelial cell, a skin cell, a lung cell, etc.

In some cases, the target ligand-binding polypeptide is present in a cell. In some cases, the cell is a retinal cell. In some cases, the cell is an amacrine cell. In some cases, the cell is a ganglion cell (e.g., a retinal ganglion cell (RGC)). In some cases, the cell is a bipolar cell. In some cases, the cell is a Mueller cell. In some cases, the cell is an ON-bipolar cell (ON-BC). In some cases, the cell is an OFF-bipolar cell.

The present disclosure provides a method of modulating activity of a target cell, the method comprising exposing the target cell to light, where the target cell comprises a conjugate of the present disclosure and a target ligand-binding polypeptide, where the light is of a wavelength that results in binding of the ligand to the target ligand-binding polypeptide, and where binding of the ligand to the target ligand-binding polypeptide modulates activity of the target cell. The present disclosure provides a method of modulating activity of a target cell, the method comprising exposing the target cell to light, where the target cell comprises a conjugate of the present disclosure and a target ligand-binding polypeptide, where the light is of a wavelength that results in release of the ligand from the target ligand-binding polypeptide, and where release of binding of the ligand from the target ligand-binding polypeptide modulates activity of the target cell. In some cases, the cell is a target cell population. In some cases, the target cell or cell population is present in a tissue.

The present disclosure provides a method of introducing sensitivity to light into retinal cells that normally are not directly responsive to light or enhancing the light response of already light-sensitive retinal cells, the method comprising exposing the retinal cell to light, wherein the retinal cell comprises a conjugate of the present disclosure and a target ligand-binding polypeptide, where the light is of a wavelength that results in binding of the ligand to the target ligand-binding polypeptide, and where binding of the ligand to the target ligand-binding polypeptide modulates the activity of the retinal cell in response to light. For example, the target polypeptide in the retinal cell may be a metabotropic glutamate receptor, such as mGluR2 or mGluR8 in amacrine cells or mGluR6 or mGluR7 in bipolar cells or mGluR4 in ganglion cells. In these cases a suitable photo-isomerizable moiety-ligand combination could be azobenzene-glutamate with a D stereoisomer linkage. See, e.g., Broichhagen et al. (2015) *ACS Central Science* 1, 383-393; and Levitz et al. (2017) *Proc. Natl. Acad Sci. USA* 114, E3546-E3554. As other examples, the target polypeptide may be an ionotropic glutamate receptor, such as GluK2, GluK5, GluN2A or GluN2B in bipolar, amacrine or ganglion cells. In these cases, a suitable photo-isomerizable moiety-ligand combination could be azobenzene-glutamate with an L stereoisomer linkage (see, e.g., Volgraf et al. (2006) *Nature Chem. Bio.* 2:47; Volgraf et al. (2007) *J. Am. Chem. Soc.* 129:260; and Berlin et al. (2016) *Elife* 5:e12040), or ATG (see, e.g., Laprell et al. (2015) *Nat. Commun.* 6:8076. As another example, the target polypeptide may be an ionotropic glutamate receptor, such as GluRA1. In this case, a suitable photo-isomerizable moiety-ligand combination could be ShuBQX-3 (see, e.g., Barber et al. (2017) *Chem. Sci.* 8:611). As another example, the target polypeptide may be an ionotropic nicotinic acetylcholine receptor in amacrine or ganglion cells and the ligand may be AC-5, MAACh, HoChPE, MG-624 or MAHoCh (see, e.g., Tochitsky et al. (2012) *Nat. Chem.* 4:105. As another example, the target polypeptide may be an ionotropic GABA-A receptor in amacrine cells or ganglion cells and the ligand may be PAG-2A, PAG-2B, or PAG-3C. As another example, the target polypeptide may be an ionotropic P2X receptor in ganglion cells and the ligand may be MEA-TMA (see, e.g., Lemoine et al. (2013) *Proc. Natl. Acad Sci. USA* 110:20813.

The present disclosure provides method of treating an ocular disorder characterized by reduced responsiveness to light, the method comprising administering a conjugate of the present disclosure, or a composition (e.g., a pharmaceutical composition) comprising a conjugate of the present disclosure, to an eye of an individual having the ocular disorder. In some cases, the conjugate, or a composition (e.g., a pharmaceutical composition) comprising the conjugate, is administered to the individual via intravitreal injection. In some cases, the conjugate, or a composition (e.g., a pharmaceutical composition) comprising the conjugate, is administered to the individual via intraocular administration. In some cases, the conjugate, or a composition (e.g., a pharmaceutical composition) comprising the conjugate, is administered to the individual via subretinal injection.

Ocular disorders characterized by reduced responsiveness to light include, but are not limited to, inherited retinal degenerative diseases such as retinitis pigmentosa and age-related macular degeneration. Ocular disorders that are suitable for treatment with a method of the present disclosure include, but are not limited to, retinitis pigmentosa, macular degeneration, retinoschisis, and Leber's Congenital Amaurosis, and diabetic retinopathy.

Methods for Enhancing Visual Function

The present disclosure provides methods for enhancing or restoring visual function in an eye of an individual. The methods comprise administering an effective amount of a conjugate or a composition of the present disclosure to an eye of the individual.

Administration of a conjugate or a composition of the present disclosure to an eye of an individual can provide for patterned vision and image recognition by the individual. Image recognition can be of a static image and/or of a moving image.

In some cases, administering an effective amount of a conjugate or a composition of the present disclosure to an eye of an individual provides for image recognition at a light intensity of from about $10^{-5}$ W/cm$^2$ to about 10 W/cm$^2$. In some cases, administering an effective amount of a conjugate or a composition of the present disclosure to an eye of an individual provides for image recognition at a light intensity of less than 5 W/cm$^2$, e.g., less than 3 W/cm$^2$, less than 2 W/cm$^2$, or less than 1 W/cm$^2$. For example, administering an effective amount of a conjugate or a composition of the present disclosure to an eye of an individual provides for image recognition at a light intensity of from about to about $10^{-5}$ W/cm$^2$ to about $10^{-1}$ W/cm$^2$, from about $10^{-4}$ W/cm$^2$ to about $10^{-2}$ W/cm$^2$, from about $10^{-4}$ W/cm$^2$ to about 1 W/cm$^2$, from about $10^{-4}$ W/cm$^2$ to about $10^{-1}$ W/cm$^2$, or from about $10^{-4}$ W/cm$^2$ to about $5 \times 10^{-1}$ W/cm$^2$. In some cases, administering an effective amount of a conjugate or a composition of the present disclosure to an eye of an individual provides for image recognition at a light intensity of from about $10^{-5}$ W/cm$^2$ to about $10^{-4}$ W/cm$^2$, from about $10^{-4}$ W/cm$^2$ to about $10^{-3}$ W/cm$^2$, from about $10^{-3}$ W/cm$^2$ to about $10^{-2}$ W/cm$^2$, from about $10^{-2}$ W/cm$^2$ to about $10^{-1}$ W/cm$^2$, or from about $10^{-1}$ W/cm$^2$ to about 1 W/cm$^2$.

In some cases, a conjugate of the present disclosure comprises "460 azobenzene" as discussed above. In some cases, a conjugate of the present disclosure that comprises "460 azobenzene" provides for "off" kinetics that are at least 10-fold, at least 25-fold, at least 50-fold, at least 100-fold, at least 500-fold, at least 1,000-fold, at least 2,000-fold, at least 3,000-fold, at least 4,000-fold, at least 5,000-fold, at least 7,500-fold, at least 10,000-fold, or more than 10,000-fold, faster than the "off" kinetics conferred on a retinal cell by a conjugate that comprises "azobenzene 380." "Off" kinetics refers to the kinetics of turning off the light response upon removal of light (in the dark). For example, in some cases, a conjugate of the present disclosure that comprises "460 azobenzene" provides for "off" kinetics of less than 10 seconds, less than 5 seconds, less than 1 second, less than 900 milliseconds (ms), less than 800 ms, less than 700 ms, less than 600 ms, less than 500 ms, or less than 400 milliseconds. In some cases, a conjugate of the present disclosure that comprises "460 azobenzene" provides for "off" kinetics of from about 100 ms to about 200 ms, from about 200 ms to about 300 ms, from about 300 ms to about 400 ms, from about 400 ms to about 500 ms, from about 500 ms to about 600 ms, from about 600 ms to about 700 ms, from about 700 ms to about 800 ms, from about 800 ms to about 900 ms, from about 900 ms to about 1 second, from about 1 second to about 5 seconds, or from about 5 seconds to about 10 seconds.

In some cases, a conjugate of the present disclosure comprises "460 azobenzene" as discussed above. A conjugate of the present disclosure that comprises "460 azobenzene" provides for excitation by visible light (e.g., blue light). Thus, administration to an eye of a conjugate of the present disclosure that comprises "460 azobenzene" provides for responsiveness of the eye to visible light.

A conjugate or a composition of the present disclosure is administered in an amount effective to increase visual function in an individual by at least 10%, at least 15%, at least 20%, at least 25%, at least 30%, at least 40%, at least 50%, at least 2-fold, at least 5-fold, at least 10-fold, or more than 10-fold, compared with the visual function before administration of the conjugate. Tests for visual function are known in the art, and any known test can be applied to assess visual function.

In some cases, a conjugate of the present disclosure provides for visual detection of a moving image when the image is moving at a speed greater than about 4 centimeters/second (cm/s), greater than about 5 cm/s, greater than about 6 cm/s, greater than about 7 cm/s, or greater than about 8 cm/s. In some cases, a conjugate of the present disclosure provides for visual detection of a moving image when the image is moving at a speed of greater than 8 cm/s, e.g., from 8 cm/s to about 9 cm/s, from 9 cm/s to 10 cm/s, from 10 cm/s to 12 cm/s, from 12 cm/s to 14 cm/s, or from 14 cm/s to about 16 cm/s.

In some cases, a conjugate of the present disclosure is the conjugate referred to in the Examples (and depicted in FIG. 1J and FIG. 4A) as $^{4\times}BGAG_{12,460}$. The $^{4\times}BGAG_{12,460}$ conjugate can provide for enhanced visual function. The $^{4\times}BGAG_{12,460}$ conjugate can provide for patterned vision and image recognition. Image recognition can be of a static image and/or of a moving image. In some cases, the $^{4\times}BGAG_{12,460}$ conjugate provides for visual detection of a moving image when the image is moving at a speed greater than about 4 centimeters/second (cm/s), greater than about 5 cm/s, greater than about 6 cm/s, greater than about 7 cm/s, or greater than about 8 cm/s. In some cases, the $^{4\times}BGAG_{12,460}$ conjugate provides for visual detection of a moving image when the image is moving at a speed of greater than 8 cm/s, e.g., from 8 cm/s to about 9 cm/s, from 9 cm/s to 10 cm/s, from 10 cm/s to 12 cm/s, from 12 cm/s to 14 cm/s, or from 14 cm/s to about 16 cm/s. In some cases, the $^{4\times}BGAG_{12,460}$ conjugate provides for from 100- to 250-fold greater light sensitivity than monovalent $BGAG_{12,460}$.

In some cases, a conjugate of the present disclosure, or a composition (e.g., a pharmaceutical composition) comprising the conjugate, is administered to the individual via intravitreal injection. In some cases, the conjugate, or a composition (e.g., a pharmaceutical composition) comprising the conjugate, is administered to the individual via intraocular administration. In some cases, the conjugate, or a composition (e.g., a pharmaceutical composition) comprising the conjugate, is administered to the individual via subretinal injection.

In some cases, multiple doses of a conjugate or a composition of the present disclosure are administered to an individual. The frequency of administration can vary depending on any of a variety of factors, e.g., severity of the symptoms, etc. For example, in some cases, a conjugate or a composition of the present disclosure is administered once every 6 weeks, once every 5 weeks, once per month, once every 4 weeks, twice per month, three times per month, every other week (qow), once per week (qw), twice per week (biw), three times per week (tiw), four times per week, five times per week, six times per week, every other day (qod), daily (qd), twice a day (qid), or three times a day (tid).

A conjugate or a composition of the present disclosure can be administered to an individual over a period of time of from about 1 day to about 1 year or more than 1 year. For example, a conjugate of the present disclosure can be administered to an individual for a period of time of from 1 week to 2 weeks, from 2 weeks to 1 month, from 1 month to 4 months, from 4 months to 6 months, from 6 months to 1 year, or more than 1 year.

Individuals suitable for treatment with a method of the present disclosure include individuals having reduced visual function due to loss of rod and cone photoreceptors. In some cases, the individual has an inherited retinal degenerative disease such as retinitis pigmentosa, retinoschisis, or Leber's Congenital Amaurosis. In some cases, the individual has an ocular disease (e.g., an inherited ocular disease) selected from retinitis pigmentosa, macular degeneration, age-related macular degeneration, retinoschisis, and Leber's Congenital Amaurosis, and diabetic retinopathy. Individuals suitable for treatment with a method of the present disclosure include individuals having a retinal degeneration condition in which the natural light sensitivity is lost and vision is therefore compromised, but where neurons late in the retinal circuit (e.g. bipolar cells or amacrine interneurons or ganglion cells that output to the brain) are spared and can be made directly sensitive to light by introduction of the cone opsin(s).

Individuals suitable for treatment with a method of the present disclosure include individuals having retinal damage that is traumatic or acute, with no genetic or inherited basis. For example, in some cases, the individual has experienced retinal detachment resulting from blunt trauma, such as a blast injury (e.g., in a military battle), or resulting from an impact to the head, e.g., in the course of an auto accident or other accident resulting in impact to the head. In some instances, the photoreceptors are lost due to traumatic detachment of the retina from the underlying RPE, but the inner retinal neurons are intact. Individuals suitable for treatment with a method of the present disclosure include individuals having photoreceptor loss due to acute light damage, laser exposure, or chemical toxicity.

Devices

The present disclosure provides a device comprising a conjugate or a composition of the present disclosure.

A device of the present disclosure can comprise: a) a container comprising a composition of the present disclosure (a composition comprising a conjugate of the present disclosure); and b) a means for introducing the composition into the eye of an individual. In some cases, the means for introducing the composition into the eye of an individual comprises a needle. In some cases, the container comprises a syringe. The device will in some cases be sterile. In some cases, the device is implantable.

Examples of Non-Limiting Aspects of the Disclosure

Aspects Set A

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A conjugate comprising:
a) an affinity agent that specifically binds:
i) a target ligand-binding polypeptide; or
ii) a polypeptide that binds to a target ligand-binding polypeptide;
b) a branched linker; and
c) two or more photoisomerizable regulators, each independently comprising:
i) a photoisomerizable group; and
ii) a ligand that binds to the target ligand-binding polypeptide.

Aspect 2. The conjugate of aspect 1, wherein the affinity agent comprises benzylguanine.

Aspect 3. The conjugate of aspect 1, wherein the affinity agent comprises chloroalkane.

Aspect 4. The conjugate of aspect 1, wherein the affinity agent comprises benzylcytosine.

Aspect 5. The conjugate of aspect 1, wherein the affinity agent comprises an antibody.

Aspect 6. The conjugate of aspect 1, wherein the affinity agent comprises an aptamer.

Aspect 7. The conjugate of aspect 1, wherein the affinity agent comprises a small molecule or a peptide.

Aspect 8. The conjugate of any one of aspects 1-7, wherein the branched linker comprises two or more arms, each independently comprising a photoisomerizable regulator.

Aspect 9. The conjugate of aspect 8, wherein the branched linker comprises two arms.

Aspect 10. The conjugate of aspect 8, wherein the branched linker comprises four arms.

Aspect 11. The conjugate of any one of aspects 1-10, wherein the branched linker comprises a moiety of formula (BL):

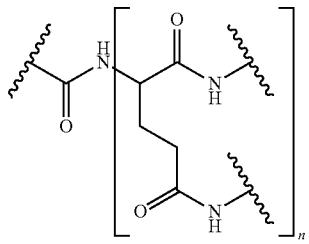

wherein n is an integer from 1 to 10.
Aspect 12. The conjugate of aspect 11, wherein n is 1.
Aspect 13. The conjugate of aspect 11, wherein n is 3.

Aspect 14. The conjugate of any one of aspects 1-13, wherein the photoisomerizable group comprises a moiety selected from an azobenzene, a cyclic azobenzene, an azo-heteroarene, a fulgide, a spiropyran, a triphenyl methane, a thioindigo, a diarylethene, and an overcrowded alkene.

Aspect 15. The conjugate of aspect 14, wherein the photoisomerizable group comprises an azobenzene.

Aspect 16. The conjugate of any one of aspects 1-15, wherein the ligand is an agonist, an antagonist, an allosteric modulator, or a blocker.

Aspect 17. The conjugate of any one of aspects 1-16, wherein the target ligand-binding polypeptide is selected from a transcription regulator, an ion channel, a cation channel, a ligand-gated ion channel, a voltage-gated ion channel, a quorum sensor, a pheromone receptor, a neurotransmitter receptor, a G-protein-coupled receptor, and an enzyme.

Aspect 18. The conjugate of aspect 17, wherein the cation channel is a potassium channel, a sodium channel, or a calcium channel.

Aspect 19. The conjugate of any one of aspects 1-16, wherein the target ligand-binding polypeptide is a glutamate receptor, a metabotropic glutamate receptor, an ionotropic glutamate receptor, an ionotropic nicotinic acetylcholine receptor, an ionotropic GABA-A receptor, a metabotropic GABA-B receptor, a metabotropic dopamine receptor, an ionotropic purinergic P2X receptor, a metabotropic purinergic P2Y receptor, a metabotropic serotonin receptor, an ionotropic serotonin receptor, an ionotropic glycine receptor, a cation channel, a potassium channel, a calcium channel, a sodium channel, a proton channel, an anion channel, or a chloride channel.

Aspect 20. A system comprising:
a) a conjugate according to any one of aspects 1-19;
b) a fusion polypeptide comprising:
i) a target ligand-binding polypeptide that comprises a binding site for the ligand present in the conjugate; and
ii) a heterologous fusion partner that binds the affinity agent.

Aspect 21. The system of aspect 20, wherein the heterologous fusion partner comprises an amino acid sequence having at least 80% amino acid sequence identity to the SNAP polypeptide amino acid sequence set forth in SEQ ID NOT.

Aspect 22. The system of aspect 20, wherein the heterologous fusion partner comprises an amino acid sequence having at least 80% amino acid sequence identity to the CLIP polypeptide amino acid sequence set forth in SEQ ID NO:2.

Aspect 23. The system of aspect 20, wherein the heterologous fusion partner comprises an amino acid sequence having at least 80% amino acid sequence identity to the HALO polypeptide amino acid sequence set forth in SEQ ID NOT.

Aspect 24. A system comprising:
a) a conjugate according to any one of aspects 1-19;
b) nucleic acid comprising a nucleotide sequence encoding a fusion polypeptide comprising:
i) a target ligand-binding polypeptide that comprises a binding site for the ligand; and
ii) a heterologous fusion partner that binds the affinity agent.

Aspect 25. The system of aspect 24, wherein the heterologous fusion partner comprises an amino acid sequence having at least 80% amino acid sequence identity to the SNAP polypeptide amino acid sequence set forth in SEQ ID NOT.

Aspect 26. The system of aspect 24, wherein the heterologous fusion partner comprises an amino acid sequence having at least 80% amino acid sequence identity to the HALO polypeptide amino acid sequence set forth in SEQ ID NOT.

Aspect 27. The system of aspect 24, wherein the heterologous fusion partner comprises an amino acid sequence having at least 80% amino acid sequence identity to the CLIP polypeptide amino acid sequence set forth in SEQ ID NOT.

Aspect 28. The system of any one of aspects 24-27, wherein the nucleic acid is present in a recombinant adenovirus-associated virus (AAV) virion.

Aspect 29. The system of aspect 28, wherein the AAV virion comprises a variant capsid polypeptide that provides for increased infectivity of a retinal cell by the AAV virion, compared to an AAV virion comprising a corresponding wild-type capsid polypeptide.

Aspect 30. A system comprising:
a) a conjugate according to any one of aspects 1-19;
b) a first fusion polypeptide comprising:
  i) a target ligand-binding polypeptide that comprises a binding site for the ligand; and
  ii) a heterologous polypeptide; and
c) a second fusion polypeptide comprising:
  i) an antibody that binds the heterologous polypeptide; and
  ii) a heterologous fusion partner that binds the affinity agent.

Aspect 31. The system of aspect 30, wherein the heterologous fusion partner that binds the affinity agent comprises an amino acid sequence having at least 80% amino acid sequence identity to the SNAP polypeptide amino acid sequence set forth in SEQ ID NO:1.

Aspect 32. The system of aspect 30, wherein the heterologous fusion partner that binds the affinity agent comprises an amino acid sequence having at least 80% amino acid sequence identity to the HALO polypeptide amino acid sequence set forth in SEQ ID NO:3.

Aspect 33. The system of aspect 30, wherein the heterologous fusion partner that binds the affinity agent comprises an amino acid sequence having at least 80% amino acid sequence identity to the CLIP polypeptide amino acid sequence set forth in SEQ ID NO:2.

Aspect 34. The system of any one of aspects 30-33, wherein the antibody is a single-chain Fv or a nanobody.

Aspect 35. The system of any one of aspects 30-34, wherein heterologous polypeptide is an epitope tag.

Aspect 36. A system comprising:
a) a conjugate according to any one of aspects 1-19;
b) a fusion polypeptide comprising:
  i) an antibody that binds specifically to the target ligand-binding polypeptide; and
  ii) a polypeptide that binds to the affinity agent, wherein the polypeptide is selected from a SNAP polypeptide, a HALO polypeptide, and a CLIP polypeptide.

Aspect 37. A method of modulating activity of a target polypeptide, the method comprising:
a) contacting the target polypeptide with the conjugate of any one of aspects 1-19, generating a light-regulatable polypeptide; and
b) exposing the light-regulatable polypeptide to light of a wavelength that results in binding of the ligand to the light-regulatable polypeptide, wherein binding of the ligand to the light-regulatable polypeptide modulates activity of the light-regulatable polypeptide.

Aspect 38. The method of aspect 37, wherein the ligand is an agonist, and wherein binding of the ligand to the light-regulatable polypeptide results in activation of the light-regulatable polypeptide.

Aspect 39. The method of aspect 37, wherein the ligand is an antagonist, and wherein binding of the ligand to the light-regulatable polypeptide results in inhibition, desensitization, or inactivation of the light-regulatable polypeptide.

Aspect 40. The method of any one of aspects 37-39, wherein the target polypeptide is selected from a transcription regulator, an ion channel, a cation channel, a ligand-gated ion channel, a voltage-gated ion channel, a quorum sensor, a pheromone receptor, a neurotransmitter receptor, an enzyme, enzyme, a motor protein, a transporter, a membrane transport protein, a G protein-coupled receptor, a G protein, a receptor tyrosine kinase, a scaffolding protein, an adaptor protein, a cytoskeletal protein, an adhesion protein, a membrane-targeting protein, a protein that direct secretion, and a localization or protein interaction domain of a protein.

Aspect 41. The method of aspect 40, wherein the cation channel is a potassium channel, a sodium channel, or a calcium channel.

Aspect 42. The method of any one of aspects 37-41, wherein the target polypeptide is in a cell.

Aspect 43. The method of aspect 42, wherein the cell is in vivo.

Aspect 44. The method of aspect 43, wherein the cell is a retinal cell.

Aspect 45. A method of increasing the sensitivity of a retinal cell to light, the method comprising:
exposing the retinal cell to light, wherein the retinal cell comprises the conjugate of any one of aspects 1-19, or the system of any one of aspects 20-36, wherein the light is of a wavelength that results in binding of the ligand to the light-regulatable polypeptide, and wherein binding of the ligand to the light-regulatable polypeptide increases the sensitivity of the retinal cell to light.

Aspect 46. A method of conferring light responsiveness on a retinal cell, the method comprising introducing into the retinal cell the conjugate of any one of aspects 1-19 or the system of any one of aspects 20-36.

Aspect 47. A method of treating an ocular disorder characterized by reduced responsiveness to light, the method comprising administering the conjugate of any one of aspects 1-19 or the system of any one of aspects 20-36 to an eye of an individual having the ocular disorder.

Aspect 48. The method of aspect 47, wherein the ocular disorder is an inherited retinal degenerative disease.

Aspect 49. The method of aspect 48, wherein the disease is retinitis pigmentosa or age-related macular degeneration.

Aspect 50. A composition comprising:
a) a conjugate according to any one of aspects 1-19; and
b) a pharmaceutically acceptable excipient.

Aspect 51. The composition of aspect 50, wherein the composition is sterile and free of pyrogens.

Aspect 52. The composition of aspect 50 or aspect 51, wherein the pharmaceutically acceptable excipient comprises a cyclodextrin.

Aspect 53. The composition of aspect 52, wherein the cyclodextrin is α-cyclodextrin, β-cyclodextrin, γ-cyclodextrin, or a derivatized cyclodextrin.

Aspect 54. The composition of any one of aspects 50-53, wherein the conjugate is encapsulated within a nanoparticle.

Aspect 55. The composition of aspect 54, wherein the nanoparticle is a nanomicelle, a liposome, a nanosphere, or a nanocapsule.

Aspect 56. A medical device comprising:
a) a container comprising a composition according to any one of aspects 50-55; and
b) a means for introducing the composition into the eye of an individual.

Aspect 57. The device of aspect 56, wherein the means for introducing the composition into the eye of an individual comprises a needle.

Aspect 58. The device of aspect 56 or aspect 57, wherein the container comprises a syringe.

Aspect 59. The device of any one of aspects 56-58, wherein the device is sterile.

Aspect 60. A conjugate comprising:
a) an affinity agent;
b) a branched linker; and
c) two or more photoisomerizable regulators, each independently comprising:
i) a photoisomerizable group; and
ii) a label, a reactive group, or a second affinity agent.

Aspects Set B

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A composition for intraocular administration, the composition comprising:
A) a conjugate comprising:
a) an affinity agent that specifically binds:
i) a target ligand-binding polypeptide; or
ii) a polypeptide that binds to a target ligand-binding polypeptide;
b) a branched linker; and
c) two or more photoisomerizable regulators, each independently comprising:
i) a photoisomerizable group; and
ii) a ligand that binds to the target ligand-binding polypeptide; and
B) a pharmaceutically acceptable excipient suitable for intraocular administration.

Aspect 2. The composition of aspect 1, wherein the affinity agent comprises benzylguanine.

Aspect 3. The composition of aspect 1, wherein the affinity agent comprises chloroalkane.

Aspect 4. The composition of aspect 1, wherein the affinity agent comprises benzylcytosine.

Aspect 5. The composition of aspect 1, wherein the affinity agent comprises an antibody.

Aspect 6. The composition of aspect 1, wherein the affinity agent comprises an aptamer.

Aspect 7. The composition of aspect 1, wherein the affinity agent comprises a small molecule or a peptide.

Aspect 8. The composition of any one of aspects 1-7, wherein the branched linker comprises two or more arms, each independently comprising a photoisomerizable regulator.

Aspect 9. The composition of aspect 8, wherein the branched linker comprises two arms.

Aspect 10. The composition of aspect 8, wherein the branched linker comprises four arms.

Aspect 11. The composition of any one of aspects 1-10, wherein the branched linker comprises a moiety of formula (BL):

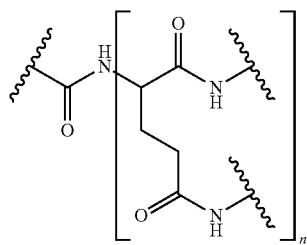

wherein n is an integer from 1 to 10.

Aspect 12. The composition of aspect 11, wherein n is 1.

Aspect 13. The composition of aspect 11, wherein n is 3.

Aspect 14. The composition of any one of aspects 1-13, wherein the photoisomerizable group comprises a moiety selected from an azobenzene, a cyclic azobenzene, an azoheteroarene, a fulgide, a spiropyran, a triphenyl methane, a thioindigo, a diarylethene, and an overcrowded alkene.

Aspect 15. The composition of aspect 14, wherein the photoisomerizable group comprises an azobenzene.

Aspect 16. The composition of any one of aspects 1-15, wherein the ligand is an agonist, an antagonist, an allosteric modulator, or a blocker.

Aspect 17. The composition of any one of aspects 1-16, wherein the target ligand-binding polypeptide is selected from a transcription regulator, an ion channel, a cation channel, a ligand-gated ion channel, a voltage-gated ion channel, a quorum sensor, a pheromone receptor, a neurotransmitter receptor, a G-protein-coupled receptor, and an enzyme.

Aspect 18. The composition of aspect 17, wherein the cation channel is a potassium channel, a sodium channel, or a calcium channel.

Aspect 19. The composition of any one of aspects 1-16, wherein the target ligand-binding polypeptide is a glutamate receptor, a metabotropic glutamate receptor, an ionotropic glutamate receptor, an ionotropic nicotinic acetylcholine receptor, an ionotropic GABA-A receptor, a metabotropic GABA-B receptor, a metabotropic dopamine receptor, an ionotropic purinergic P2X receptor, a metabotropic purinergic P2Y receptor, a metabotropic serotonin receptor, an ionotropic serotonin receptor, an ionotropic glycine receptor, a cation channel, a potassium channel, a calcium channel, a sodium channel, a proton channel, an anion channel, or a chloride channel.

Aspect 20. The composition of any one of aspects 1-19, wherein the photoisomerizable group comprises an azobenzene that isomerizes in response to visible light.

Aspect 21. The composition of any one of aspects 1-20, wherein the ligand is glutamate.

Aspect 22. The composition of aspect 5, wherein the antibody is a single-chain Fv (scFv) or a nanobody.

Aspect 23. The composition of aspect 22, wherein the antibody is specific for a metabotropic glutamate receptor (mGluR), optionally wherein the mGluR is mGluR2, mGluR3, mGluR4, mGluR5, or mGluR6.

Aspect 24. The composition of any one of aspects 1-23, wherein the composition is sterile and free of pyrogens.

Aspect 25. The composition of any one of aspects 1-24, wherein the pharmaceutically acceptable excipient comprises a cyclodextrin.

Aspect 26. The composition of aspect 25, wherein the cyclodextrin is α-cyclodextrin, β-cyclodextrin, γ-cyclodextrin, hydroxypropyl-β-cyclodextrin, sulfobutylether-β-cyclodextrin, or a derivatized cyclodextrin.

Aspect 27. The composition of any one of aspects 1-26, wherein the conjugate is encapsulated within a nanoparticle.

Aspect 28. The composition of aspect 54, wherein the nanoparticle is a nanomicelle, a liposome, a nanosphere, or a nanocapsule.

Aspect 29. A composition for intraocular administration, the composition comprising:
  A) a system comprising:
  a) a conjugate as recited in any one of aspects 1-23;
  b) a fusion polypeptide comprising:
    i) a target ligand-binding polypeptide that comprises a binding site for the ligand present in the conjugate; and
    ii) a heterologous fusion partner that binds the affinity agent; and
  B) a pharmaceutically acceptable excipient suitable for intraocular administration.

Aspect 30. The composition of aspect 29, wherein the heterologous fusion partner comprises an amino acid sequence having at least 80% amino acid sequence identity to the SNAP polypeptide amino acid sequence set forth in SEQ ID NOG or SEQ ID NOG.

Aspect 31. The composition of claim 29, wherein the heterologous fusion partner comprises an amino acid sequence having at least 80% amino acid sequence identity to the CLIP polypeptide amino acid sequence set forth in SEQ ID NO:2.

Aspect 32. The composition of claim 29, wherein the heterologous fusion partner comprises an amino acid sequence having at least 80% amino acid sequence identity to the HALO polypeptide amino acid sequence set forth in SEQ ID NO:3.

Aspect 33. A composition for intraocular administration, the composition comprising:
  A) a system comprising:
  a) a conjugate as recited in any one of claims 1-23;
  b) nucleic acid comprising a nucleotide sequence encoding a fusion polypeptide comprising:
    i) a target ligand-binding polypeptide that comprises a binding site for the ligand; and
    ii) a heterologous fusion partner that binds the affinity agent; and
  B) a pharmaceutically acceptable excipient suitable for intraocular administration.

Aspect 34. The composition of claim 33, wherein the heterologous fusion partner comprises an amino acid sequence having at least 80% amino acid sequence identity to the SNAP polypeptide amino acid sequence set forth in SEQ ID NO:1 or SEQ ID NO:4.

Aspect 35. The composition of claim 33, wherein the heterologous fusion partner comprises an amino acid sequence having at least 80% amino acid sequence identity to the HALO polypeptide amino acid sequence set forth in SEQ ID NO:3.

Aspect 36. The composition of claim 33, wherein the heterologous fusion partner comprises an amino acid sequence having at least 80% amino acid sequence identity to the CLIP polypeptide amino acid sequence set forth in SEQ ID NO:2.

Aspect 37. The composition of any one of claims 33-36, wherein the nucleic acid is present in a recombinant adenovirus-associated virus (AAV) virion.

Aspect 38. The composition of claim 32, wherein the AAV virion comprises a variant capsid polypeptide that provides for increased infectivity of a retinal cell by the AAV virion, compared to an AAV virion comprising a corresponding wild-type capsid polypeptide.

Aspect 39. A composition for intraocular administration, the composition comprising:
  A) a system comprising:
  a) a conjugate as recited in any one of aspects 1-23;
  b) a first fusion polypeptide comprising:
    i) a target ligand-binding polypeptide that comprises a binding site for the ligand; and
    ii) a heterologous polypeptide; and
  c) a second fusion polypeptide comprising:
    i) an antibody that binds the heterologous polypeptide; and
    ii) a heterologous fusion partner that binds the affinity agent; and
  B) a pharmaceutically acceptable excipient suitable for intraocular administration.

Aspect 40. The composition of aspect 39, wherein the heterologous fusion partner that binds the affinity agent comprises an amino acid sequence having at least 80% amino acid sequence identity to the SNAP polypeptide amino acid sequence set forth in SEQ ID NO:1 or SEQ ID NO:4.

Aspect 41. The composition of aspect 39, wherein the heterologous fusion partner that binds the affinity agent comprises an amino acid sequence having at least 80% amino acid sequence identity to the HALO polypeptide amino acid sequence set forth in SEQ ID NO:3.

Aspect 42. The composition of aspect 39, wherein the heterologous fusion partner that binds the affinity agent comprises an amino acid sequence having at least 80% amino acid sequence identity to the CLIP polypeptide amino acid sequence set forth in SEQ ID NO:2.

Aspect 43. The composition of any one of aspects 39-42, wherein the antibody is a single-chain Fv or a nanobody.

Aspect 44. The composition of any one of aspects 39-43, wherein heterologous polypeptide is an epitope tag.

Aspect 45. A composition for intraocular administration, the composition comprising:
  A) a system comprising:
  a) a conjugate as recited in any one of aspects 1-23;
  b) a fusion polypeptide comprising:
    i) an antibody that binds specifically to the target ligand-binding polypeptide; and
    ii) a polypeptide that binds to the affinity agent, wherein the polypeptide is selected from a SNAP polypeptide, a HALO polypeptide, and a CLIP polypeptide; and
  B) a pharmaceutically acceptable excipient suitable for intraocular administration.

Aspect 46. A method of increasing the sensitivity of a retinal cell to light, the method comprising:
  exposing the retinal cell to light, wherein the retinal cell comprises a conjugate as recited in any one of aspects 1-23, or the system as recited in any one of aspects 29-45, wherein the light is of a wavelength that results in binding of the ligand to the light-regulatable polypeptide, and wherein binding of the ligand to the light-regulatable polypeptide increases the sensitivity of the retinal cell to light.

Aspect 47. A method of conferring light responsiveness on a retinal cell, the method comprising introducing into the retinal cell a conjugate as recited in any one of aspects 1-23, or the system of any one of aspects 29-45.

Aspect 48. A method of treating an ocular disorder characterized by reduced responsiveness to light, the method comprising administering a composition according to any one of aspects 1-29, or a composition according to any one of aspects 29-45, to an eye of an individual having the ocular disorder.

Aspect 49. The method of aspect 48, wherein the ocular disorder is an inherited retinal degenerative disease.

Aspect 50. The method of aspect 49, wherein the disease is retinitis pigmentosa or age-related macular degeneration.

Aspect 51. A medical device comprising:
a) a container comprising a composition according to any one of aspects 1-29, or a composition according to any one of aspects 29-45; and
b) a means for introducing the composition into the eye of an individual.

Aspect 52. The device of aspect 51, wherein the means for introducing the composition into the eye of an individual comprises a needle.

Aspect 53. The device of aspect 51 or aspect 52, wherein the container comprises a syringe.

Aspect 54. The device of any one of aspects 51-53, wherein the device is sterile.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pi, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Preparation of 2×BGAG and 4×BGAG

Materials and Methods

General Chemical Methods

All reactions are outlined in Scheme S1-S11 in FIG. 1A-1K.

Solvents for chromatography and reactions were purchased dry over molecular sieves or in HPLC grade. Unless otherwise stated, all other reagents were used without further purification from commercial sources. LC-MS was performed on a Shimadzu MS2020 connected to a Nexera UHPLC system equipped with a Waters ACQUITY UPLC BEH C18 (1.7 µm, 50×2.1 mm). Buffer A: 0.1% FA in $H_2O$ Buffer B: acetonitrile. The typical gradient was from 10% B for 0.5 min→gradient to 90% B over 4.5 min→90% B for 0.5 min→gradient to 99% B over 0.5 min with 1 mL/min flow.

High resolution mass spectrometry (HRMS) was performed using a Bruker maXis II ETD hyphenated with a Shimadzu Nexera system. The instruments were controlled via Brukers otofControl 4.1 and Hystar 4.1 SR2 (4.1.31.1) software. The acquisition rate was set to 3 Hz and the following source parameters were used for positive mode electrospray ionization: End plate offset=500 V; capillary voltage=3800 V; nebulizer gas pressure=45 psi; dry gas flow=10 L/min; dry temperature=250° C. Transfer, quadrupole and collision cell settings are mass range dependent and were fine-adjusted with consideration of the respective analyte's molecular weight. For internal calibration sodium format clusters were used. Samples were desalted via fast liquid chromatography. A Supelco Titan™ C18 UHPLC Column, 1.9 µm, 80 Å pore size, 20×2.1 mm and a 2 min gradient from 10 to 98% aqueous MeCN with 0.1% FA ($H_2O$: Carl Roth GmbH+Co. KG ROTISOLV® Ultra LC-MS; MeCN: Merck KGaA LiChrosolv® Acetonitrile hypergrade for LC-MS; FA—Merck KGaA LiChropur® Formic acid 98%-100% for LC-MS) was used for separation. Sample dilution in 10% aqueous ACN (hyper grade) and injection volumes were chosen dependent of the analyte's ionization efficiency. Hence, on-column loadings resulted between 0.25-5.0 ng. Automated internal re-calibration and data analysis of the recorded spectra were performed with Bruker's DataAnalysis 4.4 SR1 software.

Preparative RP-HPLC was performed on a Waters e2695 system equipped with a 2998 PDA detector for product collection (at 220, 280, 360 or 460 nm) on a Supelco Ascentis® C18 HPLC Column (5 µm, 250×21.2 mm). Buffer A: 0.1% TFA in $H_2O$ Buffer B: acetonitrile. The typical gradient was from 10% B for 5 min→gradient to 90% B over 45 min→90% B for 5 min→gradient to 99% B over 5 min with 8 mL/min flow. Compounds 1, 2, 25 and BG-COOH, BC-DBCO were previously described (Broichhagen et al., 2015; Levitz et al., 2017).

Abbreviations: DIPEA: N,N-diisopropylethylamine; DBU: 1,8-diazabicyclo[5.4.0]undec-7-ene; DMF: N,N-dimethylformamide; DMSO: dimethylsulfoxide; FA: formic acid; Su: succinimidyl; TFA: trifluoroacetic acid; TSTU: O-(A-succinimidyl)-N,N,N',N'-tetramethyluronium tetrafluoroborate.

Notes and observations: NHS ester stability: TSTU was the coupling reagent of choice used for the synthesis of BGAGs, converting an acid to its respective NHS-ester usually within minutes. While most NHS esters were used in situ without purification, they can be isolated by RP-HPFC (cf. compound 4) and immediate lyophilization. Aliquoting and storage at −20° C. is recommended to avoid repeated freeze-thaw cycles that lead to decomposition. Fmoc deprotection: Fmoc is a standard amine protecting group extensively used in solid phase peptide synthesis, where amide couplings (with activating agents in DMF) and subsequent deprotection (with piperidine in DMF) is performed iteratively in high yields. Inspired by this and with the aim to reduce labor and purification steps, peptide couplings were performed in DMF with TSTU as an activating agent, and after amide coupling was complete, 5 vol % of piperidine was added directly to the reaction mixture. This proved to work reliably in our hands with all blue-shifted azobenzene compounds based on structure 1, but lead to complex reaction mixtures when using this method with red-shifted azobenzene compounds based on structure 2. Purified Fmoc-containing compounds by RP-HPFC were used to remove DMF, DIPEA and urea side products from TSTU, and employed DBU in MeCN as a deprotection reagent. Indeed, this was tolerated very well by red-shifted compounds and is noted when used in the procedures below. Stability of BG, BC and Halo-congeners towards acid: BGAGs need final deprotection of the NHBoc group to the free amine and TFA is the deprotecting agent of choice, however, the O-benzylated guanine and cytosine bases were shown to be labile towards strong acids. It was found that TFA can be used with BG-containing compounds if kept on ice with pre-cooled TFA, and its removal is not done in a rotary evaporator but by applying a gentle stream of nitrogen in a well ventilated chemical hood. BC-containing compounds to not survive this treatment unharmed, and this is the reason why the NHBoc group is deprotected beforehand and strain promoted alkyne azide click reaction is performed in another orthogonal way. The Halo-group, however, is inert towards neat TFA at r.t.

General protocol A to generate NHS esters: A 1 mL vial was charged with 1.0 equiv. of acid dissolved in DMF (1 mL/10 mg) and 4.0 equiv. of DIPEA was added before 1.1 equiv. of TSTU in one portion (for amounts<1 mg of TSTU, stock solutions were prepared as it is critical to not overload TSTU). The active NHS ester was allowed to form for 15 min and used without further purification.

General procedure B for peptide couplings and in situ Fmoc deprotection: A 1 mL vial was charged with 1.0 equiv. amine dissolved in DMF (1 mL/10 mg) and 4.0 equiv. DIPEA. The pre-formed NHS ester (section 1.3) was added drop-wise at and the reaction mixture was allowed to stir at r.t. Upon complete conversion according to LCMS (usually <30 min), 5 vol % of piperidine was added to the reaction mixture and the reaction allowed to stir for additional 10 min, before it was quenched by addition of 5 vol % HOAc and 10 vol % water and subjected to RP-HPLC.

General procedure C for peptide couplings for branching: A 1 mL vial was charged with 3.0 equiv. amine dissolved in DMF (1 mL/10 mg) and 8.0 equiv. DIPEA. The bis NHS ester 4 (1.0 equiv.) was dissolved in the same amount of DMF and added slowly and dropwise under vigorous stirring. The order and speed of addition is crucial to afford minimal amounts of side-products (i.e. imids, mono amides of succinates). Upon complete conversion according to LCMS, the reaction was directly deprotected or quenched and subjected to RP-HPLC (see below).

General procedure D for Boc deprotection: A 15 mL falcon tube was charged with Boc protected compound and put in an ice bath. Pre-cooled (4° C.) TFA was added neat. The reaction mixture was vortexed to ensure homogeneity and put back on ice for 15 min before all volatiles were removed under a gentle stream of nitrogen. The residue was taken up in DMF/water (9/1) and subjected to RP-HPLC. NOTE: Azobenzene-containing reaction mixtures turned deep red upon addition of TFA.

Synthesis 5-((2-(2-((6-Chlorohexyl)oxy)ethoxy)ethyl)amino)-5-oxopentanoic acid (Halo-COOH)

A 4 mL dram vial was charged with 100 mg (310 µmol, 1.0 equiv.) HaloNHBoc and 1 mL neat TFA was added. The solution was allowed to stand at r.t. for 5 min before all volatiles were removed under a gentle stream of nitrogen. 1 mL DMF and 160 µL DIPEA were added, before 35.3 mg (310 µmol, 1.0 equiv.) of glutaric anhydride was added in one portion. The reaction mixture was incubated o.n., before it was quenched with 160 µL HOAc, diluted with water and subjected to RP-HPLC to obtain 92 mg (274 µmol) of the desired product as a clear oil after lyophilization in 88% yield. HRMS (ESI): calc, for $C_{15}H_{29}ClNO_5$ $[M+H]^+$: 338.1729, found: 338.1728.

Bis(2,5-dioxopyrrolidin-1-yl) (((9H-fluoren-9-yl)methoxy)carbonyl)-D-glutamate (4)

A 4 mL dram vial was charged with 300 mg (812 µmol, 1.0 equiv.) of (((9H-fluoren-9-yl)methoxy)carbonyl-D-glutamic acid (3) dissolved in 3 mL DMSO and 850 µL DIPEA before 978 mg (3.25 mmol, 4.0 equiv.) TSTU was added in one portion. The reaction mixture was stirred vigorously for 1 h before it was quenched by the addition of 850 µL HOAc and 200 µL water and subjected to preparative RP-HPLC. The desired product was obtained as a white powder after lyophilization in 35% yield (161 mg, 286 µmol). NOTE: Immediate freeze-drying after elution from the HPLC system is highly recommended to suppress hydrolysis. The product was aliquoted to avoid multiple freeze-thaw cycles that also hydrolyzed the NHS esters. HRMS (ESI): calc, for $C_{28}H_{26}N_3O_{10}$ $[M+H]^+$: 564.1613, found: 564.1614.

(2S,2'S,4S,4'S)-4,4'-(((((1E,1'E)-(((2,2'-(((R)-2-Aminopentanedioyl)bis(azanediyl))bis(acetyl))bis(azanediyl))bis(4,1-phenylene))bis(diazene-2,1-diyl))bis(4,1-phenylene))bis(azanediyl))bis(4-oxobutane-4,1-diyl))bis(2-((tert-butoxycarbonyl)amino)pentanedioic acid) (5)

5 was prepared according to general procedure C and was in situ deprotected by addition of 5 vol % of piperidine to the reaction mixture. The reaction allowed to stir for additional 10 min, before it was quenched by addition of 5 vol % HOAc and 10 vol % water and subjected to RP-HPLC. HRMS (ESI): calc, for $C_{61}H_{79}N_{13}O_{18}$ $[M+2H]^{2+}$: 640.7828, found: 640.7835.

(2S,4S)-2-(4-((4-((E)-(4-((R)-1-amino-41-((2-((4-((E)-(4-((5S,7S)-7-((tert-Butoxycarbonyl)amino)-5,7-dicarboxyheptanamido)phenyl)diazenyl)phenyl)amino)-2-oxoethyl)carbamoyl)-39,44-dioxo-3,6,9,12,15,18,21,24,27,30,33,36-dodecaoxa-40,45-diazaheptatetracontan-47-amido)phenyl)diazenyl)phenyl)amino)-4-oxobutyl)-4-((tert-butoxycarbonyl)amino)pentanedioic acid (6)

6 was prepared according to general procedure B with the first step conducted at 50° C. HRMS (ESI): calc, for $C_{88}H_{132}N_{14}O_{31}$ $[M+2H]^{2+}$: 940.4586, found: 940.4582.

(2S,4S)-2-(4-((E)-(4-((R)-1-(4-(((2-Amino-9H-purin-6-yl)oxy)methyl)phenyl)-49-((2-((4-((E)-(4-((5S,7S)-7-((tert-butoxycarbonyl)amino)-5,7-dicarboxyheptanamido)phenyl)diazenyl)phenyl)amino)-2-oxoethyl)carbamoyl)-3,7,47,52-tetraoxo-11,14,17,20,23,26,29,32,35,38,41,44-dodecaoxa-2,8,48,53-tetraazapentapentacontan-55-amido)phenyl)diazenyl)phenyl)amino)-4-oxobutyl)-4-((tert-butoxycarbonyl)amino)pentanedioic acid (7)

7 was prepared according to general procedure B, with BG-COOSu prepared according to general procedure A, without the addition of piperidine. HRMS (ESI): calc. for $C_{106}H_{150}N_{20}O_{34}$ [M+2H]$^{2+}$: 1124.0321, found: 1124.0327.

(2S,4S)-2-Amino-4-((4-((E)-(4-((R)-49-(3-((2-((4-((E)-(4-((5S,7S)-7-amino-5,7-dicarboxyheptanamido)phenyl)diazenyl)phenyl)amino)-2-oxoethyl)amino)-3-oxopropyl)-1-(4-(((2-amino-9H-purin-6-yl)oxy)methyl)phenyl)-3,7,47,50-tetraoxo-11,14,17,20,23,26,29,32,35,38,41,44-dodecaoxa-2,8,48,51-tetraazatripentacontan-53-amido)phenyl)diazenyl)phenyl)amino)-4-oxobutyl)pentanedioic acid ($^{2\times}$BGAG$_{12}$)

$^{2\times}$BGAG$_{12}$ was prepared according to general procedure D. HRMS (ESI): calc. for $C_{96}H_{134}N_{20}O_{30}$ [M+2H]$^{2+}$: 1032.9797, found: 1032.9787.

(2S,2'S,4S,4'S)-4,4'-(((((1E,1'E)-(((2,2'-(((R)-2-(5-((4-(((2-Amino-9H-purin-6-yl)oxy)methyl)benzyl)amino)-5-oxopentanamido)pentanedioyl)bis(azanediyl))bis(acetyl))bis(azanediyl))bis(4,1-phenylene))bis(diazene-2,1-diyl))bis(4,1-phenylene))bis(azanediyl))bis(4-oxobutane-4,1-diyl))bis(2-((tert-butoxycarbonyl)amino)pentanedioic acid) (8)

8 was prepared according to general procedure B, with BG-COOSu prepared according to general procedure A, with the first step conducted at 50° C. and without the addition of piperidine.
HRMS (ESI): calc. for $C_{79}H_{95}N_{19}O_{21}$ [M−2H]$^{2-}$; 821.8402, found: 821.8413.

(2S,2'S, 4S,4'S)-4,4'-(((((1E,1'E)-(((2,2'-(((R)-2-(5-((4-(((2-Amino-9H-purin-6-yl)oxy)methyl)benzyl)amino)-5-oxopentanamido)pentanedioyl)bis(azanediyl))bis(acetyl))bis(azanediyl))bis(4,1-phenylene))bis(diazene-2,1-diyl))bis(4,1-phenylene))bis(azanediyl))bis(4-oxobutane-4,1-diyl)bis(2-aminopentanedioic acid) ($^{2\times}$BGAG$_{0}$)

$^{2\times}$BGAG$_{0}$ was prepared according to general procedure D. HRMS (ESI): calc. for $C_{69}H_{79}N_{19}O_{17}$ [M−2H]$^{2-}$: 721.7878, found: 721.7870.

(2S,4S)-2-(4-((4-((E)-(4-(1-Amino-39-oxo-3,6,9,12,15,18,21,24,27,30,33,36-dodecaoxa-40-azadotetracontan-42-amido)phenyl)diazenyl)phenyl)amino)-4-oxobutyl)-4-((tert-butoxycarbonyl)amino)pentanedioic acid (9)

9 was prepared according to general procedure B. HRMS (ESI): calc. for $C_{55}H_{90}N_7O_{21}$ [M+H]$^+$: 1184.6184, found: 1184.6176.

(2S,2'S,4S,4'S)-4,4'-(((((1E,1'E)-((((R)-45-Amino-4,44,48,88-tetraoxo-7,10,13,16,19,22,25,28,31,34,37,40,52,55,58,61,64,67,70,73,76,79,82,85-tetracosaoxa-3,43,49,89-tetraazahennonacontanedioyl)bis(azanediyl))bis(4,1-phenylene))bis(diazene-2,1-diyl))bis(4,1-phenylene))bis(azanediyl))bis(4-oxobutane-4,1-diyl))bis(2-((tert-butoxycarbonyl)amino)pentanedioic acid) (10)

10 was prepared according to general procedure C and was in situ deprotected by addition of 5 vol % of piperidine to the reaction mixture. The reaction allowed to stir for additional 10 min, before it was quenched by addition of 5 vol % HOAc and 10 vol % water and subjected to RP-HPLC. HRMS (ESI): calc. for $C_{115}H_{186}N_{15}O_{44}$ [M+3H]$^{3+}$: 827.4264, found: 824.4261.

(2S,2'S,4S,4'S)-4,4'-(((((1E,1'E)-((((R)-45-(5-((4-(((2-Amino-9H-purin-6-yl)oxy)methyl)benzyl)amino)-5-oxopentanamido)-4,44,48,88-tetraoxo-7,10,13,16,19,22,25,28,31,34,37,40,52,55,58,61,64,67,70,73,76,79,82,85-tetracosaoxa-3,43,49,89-tetraazahennonacontanedioyl)bis(azanediyl))bis(4,1-phenylene))bis(diazene-2,1-diyl))bis(4,1-phenylene))bis(azanediyl))bis(4-oxobutane-4,1-diyl))bis(2-((tert-butoxycarbonyl)amino)pentanedioic acid) (11)

11 was prepared according to general procedure B, with BG-COOSu prepared according to general procedure A, with the first step conducted at 50° C. and without the addition of piperidine. HRMS (ESI): calc. for $C_{133}H_{204}N_{21}O_{47}$ [M+3H]$^{3+}$: 949.4744, found: 949.4747.

(2S,2'S,4S,4'S)-4,4'-((((1E,1'E)-((((R)-45-(5-((4-(((2-Amino-9H-purin-6-yl)oxy)methyl)benzyl)amino)-5-oxopentanamido)-4,44,48,88-tetraoxo-7,10,13,16,19,22,25,28,31,34,37,40,52,55,58,61,64,67,70,73,76,79,82,85-tetracosaoxa-3,43,49,89-tetraazahennonacontanedioyl)bis(azanediyl))bis(4,1-phenylene))bis(diazene-2,1-diyl))bis(4,1-phenylene))bis(azanediyl))bis(4-oxobutane-4,1-diyl)bis(2-aminopentanedioic acid) ($^{2\times}$BGAG$_{12,\nu2}$)

$^{2\times}$BGAG$_{12,\nu2}$ was prepared according to general procedure D. HRMS (ESI): calc. for $C_{123}H_{188}N_{21}O_{43}$ [M+3H]$^{3+}$: 882.7728, found: 882.7723.

(2S,2'-4S,4'S)-4,4'-(((((1E,1'E)-((((R)-45-amino-4,44,48,88-tetraoxo-7,10,13,16,19,22,25,28,31,34,37,40,52,55,58,61,64,67,70,73,76,79,82,85-tetracosaoxa-3,43,49,89-tetraazahennonacontanedioyl)bis(azanediyl))bis(4,1-phenylene))bis(diazene-2,1-diyl))bis(4,1-phenylene))bis(azanediyl))bis(4-oxobutane-4,1-diyl)bis(2-((tert-butoxycarbonyl)amino)pentanedioic acid) (12)

12 was prepared according to general procedure C and was in situ deprotected by addition of 5 vol % of piperidine to the reaction mixture. The reaction allowed to stir for additional 10 min, before it was quenched by addition of 5 vol % HOAc and 10 vol % water and subjected to RP-HPLC. HRMS (ESI): calc. for $C_{115}H_{186}N_{15}O_{44}$ [M+3H]$^{3+}$: 827.4264, found: 827.4255.

(2S,4S)-2-[3-({4-[(1E)-2-[4-(2-{1-[(4R)-4-[(2R)-2-Amino-4-{[(1R)-1,3-bis[(38-{[({4-[(1E)-2-{4-[(5S,7S)-7-{[(tert-butoxy)carbonyl]amino]-5,7-dicarboxyheptanamido]phenyl}diazen-1-yl]phenyl}carbamoyl)methyl]carbamoyl}-3,6,9,12,15,18,21,24,27,30,33,36-dodecaoxaoctatriacontan-1-yl)carbamoyl]propyl]carbamoyl}butanamido]-4-[(38-{[({4-[(1E)-2-{4-[(5S,7S)-7-{[(tert-butoxy)carbonyl]amino}-5,7-dicarboxyheptanamido]phenyl}diazen-1-yl]phenyl}carbamoyl)methyl]carbamoyl}-3,6,9,12,15,18,21,24,27,30,33,36-dodecaoxaoctatriacontan-1-yl)carbamoyl]butanamido]-3,6,9,12,15,18,21,24,27,30,33,36-dodecaoxanonatriacontan-39-amido}acetamido)phenyl]diazen-1-yl phenyl}carbamoyl)propyl]-4-{[(tert-butoxy)carbonyl]amino}pentanedioic acid (13)

13 was prepared according to general procedure B with the first step conducted at 50° C. HRMS (ESI): calc. for $C_{235}H_{375}N_{31}O_{90}$ [M+4H]$^{4+}$: 1286.3940, found: 1286.3925.

(2S,4S)-2-[3-({4-[(1E)-2-[4-(2-{1-[(4R)-4-[(2R)-2-(4-{[(4-{[(2-Amino-9H-purin-6-yl)oxy]methyl}phenyl)methyl]carbamoyl}butanamido)-4-{[(1R)-1,3-bis[(38-{[({4-[(1E)-2-{4-[(5S,7S)-7-{[(tert-butoxy)carbonyl]amino}-5,7-dicarboxyheptanamido]phenyl}diazen-1-yl]phenyl}carbamoyl)methyl]carbamoyl}-3,6,9,12,15,18,21,24,27,30,33,36-dodecaoxaoctatriacontan-1-yl)carbamoyl]propyl]carbamoyl}butanamido]-4-[(38-{[({4-[(1E)-2-{4-[(5S,7S)-7-{[(tert-butoxy)carbonyl]amino}-5,7-dicarboxyheptanamido]phenyl}diazen-1-yl]phenyl}carbamoyl)methyl]carbamoyl}-3,6,9,12,15,18,21,24,27,30,33,36-dodecaoxaoctatriacontan-1-yl)carbamoyl]butanamido]-3,6,9,12,15,18,21,24,27,30,33,36-dodecaoxanonatriacontan-39-amido}acetamido)phenyl]diazen-1-yl] phenyl}carbamoyl)propyl]-4-{[(tert-butoxy)carbonyl]amino}pentanedioic acid (14)

14 was prepared according to general procedure B, with BG-COOSu prepared according to general procedure A, without the addition of piperidine. HRMS (ESI): calc. for $C_{253}H_{1385}N_{37}O_{93}$ [M+4H]$^{4+}$: 1360.1807, found: 1360.1804.

(2S,4S)-2-Amino-4-[3-({4-[(1E)-2-[4-(2-{1-[(4R)-4-[(38-{[({4-[(1E)-2-{4-[(5S,7S)-7-amino-5,7-dicarboxyheptanamido]phenyl}diazen-1-yl]phenyl}carbamoyl)methyl]carbamoyl}-3,6,9,12,15,18,21,24,27,30,33,36-dodecaoxaoctatriacontan-1-yl)carbamoyl]-4-[(2R)-2-(4-{[(4-{[(2-amino-9H-purin-6-yl)oxy]methyl}phenyl)methyl]carbamoyl}butanamido)-4-{[(1R)-1,3-bis[(38-{[({4-[(1E)-2-{4-[(5S,7S)-7-amino-5,7-dicarboxyheptanamido]phenyl}diazen-1-yl]phenyl}carbamoyl)methyl]carbamoyl}-3,6,9,12,15,18,21,24,27,30,33,36-dodecaoxaoctatriacontan-1-yl)carbamoyl]propyl]carbamoyl}butanamido]butanamido]-3,6,9,12,15,18,21,24,27,30,33,36-dodecaoxanonatriacontan-39-amido}acetamido)phenyl]diazen-1-yl phenyl}carbamoyl)propyl] pentanedioic acid ($^{4\times}$BGAG$_{12}$)

$^{4\times}$BGAG$_{12}$ was prepared according to general procedure D. HRMS (ESI): calc. for $C_{233}H_{363}N_{37}O_{85}$ [M+6H]$^{6+}$: 840.2541, found: 840.2533.

(2S,4S)-2-(4-((4-(E)-(4-((R)-1-Azido-4-((2-((4-((E)-(4-((5S,7S)-7-((tert-butoxycarbonyl)amino)-5f-dicarboxyheptanamido)phenyl)diazenyl)phenyl)amino)-2-oxoethyl)carbamoyl)-39,44-dioxo-3,6,9,12,15,18,21,24,27,30,33,36-dodecaoxa-40,45-diazaheptatetracontan-47-amido)phenyl)diazenyl)phenyl)amino)-4-oxobutyl)-4-((tert-butoxycarbonyl)amino)pentanedioic acid (15)

15 was prepared according to general procedure B without adding piperidine for deprotection. The crude was subjected to RP-HPLC and azobenzene containing fractions were collected, dried and subjected to the next step without further characterization.

(2S,4S)-2-Amino-4-(4-((4-((E)-(4-((R)-41-(3-((2-((4-((E)-(4-((5S,7S)-7-amino-5,7-dicarboxyheptanamido)phenyl)diazenyl)phenyl)amino)-2-oxoethyl)amino)-3-oxopropyl)-1-azido-39,42-dioxo-3,6,9,12,15,18,21,24,27,30,33,36-dodecaoxa-40,43-diazapentatetracontan-45-amido)phenyl)diazenyl)phenyl)amino)-4-oxobutyl)pentanedioic acid (16)

16 was prepared according to general procedure D. HRMS (ESI): calc. for $C_{78}H_{115}N_{16}O_{27}$ [M+3H]$^{3+}$: 569.2700, found: 569.2705.

(2S,4S)-2-Amino-4-(4-((4-((E)-(4-((R)-41-(3-((2-((4-((E)-(4-((5S,7S)-7-amino-5,7-dicarboxyheptanamido)phenyl)diazenyl)phenyl)amino)-2-oxoethyl)amino)-3-oxopropyl)-1-(8-(4-((4-(((4-aminopyrimidin-2-yl)oxy)methyl)benzyl)amino)-4-oxobutanoyl)-8,9-dihydro-3H-dibenzo[b,f][1,2,3]triazolo[4,5-d]azocin-3-yl)-39,42-dioxo-3,6,9,12,15,18,21,24,27,30,33,36-dodecaoxa-40,43-diazapentatetracontan-45-amido)phenyl)diazenyl)phenyl)amino)-4-oxobutyl)pentanedioic acid ($^{2\times}$BCAG$_{12}$)

A 4 mL dram vial was charged with 16 dissolved in MeOH. BC-DBCO was added in one portion and the reaction mixture was incubated o.n. before all volatiles were removed under a gentle stream of nitrogen. The crude was taken up in DMF and water (9/1) and subjected to RP-HPLC purification to obtain $^{2\times}$BCAG$_{12}$ as a yellow powder after lyophilization. HRMS (ESI): calc. for $C_{109}H_{142}N_{21}O_{30}$ [M+3H]$^{3+}$: 742.0082, found: 742.0080.

(2S,4S)-2-((tert-Butoxycarbonyl)amino)-4-(4-((4-((E)-(4-(61-chloro-4,44,48-trioxo-7,10,13,16,19,22,25,28,31,34,37,40,52,55-tetradecaoxa-3,43,49-triazahenhexacontanamido)phenyl)diazenyl)phenyl)amino)-4-oxobutyl)pentanedioic acid (17)

17 was prepared according to general procedure B, with Halo-COOSu prepared according to general procedure A, without the addition of piperidine. HRMS (ESI): calc. for $C_{70}H_{117}ClN_8O_{25}$ [M+2H]$^{2+}$: 753.3913, found: 753.3917.

(2S,4S)-2-Amino-4-(4-((4-((E)-(4-(61-chloro-4,44,48-trioxo-7,10,13,16,19,22,25,28,31,34,37,40,52,55-tetradecaoxa-3,43,49-triazahenhexacontanamido)phenyl)diazenyl)phenyl)amino)-4-oxobutyl)pentanedioic acid (ClAG$_{12}$)

ClAG$_{12}$ was prepared according to general procedure D. HRMS (ESI): calc. for $C_{65}H_{109}ClN_8O_{23}$ [M+2H]$^{2+}$: 702.3642, found: 702.3642.

(2S,4S)-2-((tert-Butoxycarbonyl)amino)-4-(4-((4-((E)-(4-((R)-5-(3-((2-((4-((E)-(4-((5S,7S)-7-((tert-butoxycarbonyl)amino)-5,7-dicarboxyheptanamido)phenyl)diazenyl)phenyl)amino)-2-oxoethyl)amino)-3-oxopropyl)-64-chloro-4,7,47,51-tetraoxo-10,13,16,19,22,25,28,31,34,37,40,43,55,58-tetradecaoxa-3,6,46,52-tetraazatetrahexacontanamido)phenyl)diazenyl)phenyl)amino)-4-oxobutyl)pentanedioic acid (18)

18 was prepared according to general procedure B, with Halo-COOSu prepared according to general procedure A, without the addition of piperidine. HRMS (ESI): calc, for $C_{103}H_{158}ClN_{15}O_{35}[M+2H]^{2+}$: 1100.5377, found: 1100.5370.

(2S,4S)-2-Amino-4-(4-((4-((E)-(4-((R)-5-(3-((2-((4-((E)-(4-((5S,7S)-7-amino-5,7-dicarboxyheptanamido)phenyl)diazenyl)phenyl)amino)-2-oxoethyl)amino)-3-oxopropyl)-64-chloro-4,7,47,51-tetraoxa-10,13,16,19,22,25,28,31,34,37,40,43,55,58-tetradecaoxa-3,6,46,52-tetraazatetrahexacontanamido)phenyl)diazenyl)phenyl)amino)-4-oxobutyl)pentanedioic acid ($^{2\times}$ClAG$_{12}$)

$^{2\times}$ClAG$_{12}$ was prepared according to general procedure D. HRMS (ESI): calc, for $C_{93}H_{142}ClN_{15}O_{31}$ $[M+2H]^{2+}$: 1000.4852, found: 1000.4853.

(2S,4S)-2-(4-((4-((E)-(4-((1-Amino-39-oxo-3,6,9,12,15,18,21,24,27,30,33,36-dodecaoxa-40-azadotetracontan-42-yl)amino)phenyl)diazenyl)phenyl)amino)-4-oxobutyl)-4-((tert-butoxycarbonyl)amino)pentanedioic acid (19)

19 was prepared according to general procedure B without the addition of piperidine. Instead, Fmoc-protected compound was obtained after RP-HPLC purification, dried and redissolved in MeCN with the addition of 5% DBU. The reaction mixture was incubated for 1 h, before it was quenched by addition of HOAc and water and subjected to RP-HPLC. HRMS (ESI): calc, for $C_{55}H_{93}N_7O_{20}$ $[M+2H]^{2+}$: 585.8232, found: 585.8232.

(2S,2'S,4S,4'S)-4,4'-((((((1E,1'E)-((((R)-45-Amino-4,44,48,88-tetraoxo-7,10,13,16,19,22,25,28,31,34,37,40,52,55,58,61,64,67,70,73,76,79,82,85-tetracosaoxa-3,43,49,89-tetraazahennonacontane-1,91-diyl)bis(azanediyl))bis(4,1-phenylene))bis(diazene-2,1-diyl)bis(4,1-phenylene))bis(azanediyl))bis(4-oxobutane-4,1-diyl))bis(2-((tert-butoxycarbonyl)amino)pentanedioic acid) (20)

20 was prepared according to general procedure B without the addition of piperidine. Instead, Fmoc-protected compound was obtained after RP-HPLC purification, dried and redissolved in MeCN with the addition of 5% DBU. The reaction mixture was incubated for 1 h, before it was quenched by addition of HOAc and water and subjected to RP-HPLC. HRMS (ESI): calc, for $C_{115}H_{190}N_{15}O_{42}$ $[M+3H]^{3+}$: 818.1069, found: 818.1075.

(2S,2'S,4S,4'S)-4,4'-((((((1E,1'E)-((((R)-45-(5-((4-((2-Amino-9H-purin-6-yl)oxy)methyl)benzyl)amino)-5-oxopentanamido)-4,44,48,88-tetraoxo-7,10,13,16,19,22,25,28,31,34,37,40,52,55,58,61,64,67,70,73,76,79,82,85-tetracosaoxa-3,43,49,89-tetraazahennonacontane-1,91-diyl)bis(azanediyl))bis(4,1-phenylene))bis(diazene-2,1-diyl)bis(4,1-phenylene))bis(azanediyl))bis(4-oxobutane-4,1-diyl))bis(2-((tert-butoxycarbonyl)amino)pentanedioic acid) (21)

21 was prepared according to general procedure B, with BG-COOSu prepared according to general procedure A, with the first step conducted at 50° C. and without the addition of piperidine. HRMS (ESI): calc, for $C_{133}H_{208}N_{21}O_{45}$ $[M+3H]^{3+}$: 940.1549, found: 940.1546.

(2S,2'S,4S,4'S)-4,4'-((((((1E,1'E)-((((R)-45-(5-((4-(((2-Amino-9H-purin-6-yl)oxy)methyl)benzyl)amino)-5-oxopentanamido)-4,44,48,88-tetraoxo-7,10,13,16,19,22,25,28,31,34,37,40,52,55,58,61,64,67,70,73,76,79,82,85-tetracosaoxa-3,43,49,89-tetraazahennonacontane-1,91-diylbis(azanediyl))bis(4,1-phenylene))bis)diazene-2,1-diyl))bis(4,1-phenylene))bis(azanediyl))bis(4-oxobutane-4,1-diyl))bis(2-aminopentanedioic acid) ($^{2\lambda}$BGAG$_{12,460}$)

$^{2\lambda}$BGAG$_{12,460}$ was prepared according to general procedure D. HRMS (ESI): calc, for $C_{123}H_{193}N_{21}O_{41}$ $[M+4H]^{4+}$: 655.3418, found: 655.3416.

Dimethyl(2S,4S)-2-(4-((4-((E)-(4-((1-amino-39-oxo-3,6,9,12,15,18,21,24,27,30,33,36-dodecaoxa-40-azadotetracontan-42-yl)amino)phenyl)diazenyl)phenyl)amino)-4-oxobutyl)-4-((tert-butoxycarbonyl)amino)pentanedioate (23)

23 was prepared according to general procedure B without the addition of piperidine. Instead, Fmoc-protected compound was obtained after RP-HPLC purification, dried and redissolved in MeCN with the addition of 5% DBU. The reaction mixture was incubated for 1 h, before it was quenched by addition of HOAc and water and subjected to RP-HPLC. HRMS (ESI): calc, for $C_{57}H_{97}N_7O_{20}$ $[M+2H]^{2+}$: 599.8389, found: 599.8387.

Tetramethyl 4,4'-((((((1E,1'E)-((((R)-45-amino-4,44,48,88-tetraoxo-7,10,13,16,19,22,25,28,31,34,37,40,52,55,58,61,64,67,70,73,76,79,82,85-tetracosaoxa-3,43,49,89-tetraazahennonacontane-1,91-diyl)bis(azanediyl))bis(4,1-phenylene))bis(diazene-2,1-diyl)bis(4,1-phenylene))bis(azanediyl))bis(4-oxobutane-4,1-diyl))(2S,2S,4S,4S)-bis(2-((tert-butoxycarbonyl)amino)pentanedioate) (24)

24 was prepared according to general procedure B without the addition of piperidine. Instead, Fmoc-protected compound was obtained after RP-HPLC purification, dried and redissolved in MeCN with the addition of 5% DBU. The reaction mixture was incubated for 1 h, before it was quenched by addition of HOAc and water and subjected to RP-HPLC. HRMS (ESI): calc, for $C_{119}H_{198}N_{15}O_{42}$ $[M+3H]^{3+}$: 836.7945, found: 836.7940.

1,5-Dimethyl (2S,4S)-2-[3-({4-[(1E)-2-{4-[(2-{1-[(4R)-4-[(2)-2-amino-4-{[(1R)-1,3-bis[(38-{[2-({4-[(1E)-2-{4-[(5S,7S)-7-{[(tert-butoxy)carbonyl]amino}-8-methoxy-5-(methoxycarbonyl)-8-oxooctanamido]phenyl}diazen-1-yl]phenyl}amino)ethyl]carbamoyl}-3,6,9,12,15,18,21,24,27,30,33,36-dodecaoxaoctatriacontan-1-yl)carbamoyl]propyl]carbamoyl}butanamido]-4-[(38-{[2-({4-[(1E)-2-{4-[(5S,7S)-7-{[(tert-butoxy)carbonyl]amino}-8-methoxy-5-(methoxycarbonyl)-8-oxooctanamido]phenyl}diazen-1-yl]phenyl}amino)ethyl]carbamoyl}-3,6,9,12,15,18,21,24,27,30,33,36-dodecaoxaoctatriacontan-1-yl)carbamoyl]butanamido]-3,6,9,12,15,18,21,24,27,30,33,36-dodecaoxanonatriacontan-39-amido}ethyl)amino]phenyl}diazen-1-yl]phenyl}carbamoyl)propyl]-4-{[(tert-butoxy)carbonyl]amino}pentanedioate (25)

25 was prepared according to general procedure B without the addition of piperidine. Instead, Fmoc-protected compound was obtained after RP-HPLC purification, dried and redissolved in MeCN with the addition of 5% DBU. The reaction mixture was incubated for 1 h, before it was quenched by addition of HOAc and water and subjected to RP-HPLC. HRMS (ESI): calc. for $C_{243}H_{399}N_{31}O_{86}$ [M+4H]$^{4+}$: 1282.4460, found: 1282.4447.

1,5-Dimethyl (2S,4S)-2-[3-({4-[(1E)-2-{4-[(2-{1-[(4R)-4-[(2R)-2-(4-{[(4-{[(2-amino-9H-purin-6-yl)oxy]methyl}phenyl)methyl]carbamoyl}butanamido]-4-{[(1R)-1,3-bis[(38-{[2-({4-[(1E)-2-{4-[(5S,7S)-7-{[(tert-butoxy)carbonyl]amino}-8-methoxy-5-(methoxycarbonyl)-8-oxooctanamido]phenyl}diazen-1-yl]phenyl}amino)ethyl]carbamoyl}-3,6,9,12,15,18,21,24,27,30,33,36-dodecaoxaoctatriacontan-1-yl)carbamoyl]propyl]carbamoyl}butanamido]-4-[(38-{[2-({4-[(1E)-2-{4-[(5S,7S)-7-{[(tert-butoxy)carbonyl]amino}-8-methoxy-5-(methoxycarbonyl)-8-oxooctanamido]phenyl}diazen-1-yl)phenyl}amino)ethyl]carbamoyl}-3,6,9,12,15,18,21,24,27,30,33,36-dodecaoxaoctatriacontan-1-yl)carbamoyl]butanamido]-3,6,9,12,15,18,21,24,27,30,33,36-dodecaoxanonatriacontan-39-amido}ethyl)amino]phenyl}diazen-1-yl]phenyl}carbamoyl)propyl]-4-{[(tert-butoxy)carbonyl]amino}pentanedioate (26)

A 4 mL dram vial was charged with 25 (1.0 equiv.), BG-COOH (1.1 equiv.) and dissolved in DIPEA (4.0 equiv.) and DMF before HBTU (1.2 equiv.) was added in one portion. The mixture was incubated for 2 h before it was quenched by addition of 5 vol % HOAc and subjected to RP-HPLC. HRMS (ESI): calc. for $C_{261}H_{417}N_{37}O_{89}$ [M+4H]$^{4+}$: 1374.2328, found: 1374.2305.

(2S,4S)-2-Amino-4-[3-({4-[(1E)-2-{4-[(2-{1-[(4R)-4-[(38-{[2-({4-[(1E)-2-{4-[(5S,7S)-7-amino-5,7-dicarboxyheptanamido]phenyl}diazen-1-yl]phenyl}amino)ethyl]carbamoyl}-3,6,9,12,15,18,21,24,27,30,33,36-dodecaoxaoctatriacontan-1-yl)carbamoyl]-4-[(2R)-2-(4-{[(4-{[(2-amino-9H-purin-6-yl)oxy]methyl}phenyl)methyl]carbamoyl}butanamido]-4-{[(1R)-1,3-bis[(38-{[2-({4-[(1E)-2-{4-[(5S,7S)-7-amino-5,7-dicarboxyheptanamido]phenyl}diazen-1-yl]phenyl}amino)ethyl]carbamoyl}-3,6,9,12,15,18,21,24,27,30,33,36-dodecaoxaoctatriacontan-1-yl)carbamoyl]propyl]carbamoyl}butanamido]butanamido]-3,6,9,12,15,18,21,24,27,30,33,36-dodecaoxanonatriacontan-39-amido}ethyl)amino]phenyl}diazen-1-yl]phenyl}carbamoyl)propyl]pentanedioic acid ($^{4\times}$BGAG$_{12,460}$)

A 15 mL Falcon tube was charged with 26 and dissolved in MeOH/1 M LiOH (1/1) and allowed to stand at r.t. for 1 h it was quenched by addition of 5 vol % HOAc and subjected to RP-HPLC. The azobenzene-containing fractions (27) were pooled and lyophilized, and final deprotection was performed in neat TFA at 0° C. according to procedure 1.6. HRMS (ESI): calc. for $C_{233}H_{372}N_{37}O_{81}$ [M+7H]$^{7+}$: 712.3736, found: 712.3733.

1-(6-(((S)-5-((((9H-Fluoren-9-yl)methoxy)carbonyl)amino)-5-carboxypentyl)amino)-6-oxohexyl)-3,3-dimethyl-2-((1E,3E)-5-((Z)-1,3,3-trimethylindolin-2-ylidene)penta-1,3-dien-1-yl)-3H-indol-1-ium (30)

A round bottom flask was charged with 35.0 mg (72.4 μmol, 1.0 equiv.) of 1-(5-carboxypentyl)-3,3-dimethyl-2-((1E,3E)-5-((Z)-1,3,3-trimethylindolin-2-ylidene)penta-1,3-dien-1-yl)-3H-indol-1-ium (29) (Ueno et al., 2011) which was dissolved in E5 mL DMSO and 50 μL DIPEA. TSTU (21.8 mg, 72.4 μmol, 1.0 equiv.) was added in one portion and the mixture was incubated for 30 min before 32.0 mg (86.8 μmol, 1.2 equiv.) of Fmoc-Lys-OH (28) was added in one portion. The reaction mixture was incubated for another hour before it was quenched by addition of 50 μL HOAc and subjected to RP-HPLC to obtain 26 mg (32.2 μmol) of the desired product as a blue powder after lyophilization in 45% yield. HRMS (ESI): calc. for $C_{53}H_{61}N_4O_5$ [M]$^+$: 833.4636, found: 833.4639.

1-(6-(((S)-5-Amino-6-((2-((4-((E)-(4-((5S,7S)-7-((tert-butoxycarbonyl)amino)-5,7-dicarboxyheptanamido)phenyl)diazenyl)phenyl)amino)-2-oxoethyl)amino)-6-oxohexyl)amino)-6-oxohexyl)-3,3-dimethyl-2-((1E,3E)-5-((Z)-1,3,3-trimethylindolin-2-ylidene)penta-1,3-dien-1-yl)-3H-indol-1-ium (31)

31 was prepared according to general procedure B. HRMS (ESI): calc. for $C_{66}H_{85}N_{10}O_{10}$ [M]$^+$: 1177.6445, found: 1177.6452.

1-((S)-1-Amino-41-((2-((4-((E)-(4-((5S,7S)-7-((tert-butoxycarbonyl)amino)-5,7-dicarboxyheptanamido)phenyl)diazenyl)phenyl)amino)-2-oxoethyl)carbamoyl)-39,47-dioxo-3,6,9,12,15,18,21,24,27,30,33,36-dodecaoxa-40,46-diazadopentacontan-52-yl)-3,3-dimethyl-2-((1E,3E)-5-((Z)-1,3,3-trimethylindolin-2-ylidene)penta-1,3-dien-1-yl)-3H-indol-1-ium (32)

32 was prepared according to general procedure B with the first step conducted at 50° C. HRMS (ESI): calc, for $C_{93}H_{139}N_{11}O_{23}$ $[M+H]^{2+}$: 889.5033, found: 889.5037.

1-((S)-1-(4-(((2-Amino-9H-purin-6-yl)oxy)methyl)phenyl)-49-((2-((4-((E)-(4-((5S,7S)-7-((tert-butoxycarbonyl)amino)-5,7-dicarboxyheptanamido)phenyl)diazenyl)phenyl)amino)-2-oxoethyl)carbamoyl)-3,7,47,55-tetraoxo-11,14,17,20,23,26,29,32,35,38,41,44-dodecaoxa-2,8,48,54-tetraazahexacontan-60-yl)-3,3-dimethyl-2-((1E,3E)-5-((Z)-1,3,3-trimethylindolin-2-ylidene)penta-1,3-dien-1-yl)-3H-indol-1-ium (33)

33 was prepared according to general procedure B, with BG-COOSu prepared according to general procedure A, without the addition of piperidine. HRMS (ESI): calc, for $C_{111}H_{158}N_{17}O_{24}$ $[M+2H]^{3+}$: 715.3859, found: 715.3859.

1-((S)-49-((2-((4-((E)-(4-((5S,7S)-7-Amino-5,7-dicarboxyheptanamido)phenyl)diazenyl)phenyl)amino)-2-oxoethyl)carbamoyl)-1-(4-(((2-amino-9H-purin-6-yl)oxy)methyl)phenyl)-3,7,47,55-tetraoxo-11,14,17,20,23,26,29,32,35,38,41,44-dodecaoxa-2,8,48,54-tetraazahexacontan-60-yl)-3,3-dimethyl-2-((1E,3E)-5-((Z)-1,3,3-trimethylindolin-2-ylidene)penta-1,3-dien-1-yl)-3H-indol-1-ium (BGAG$_{12}$-Cy5)

BGAG$_{12}$-Cy5 was prepared according to general procedure D. HRMS (ESI): calc, for $C_{106}H_{150}N_{17}O_{24}$ $[M+2H]^{3+}$: 682.0351, found: 682.0354.

Abbreviations: DIPEA: N,N-disopropylethylamine; DBU: 1,8-diazabicyclo[5.4.0]undec-7-ene; DMF: N,N-dimethylformamide; DMSO: dimethylsulfoxide; FA: formic acid; Su: succinimidyl; TFA: trifluoroacetic acid; TSTU: O—(N-succinimidyl)-N,N,N',N'-tetramethyluronium tetrafluoroborate.

HEK Cell and Cultured Neuron Electrophysiology

Whole cell patch clamp recordings from HEK 293T cells were performed 24-48 hours after transfection as previously described (Farrants et al., 2018). Briefly, voltage clamp recordings at −60 mV were performed in a high potassium (120 mM) solution to enable large inward currents upon receptor activation.

Whole cell patch clamp recordings of cultured cortical neurons were performed 4-6 days after transfection (11-15 DIV) in an extracellular solution containing (in mM): 138 NaCl, 1.5 KCl, 1.2 MgCl$_2$, 2.5 CaCl$_2$, 10 glucose and 5 HEPES, pH 7.4. Intracellular solution contained (in mM): 140 potassium gluconate, 10 NaCl, 5 EGTA, 2 MgCl$_2$, 1 CaCl$_2$, 10 HEPES, 2 MgATP and 0.3 Na$_2$GTP, pH 7.2. For hyperpolarization measurements, cells were adjusted to −60 mV with current injection prior to photoswitching. Only cells with a resting potential≤−40 mV were analyzed.

Unless otherwise noted, cells were incubated with 1-10 μM of PORTL for 45-60 min at 37° C. in the appropriate extracellular recording solution. Labeling efficiency was determined as previously described (Levitz et al., 2017). Illumination was applied to the entire field of view using a CoolLED pE-4000 through a 40× objective. Light intensity in the sample plane was 1-2 mW/mm$^2$. pClamp software was used for both data acquisition and control of illumination. All drugs were purchased from Tocris and applied using a gravity-driven perfusion system.

Results

Photoswitchable, orthogonal, remotely-tethered ligands ("PORTLs") were designed. Specifically, branched PORTLs were designed and characterized for SNAP, CLIP, Halo and nanobody-based labeling strategies.

An analysis of the prototypical system of benzylguanine-azobenzene-glutamate ("BGAG$_n$" where n=number of poly (ethylene glycol) (PEG) repeats between BG (benzylguanine) and azobenzene (A)) conjugated to SNAP-mGluR2 was conducted.

Figure 2A:
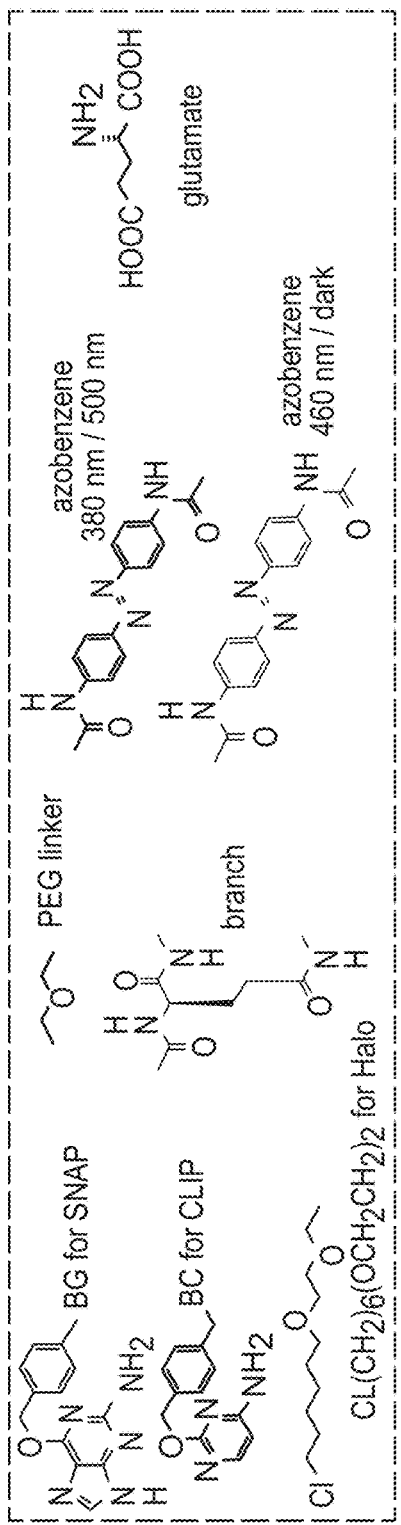
FIG. 2A-2J depict the effect of PORTLs on mGluR2 photoactivation.
Figure 2B:
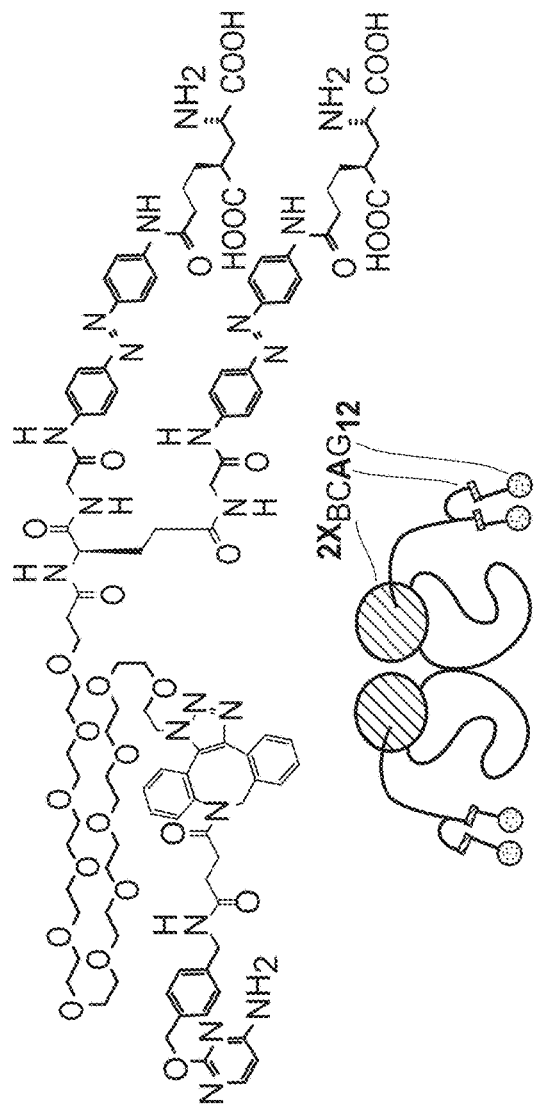
Figure 2C:
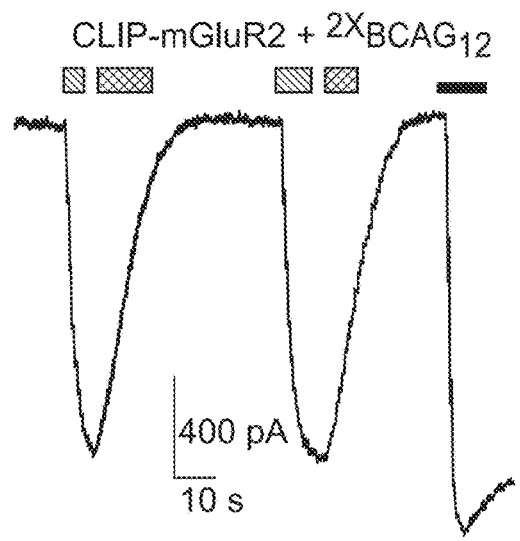
Figure 2D:
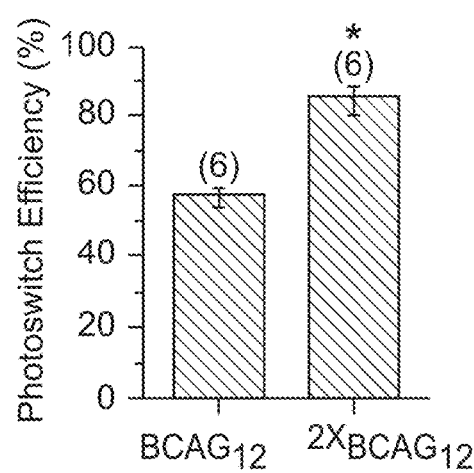

A major advantage of the PORTL system is the ability to design and synthesize PORTLs by flexible mix-and-matching of chemical moieties (FIG. 2A). To enable high efficiency optical control of mGluR2 tagged with CLIP, a variant of SNAP with orthogonal labeling (Gautier et al., 2008), "doubleBCAG$_{12}$" ($^{2×}$BCAG$_{12}$) was synthesized (Scheme S6 (FIG. 1F)). Similar to $^{2×}$BGAG$_{12}$, $^{2×}$BCAG$_{12}$ enabled near-complete optical control of CLIP-mGluR2 (FIG. 2B-2D). Branching did not alter the specificity of $^{2×}$BCAG$_{12}$, which showed no photocurrent when applied to cells expressing SNAP-mGluR2 (2.8±0.3% relative to 1 mM glutamate, n=3 cells).

Figure 1H:
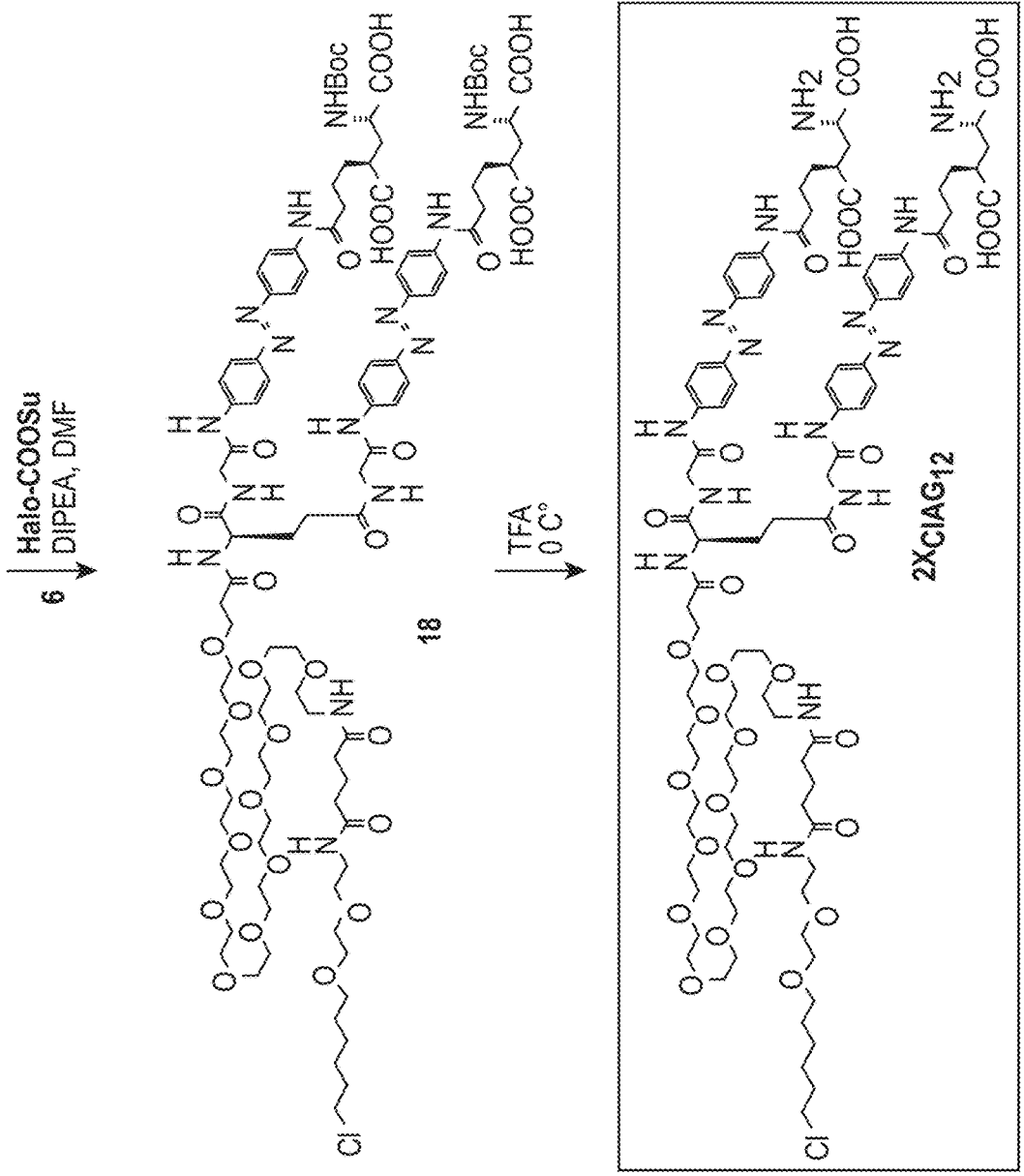
Figure 1I:
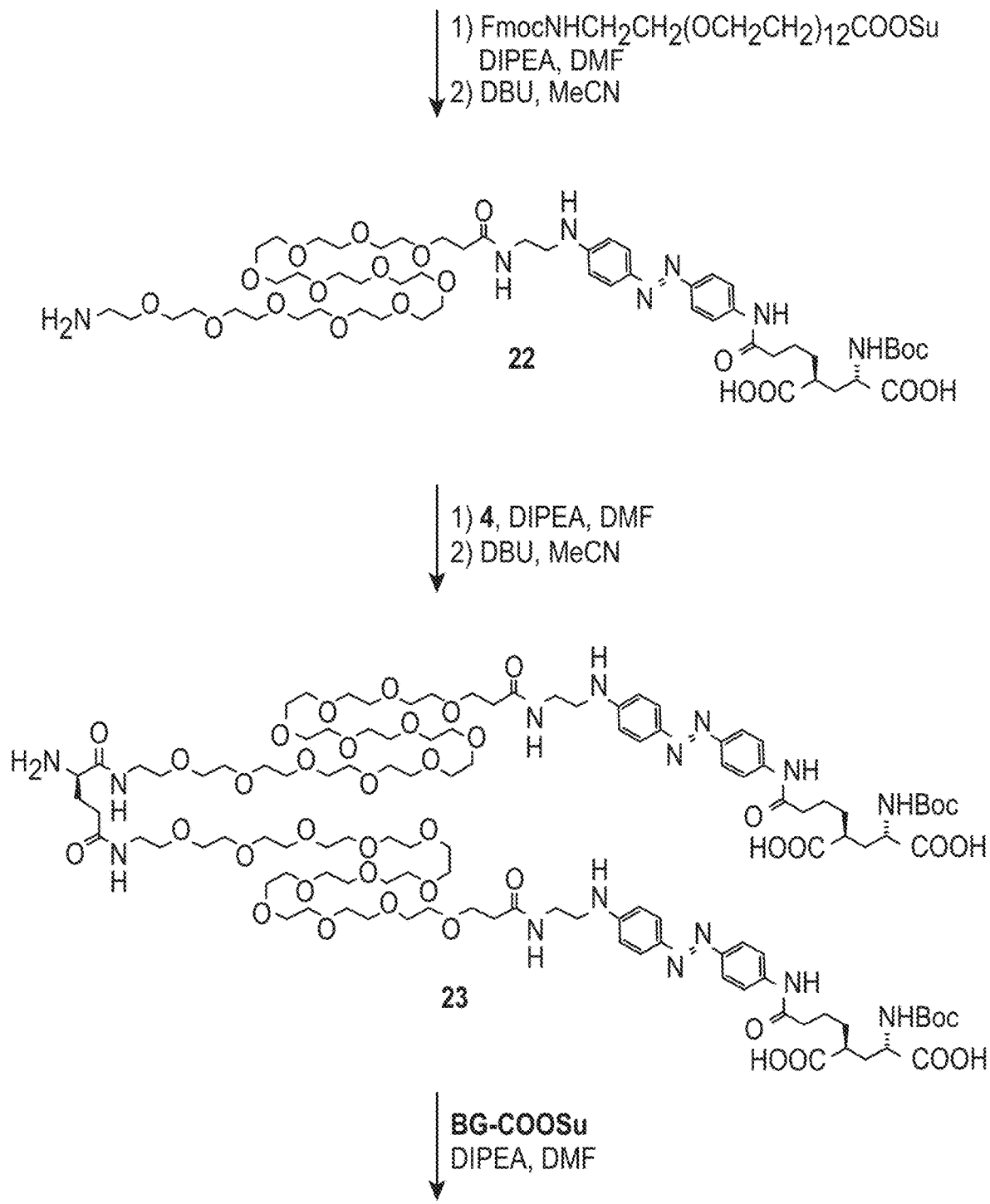
Figure 1I:
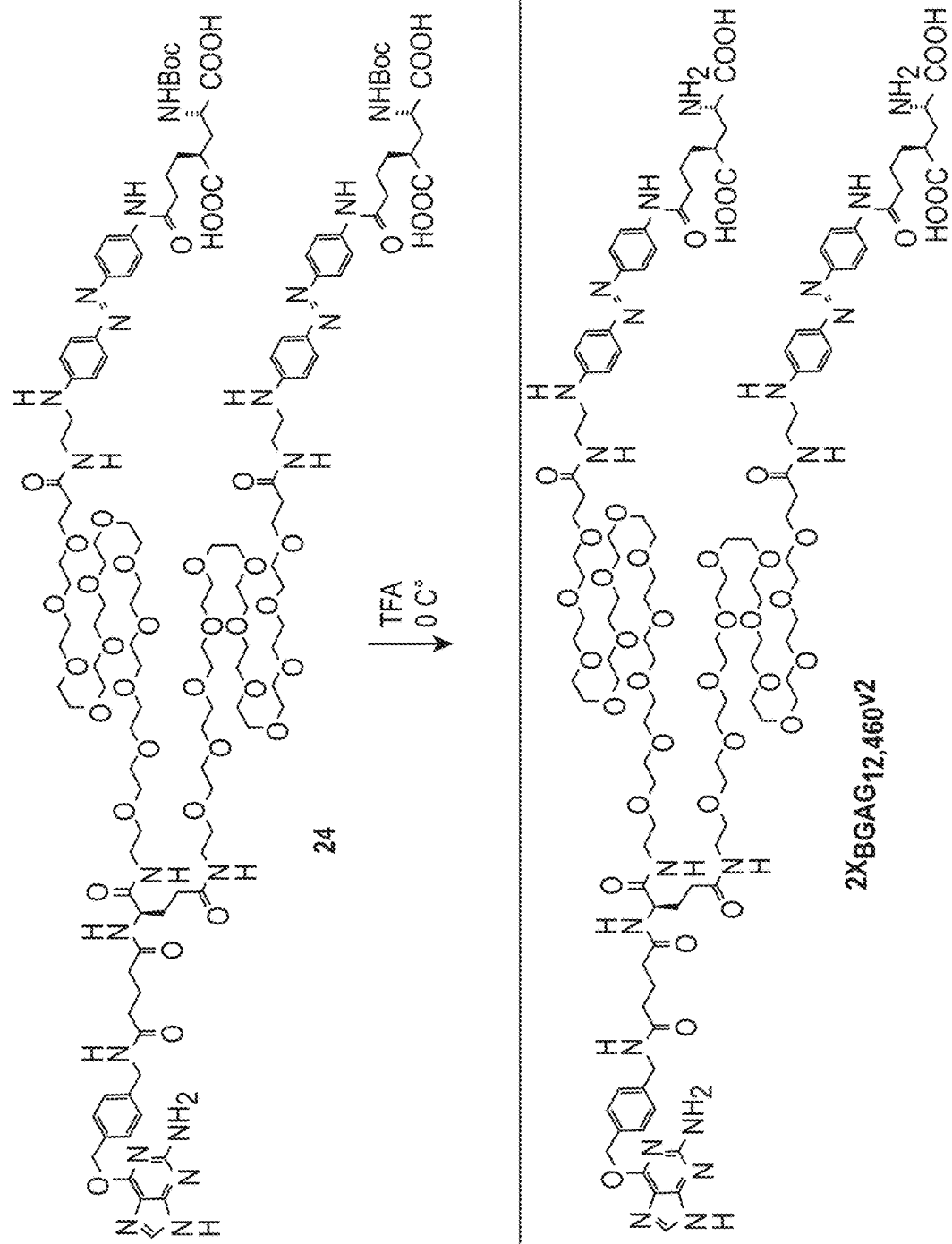
Figure 2E:
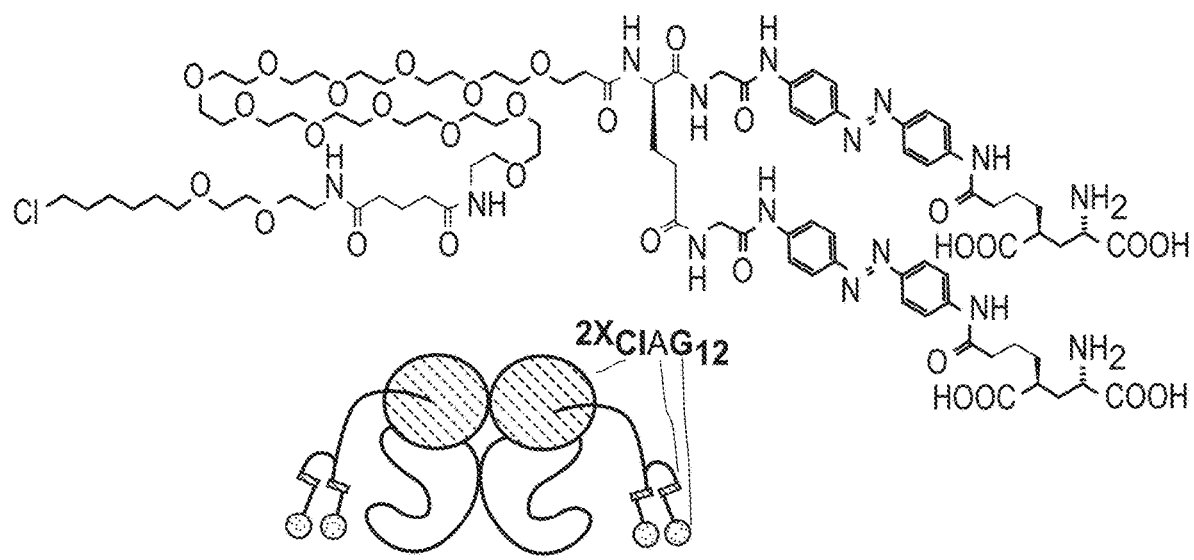
Figure 2F:
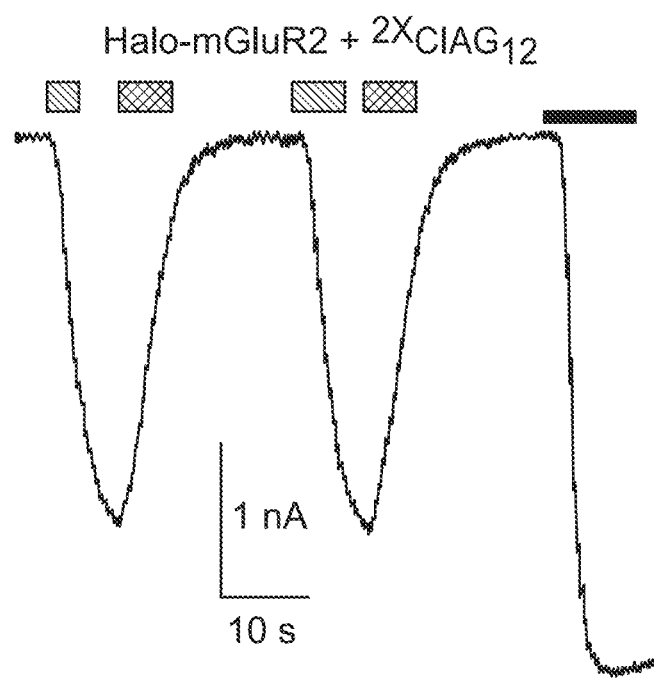
Figure 2G:
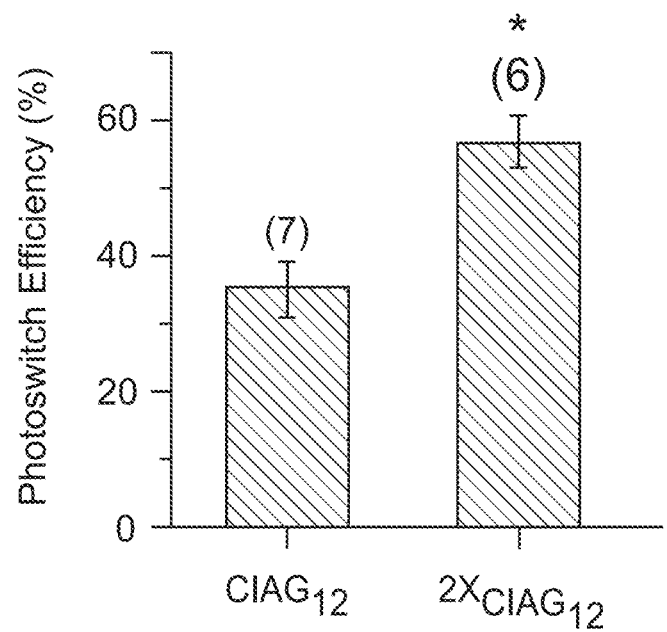
Figure 2H:
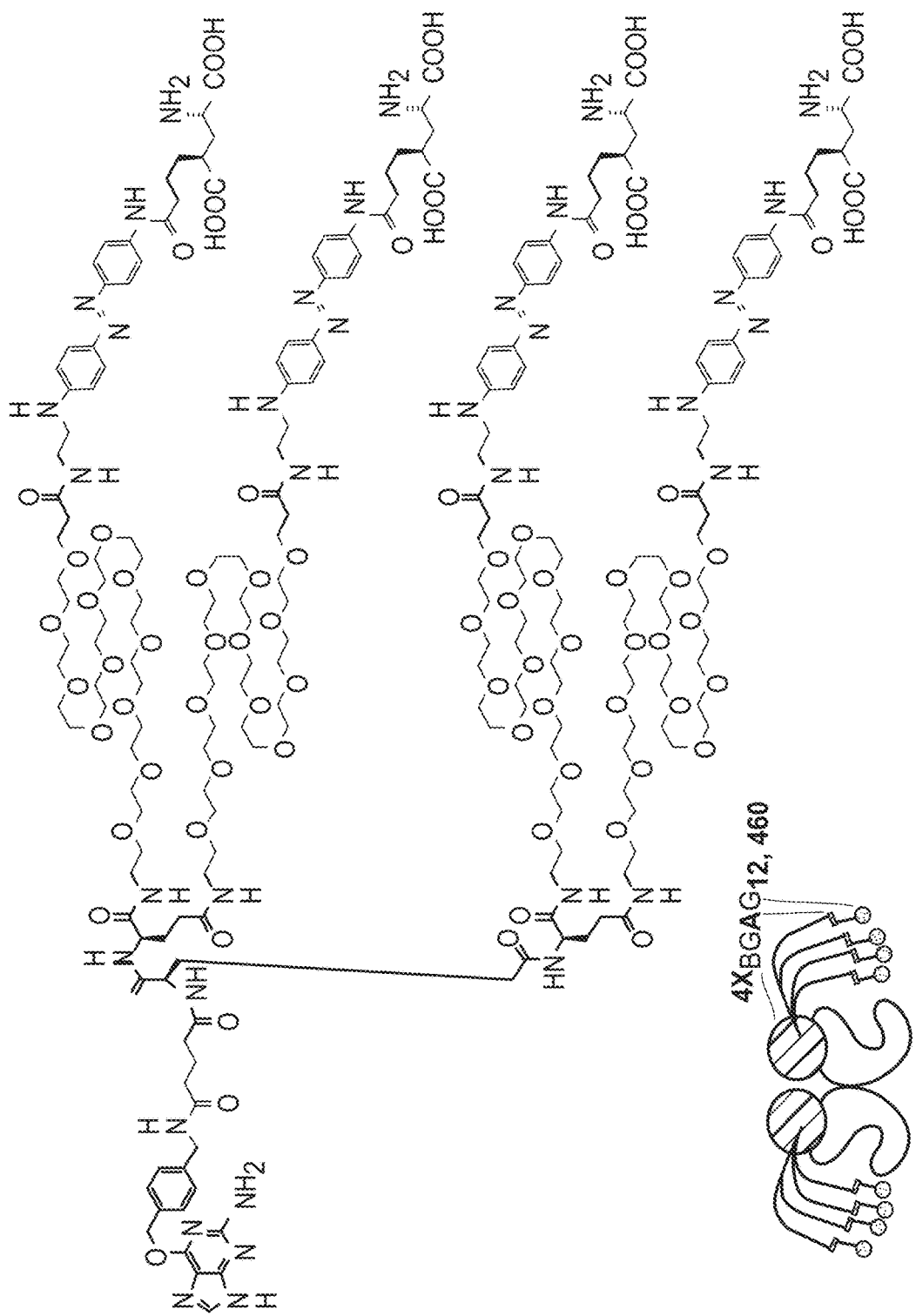
Figure 2I:
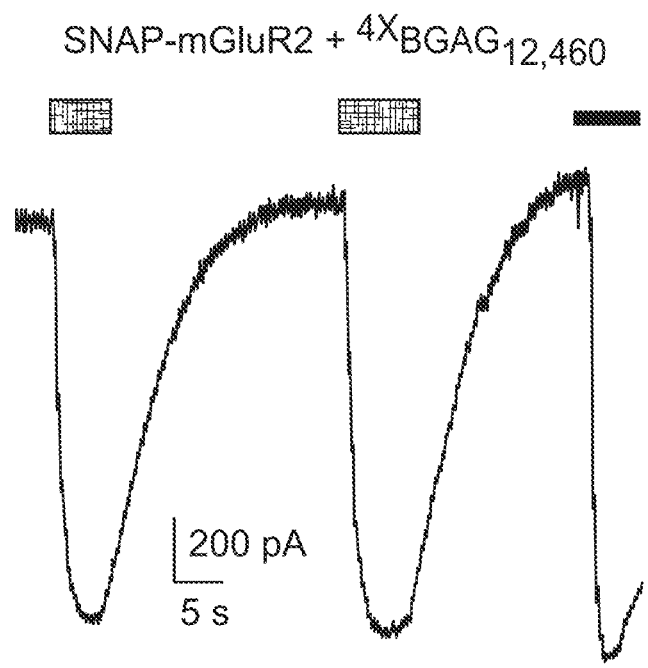
Figure 2J:
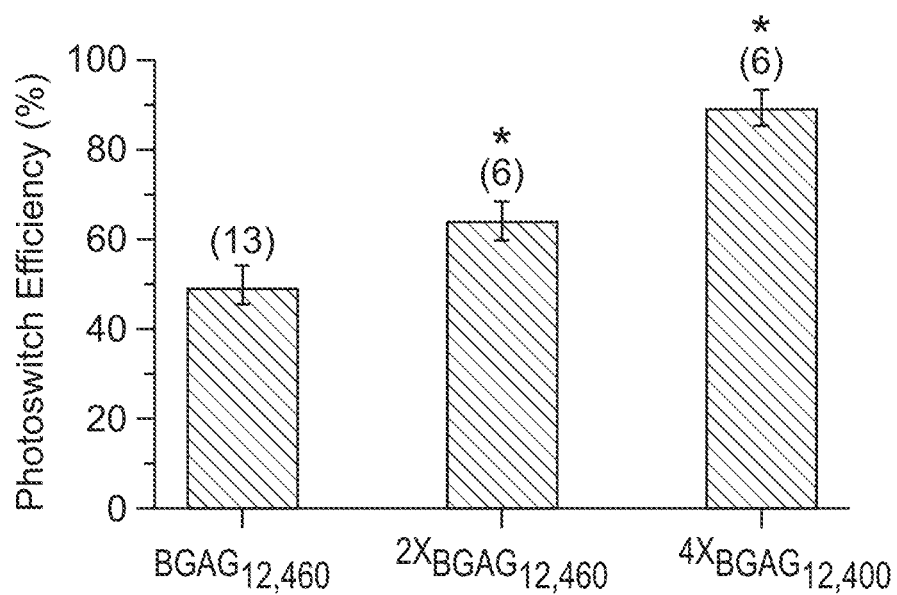

With the goal of further expanding the repertoire of PORTLs to a third self-labelling, orthogonal suicide enzyme, the Halo-tag, which reacts specifically with alkyl chlorides (Los et al., 2008), was used. ClAG$_{12}$ (Scheme S1, S7 (FIG. 1A and FIG. 1G)) was synthesized; and an N-terminally Halo-tagged mGluR2 construct which showed normal glutamate sensitivity was cloned. Based on the hypothesis that branching Halo-targeting PORTLs would enhance photoswitching, "doubleClAG$_{12}$" ($^{2×}$ClAG$_{12}$) (Scheme S8 (FIG. 1H); FIG. 2E) was synthesized. Both PORTLs showed photoactivation of mGluR2 with identical spectral properties to BGAGs (FIG. 2F), but the efficiency of photoactivation of Halo-mGluR2 was boosted by branching (FIG. 2F, 2G). The labeling efficiency of $^{2×}$ClAG$_{12}$ was characterized; a similar concentration-dependence to BGAG labeling of SNAP tags was found, where 1 μM labeling is sufficient for saturation. This result introduces the Halo-tag to the branched PORTL approach and expands the toolkit to three distinct, orthogonal protein tags.

Figure 1J:
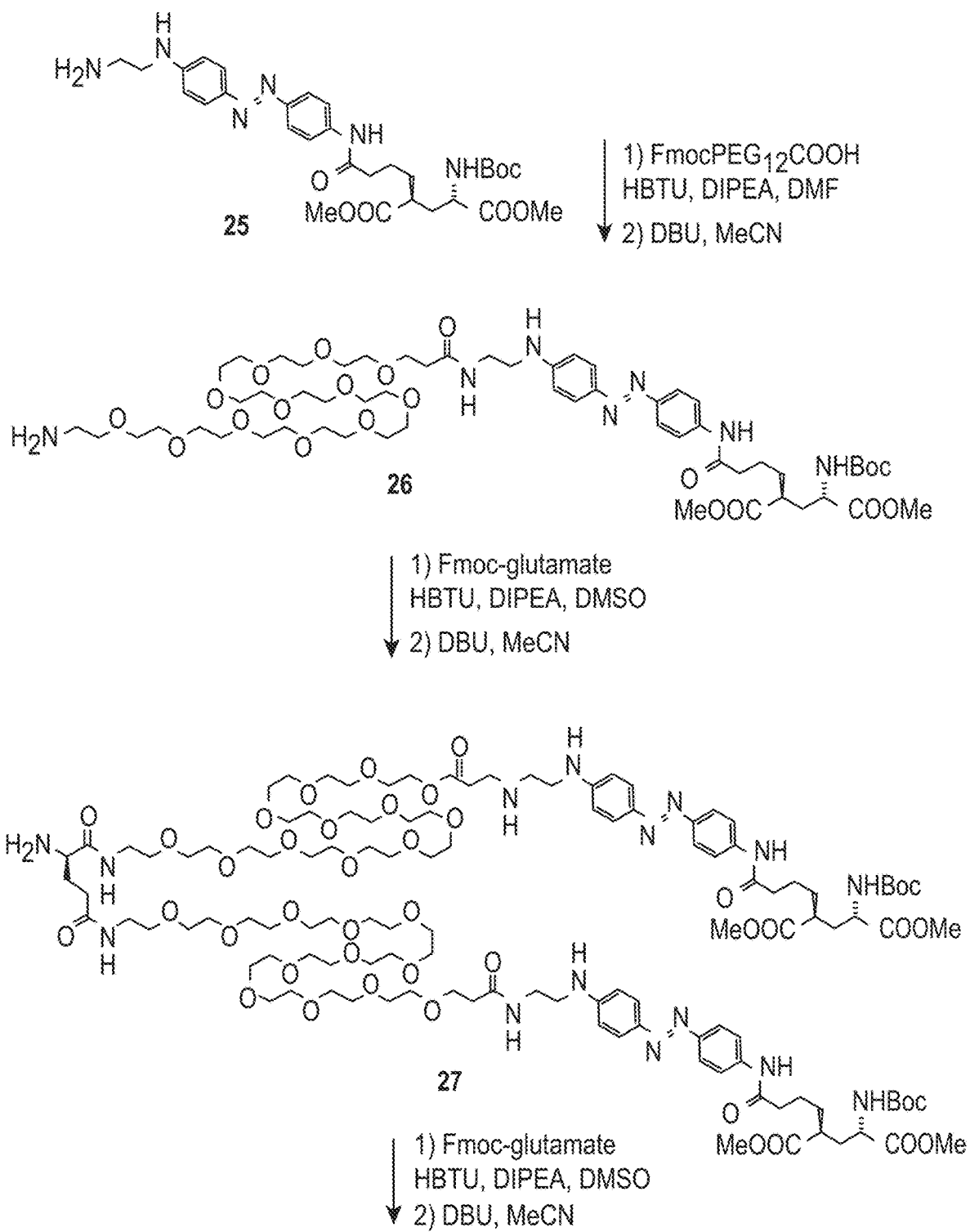
Figure 1J:
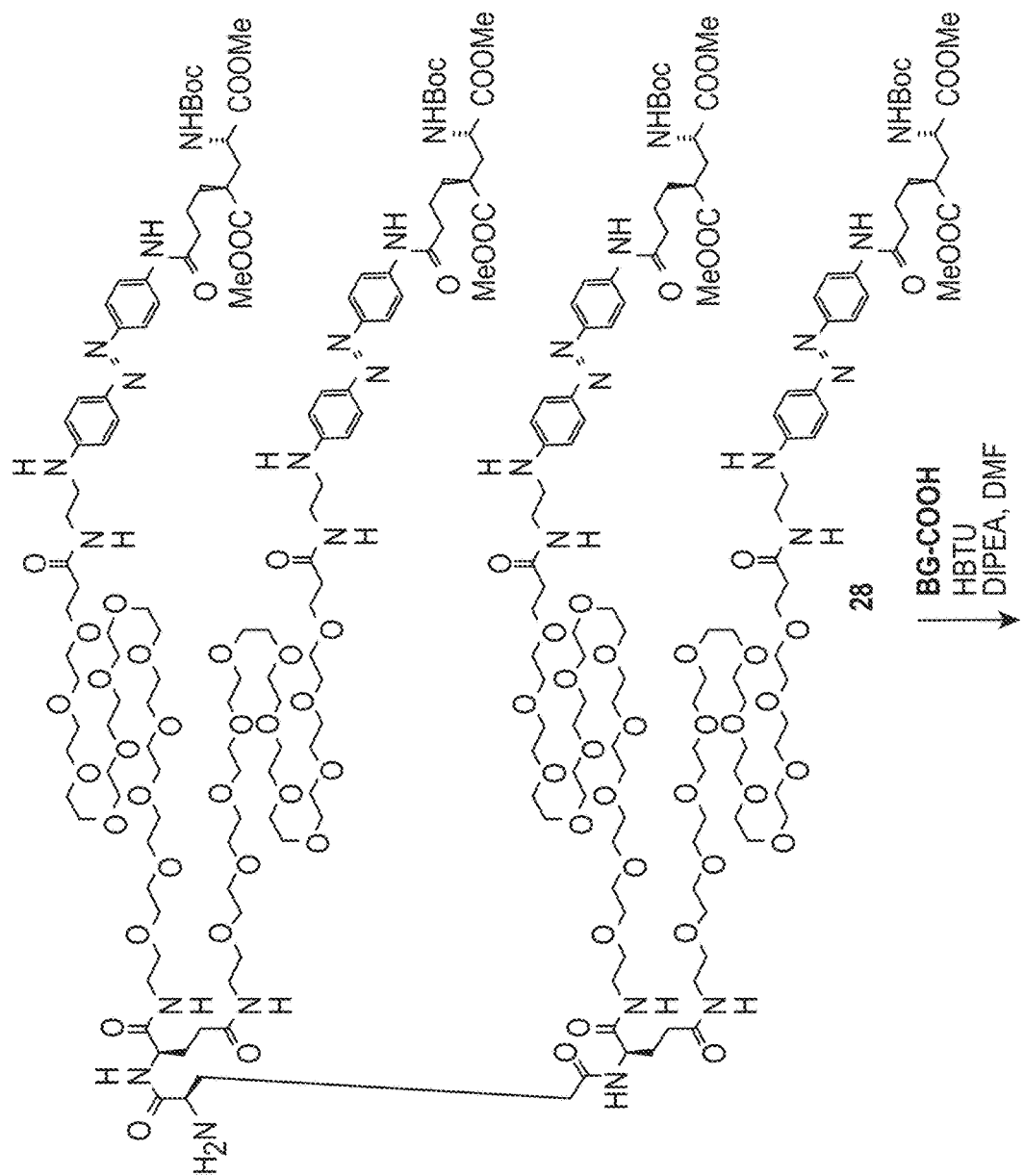
Figure 1J:
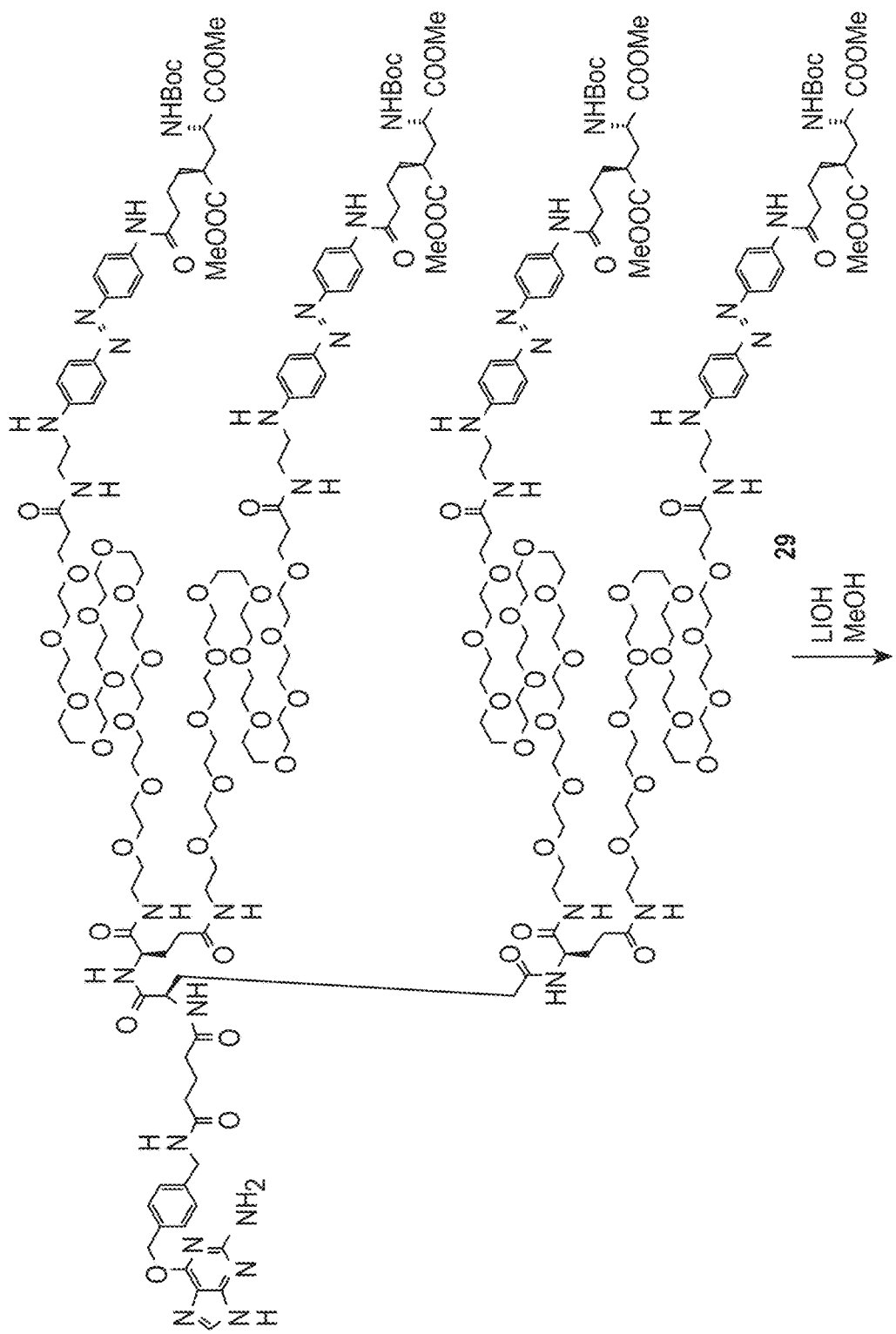
Figure 1J:
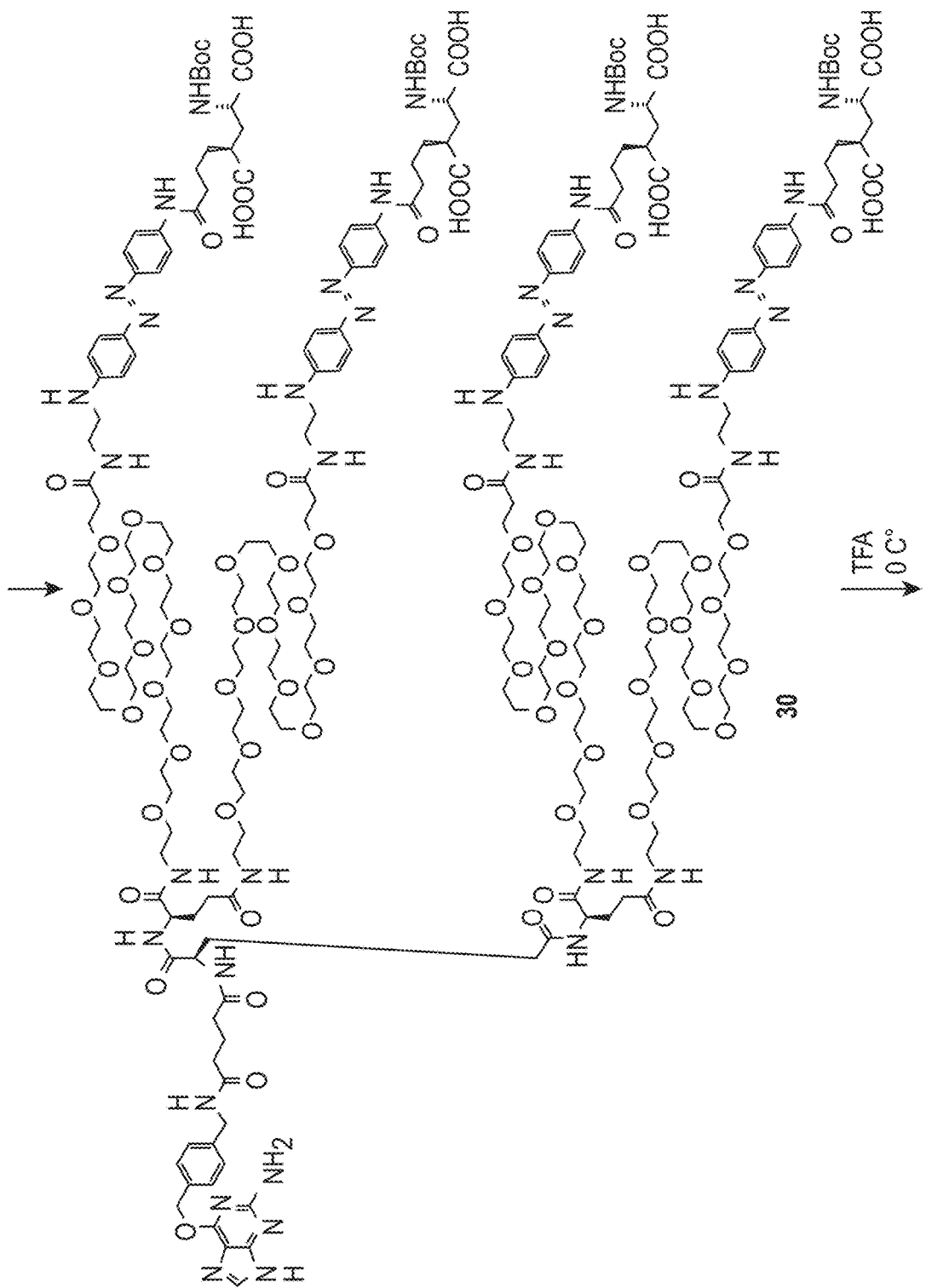
Figure 1J:
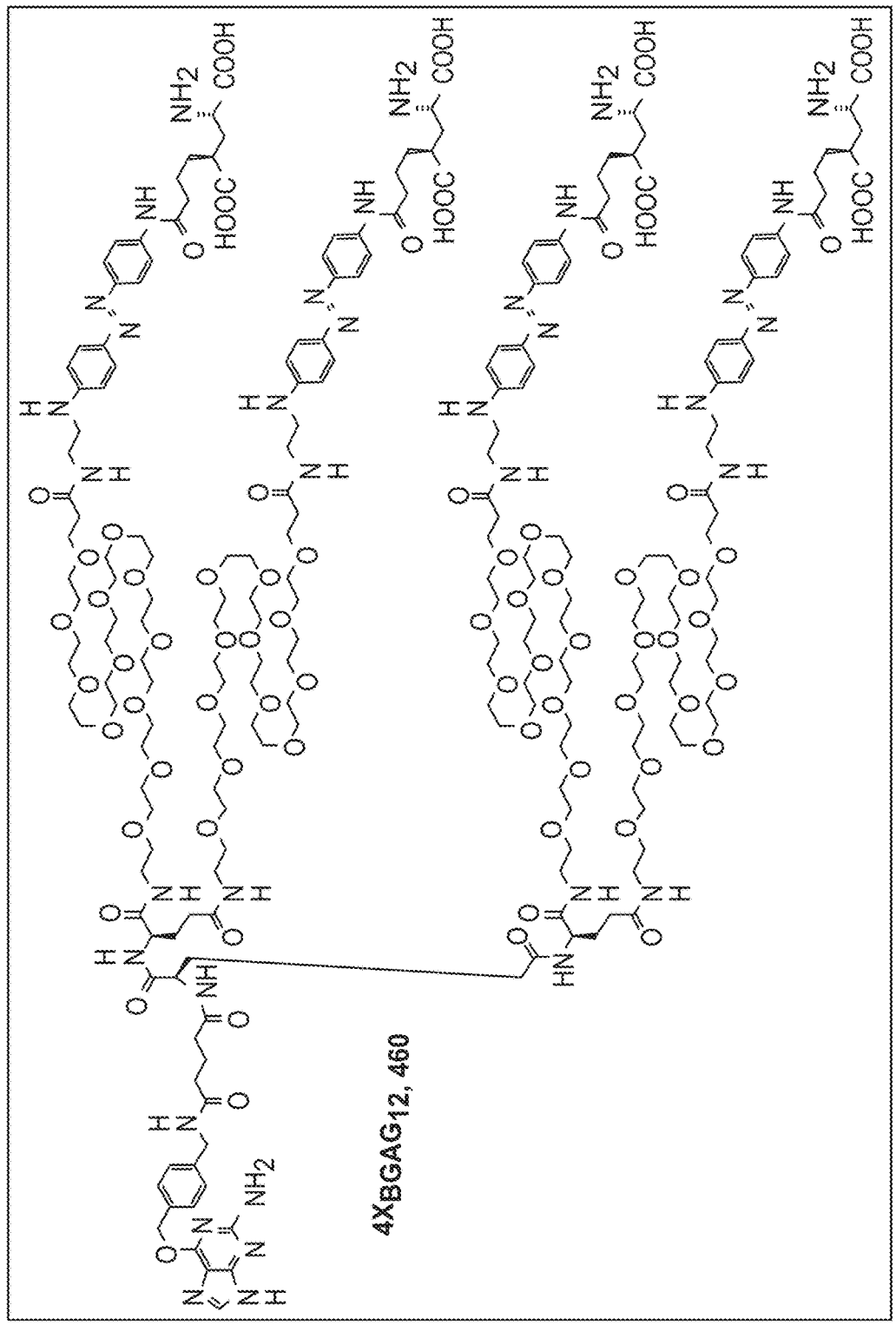
Figure 1K:
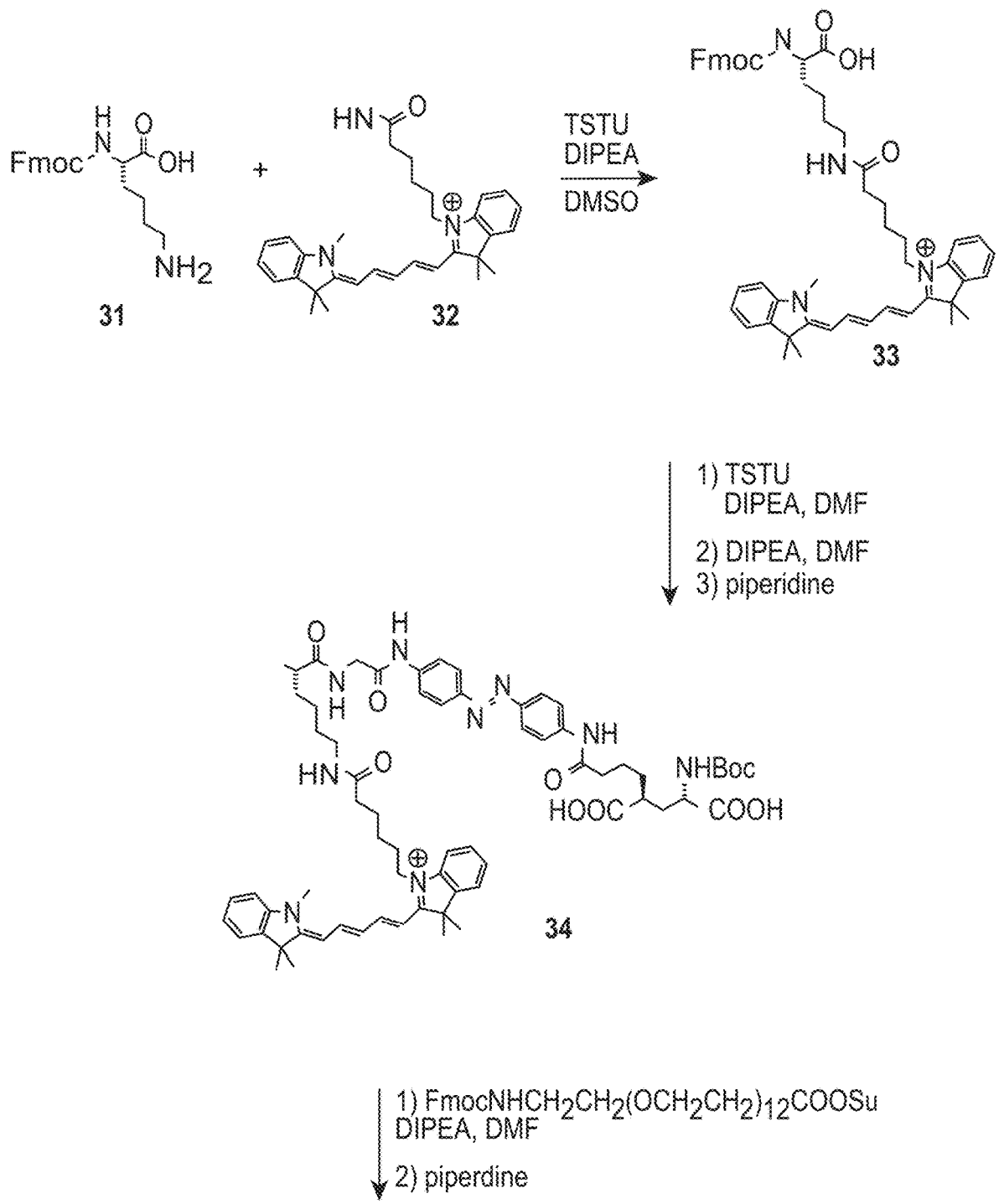
Figure 1K:
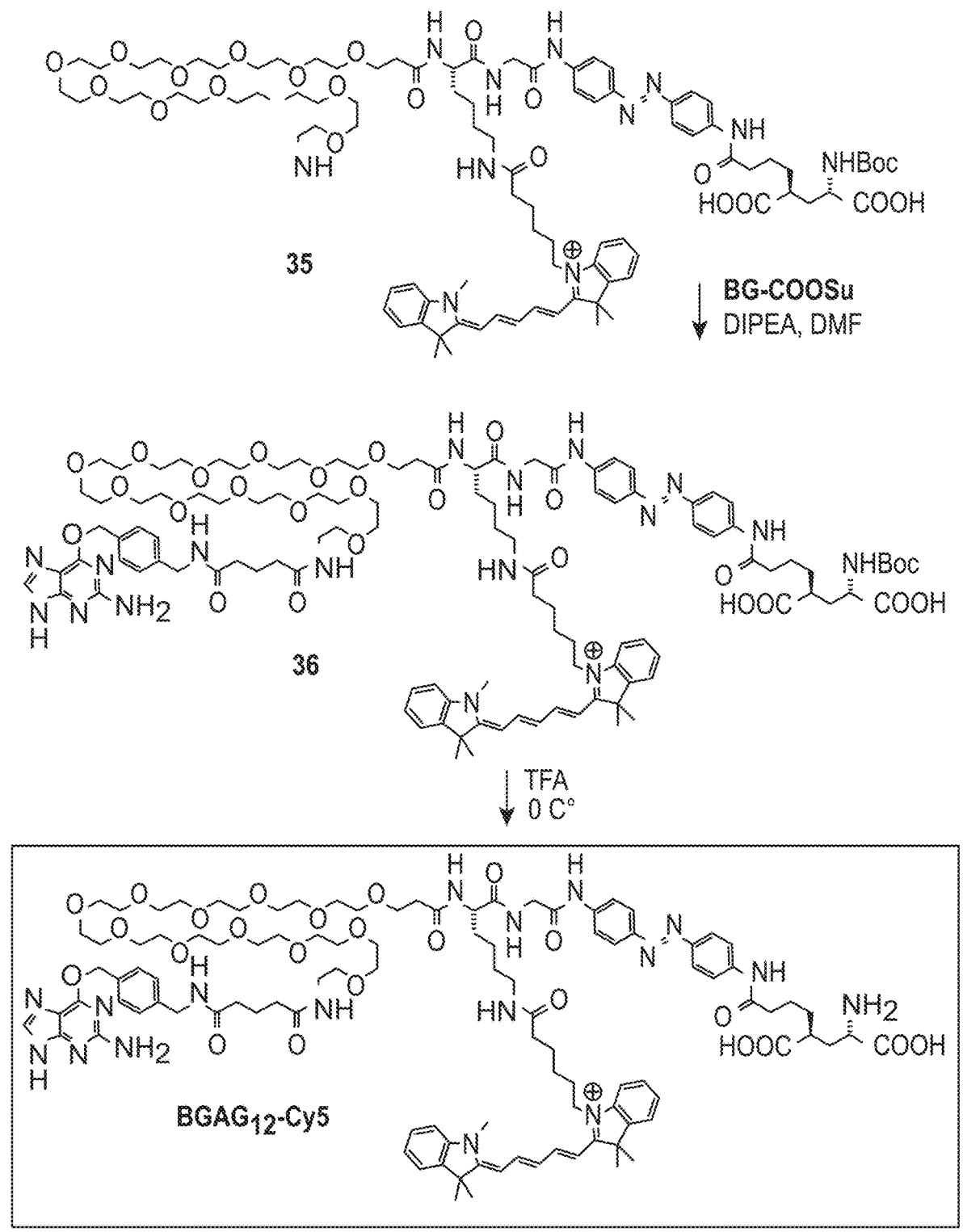

A key advantage of azobenzene-based photoswitches is the ability to tune the photochemical properties of the compound. The previously reported red-shifted BGAG$_{12,460}$ allows for visible-light induced, fast-relaxing photoactivation of mGluR2 which is advantageous in some settings, including for vision restoration applications (Berry et al. (2017) *Nature Commun.* 8:1862). However, BGAG$_{12,460}$ shows weaker activation of SNAP-mGluR2 than BGAG$_{12}$ likely due to the decreased population of cis at the photostationary state (Hull et al., 2018). "DoubleBGAG$_{12,460}$" was synthesized (Scheme S9 (FIG. 1I)); enhanced visible light photoactivation of SNAP-mGluR2 with doubleBGAG$_{12,460}$ was observed. Given the modest improvement of adding a second branch, $^{4×}$BGAG$_{12,460}$ with four azobenzene-glutamates was designed and synthesized; and further enhancement to produce near-complete photoactivation of mGluR2 was observed (Scheme S10 (FIG. 1J); FIG. 3H-J). In contrast to the bistable azobenzene of BGAG$_{12}$, BGAG$_{12,460}$-based PORTLs show fast-relaxation in the dark which allows the amplitude of photoactivation to be intensity-dependent. Consistent with an enhancement of the ability to produce a critical population of cis-azobenzenes, branching increased the light-sensitivity of $BGAG_{12,460}$.

Finally, a long-term goal of tethered photopharmacology is to incorporate the optical control afforded by such compounds into antibody-mediated targeting of proteins. "Nanobody-photoswitch conjugates" (NPCs) consisting of a SNAP-tagged nanobody labeled with a PORTL have been reported. NPCs containing an anti-GFP nanobody are able to photoactivate GFP-tagged mGluR2, but with limited efficiency (Farrants et al., 2018). Similar to other systems tested, $^{2\times}BGAG_{12}$ doubled the photoswitch efficiency of NPC-mediated photoswitching of mGluR2. This result further confirms that branched PORTLs are an effective general strategy for improving photoswitch efficiency.

FIG. 1A-1J (A) Toolset of chemical moieties for mix-and-match design of PORTLs for SNAP, CLIP and Halo-tagged receptors. (B-D)$^{2\times}BCAG_{12}$ (B) enhances efficiency of CLIP-mGluR2 photoactivation compared to $BCAG_{12}$. * indicates statistical significance (unpaired t-test, p=0.00008). (E-G)$^{2\times}ClAG_{12}$ (E) enhances efficiency of Halo-mGluR2 compared to $ClAG_{12}$ (F, G). * indicates statistical significance (unpaired t-test, p=0.006). (H-J) Branching enhances the efficiency of visible light-mediated (blue bar=460 nm) photoactivation of SNAP-mGluR2. * indicates statistical significance (unpaired t-test; p=0.02 between $BGAG_{12,460}$ and $^{2\times}BGAG_{12,460}$ and p=0.009 between $^{2\times}BGAG_{12,460}$ and $^{4\times}BGAG_{12,460}$). The numbers of cells tested are shown in parentheses. Error bars show s.e.m.

Example 2: Vision Restoration with 4×BGAG

To increase sensitivity in order to provide vision restoration at indoor intensities, a version of $BGAG_{12,460}$ with 4 branches ($^{4\times}BGAG_{12,460}$), each bearing a light-activated glutamate, was used. $^{4\times}BGAG_{12,460}$ increases efficacy by ~2-fold and sensitivity by ~5-fold in cultured cells.

Intravitreal injection of AAV was used to introduce SNAP-mGluR2 into either RGCs or ON bipolar cells (ON-BCs) of blind rd1 mice. $^{4\times}BGAG_{12,460}$:SNAP-mGluR2 in each of these cell types restored natural light aversion behavior and enabled animals to discriminate between two visual cues consisting of parallel lines spaced at different distances. The sensitivity to light of the restored visually-guided behavior increased by from 100-fold to about 250-fold over 1×BGAG—far more than expected from the cell culture measurements. This increase enabled animals to perform visual tasks at room light intensity and using iPad displays—a first for the 2-component approach to vision restoration. It was found that $^{4\times}$BGAG supports line pattern recognition approaching wild-type acuity limit. Furthermore, it was found that $^{4\times}$BGAG supports line pattern recognition as well as wildtype vision when visual displays move at 8 cm/s.

Formulation of $^{4\times}BGAG_{12,460}$ in β-cyclodextrin led to a restoration of light perception of at least 5 weeks after a single injection. A variant version based on the human mGluR6 (SNAP-mGluR6) can also be photoswitched by $BGAG_{12,460}$ in HEK293 cells, suggesting that it may be even more effective in ON-BCs, in which it is the principal receptor for glutamate released by photoreceptor cells and which contain the specialized signaling cascade and effector channel of mGluR6.

The $^{4\times}BGAG_{12,460}$:SNAP-mGluR system combines the high sensitivity of GPCR opsins with 6 major advantages of BGAG-mGluR: i) robust light response, ii) absence of photobleaching, iii) fast kinetics, iv) no function in wildtype (sighted) mice, suggesting selectivity for RGCs that have lost photoreceptor input (i.e. lack of interference with RGCs that retain input), and v) ability to be discontinued in case of adverse effect.

Materials and Methods

Animals, AAVs and Photoswitches

Mouse experiments were conducted under the express approval of the University of California Animal Care and Use Committee, wt mice (C57BL/6J) and rd1 mice (C3H) were purchased from the Jackson Laboratory and housed on a 12-h light/dark cycle with food and water ad libitum. cDNA encoding SNAP-mGluR2 was inserted in an established viral cassette under control of either the human synapsin promoter (hsyn-1) for expression in RGCs or a 4-copy concatemer of the mouse grm6 minimal promoter (4×grm6) for expression in ON-BCs and packaged in the AAV 2/2-4YF capsid. The vector, containing $10^{10}$-$10^{12}$ viral genomes was delivered in a 2 □l volume to the vitreous of the rd1 mouse eye via microinjection. rAAV injections were at p30-p60 and in vivo and in vitro experiments at p90-p160. AAVs were produced as previously described.

Photoswitch Preparation

Photoswitch compounds were synthesized using the protocol described in Broichhagen, J., et al. (2015) ACS Cent Sci 1, 383-393. Stock solution of 200 mM $BGAG_{12,460}$ (L-diastereomer) in 100% pharmaceutical grade DMSO (Cryoserv; Bioniche Pharma) was diluted 1:100 in sterile PBS for a final working solution of 1 mM in 1% DMSO. Working solutions were either prepared before administration, prepared in stock stored in the freezer and used as required, or salvaged from the recording bath and stored (either RT or freezer) for reuse. Application of $BGAG_{12,460}$ or $BGAG_{12}$ on retinal explants were performed in a volume of 200 μL at a concentration of 50 μM to 50 nM $BGAG_{12,460}$ (in PBS with >1% DMSO). For in vivo behavioral experiments, a 2-μL volume of 1 mM or 3.5 μL (final vitreal concentration of 1 μL) of $BGAG_{12,460}$ solution (in PBS with 1% DMSO) was injected into eyes that treated with AAV>6 wks earlier). For in vivo concentration dependence experiments, the mouse eye was assumed to contain a volume of 5.3 μL and a 2-μL volume of 3.5 μM, 1.825 μM and 0.1825 μM $BGAG_{12,460}$ solution (in PBS with 1% DMSO) was injected into eyes to obtain a final concentration of 1 μM, 500 nM and 50 nM[62]. For hydrated slow release 5% pharmaceutical grade beta cyclodextrin (cyclodex) in PBS was mixed with $BGAG_{12,460}$ for a final concentration of 3 μM and 2 μL were injected bilaterally into the mouse eye. $MAG0_{460}$ was synthesized and administered in 2 μL at a concentration of 100 μM.

Tissue Preparation and Immunohistochemistry

Mice>4 wks post-AAV2/2-hsyn-SNAP-mGluR2 treatment were injected with 1 uL of 10 uM of BG-conjugated Alexa Fluor-647 dye into the vitreous. 25 hrs later mice were sacrificed, eyes were fixed in 4% paraformaldehyde (Ted Pella) (30 min), retinas were removed and the tissue incubated in blocking buffer [10% normal goat serum, 1% BSA, 0.5% Triton X-100 in PBS (pH 7.4)] for 2 h at RT. Retinas were washed thoroughly using PBS and flat mounted on slides using Vectashield (Vector Laboratories) medium impregnated with DAPI (cell nuclei stain—blue). Retinas additionally co-injected with AAV2/2-hsyn-LiGluR were exposed to monoclonal antibody against GluK2/K3 (Millipore) (1:500 dilution in blocking buffer overnight at 4° C.) and followed by secondary anti-rabbit Alexa 488 antibody (Invitrogen) was applied (1:1,000 dilution for 2 h at RT) previously described in Gaub., et al. (2014)[12]. In vitro sequential labeling of SNAP-mGluR2 with the BG-conjugated Alexa Fluor-647 and antibody staining of the GluK2 subunit recognized in LiGluR was also successfully achieved using minimal fixation (10 min). For retinal sections, whole mounts were embedded in agarose (Sigma) and sectioned transverse using a vibratome (Leica Microsystems) at medium speed, maximum vibration, and 200-μm thickness. Retinal tissues used for immunohistochemistry on retinal cryosections or whole mounts were processed and examined by confocal microscopy (Leica TCS SP5; Leica Microsystems). For cell counting, retina were cryo-sectioned and stained with DAPI. Z-stack images (24 slices) of 1 μm$^3$ were obtained using the Zeiss LSM-880 NLO Airyscan microscope with 20× objective, increased offset was used to minimize background and differentiate distinct cells, and analysis was performed using the Imaris software to count individual cells in the 3D image.

Behavioral Analyses

The 2-chamber light-dark passive avoidance test was performed. White light (wavelength range) at ~100 μW cm$^2$ or either blue light (460/45 nm) or green light (535/50 nm) at 0.5-25 μW cm$^2$ was mounted above the chamber with homogeneously distributed light.

Animal movements were tracked using IR sensors on the shuttle box. Time spent in the light and dark chambers was measured and analyzed using Graphic State and Graphic State RT (Coulbourn Instruments).

Fear conditioning experiments were performed using Coulbourn single shock chamber with an LED screen that presented the visual cue mounted to the ceiling of the chamber. Animals were subjected to paired or unpaired light cued fear conditioning consisting of three shock trials at 0.7 mA over a span of 15 min. Freezing behavior in anticipation of the shock was recorded by Coulbourn's FreezeFrame software and normalized to movement behavior gathered before the stimulation. Performance was compared between paired and unpaired cohorts in order to determine if a fear response was conditioned to the stimulus transition.

Modified active avoidance was assayed as previously described[19], using the Coulbourn shuttle box (H10-11M-SC), however, now iPad tablet screens were mounted onto the shuttle cage wall, each displaying one of two images that differed in orientation or distance between two lines but were otherwise of equal shape, size, and light intensity. The aversive image side was paired with a foot shock of 0.7 mA. Upon recall the light patterns were reversed to avoid a bias for location and time spent on each side was recorded. Adaptation was tested by dimming or brightening the display to different intensities.

Results

Unbranched Monovalent $BGAG_{12,460}$ Works on a SNAP-Tagged Human mGluR6

The mGluR6 receptor is expressed in ON-BCs and in no other cell type in the retina (Dhingra and Vardi 2012) Wiley Interdiscip. Rev. Membr. Tramp. Signal 1:641). It serves as the ON-BC's main receptor for glutamate released by photoreceptor cells and has a specialized G protein signaling to effector signaling system in this cell type (Cao et al. (2011) J. Neurosci. 31:11521). It was considered that creation of a BGAG photo-activated version of mGluR6 for ON-BCs could take advantage of this native signaling cascade to produce an enhanced response to light. An N-terminal SNAP-tagged version of rat mGluR6 (SNAP-rmGluR6), along with the GIRK channel, was expressed in HEK293 cells. The cells were labeled with $BGAG_{12,460}$ and responses to flashes of blue (460 nm) light were examined. No photo-current was observed in these cells. (FIG. 3C). Human mGluR6 (SNAP-hmGluR6) was expressed in HEK293 cells, and the cells were labeled with $BGAG_{12,460}$; this time, GIRK photo-currents were observed that were as large as those with SNAP-mGluR2 (FIG. 3C). The similar potency of $BGAG_{12,460}$ photo-activation of SNAP-mGluR2 and SNAPhmGluR6 suggests that the latter may be more effective in ON-BCs, if mGluR6 has a privileged coupling to its native signaling cascade and effector channel.

FIG. 3A-3C. Monovalent $BGAG_{12,460}$ elicits rat SNAP-mGluR2 and human SNAP-mGluR6 GIRK photo-current in HEK293 cells. FIG. 3A. Group II and III mGluRs, like mGluR2 and 6, respectively, couple to GIRK channels in neurons and this system reconstitutes in non-neuronal cell lines, so that SNAP-mGluR2 or 6 coupled to a BGAG photoswitch will be activated by light and induce hyperpolarizing GIRK current. FIG. 3B. Blue (460 nm) light photo-activates $BGAG_{12,460}$:SNAP-mGluR2 and elicits an inward K+ current from co-expressed GIRK channel in a HEK293 cell voltage clamped at −60 mV with $[K+]_{in}=[K+]_{out}=150$ mM. FIG. 3C. While light activates GIRK in $BGAG_{12,460}$ HEK293 cells expressing the SNAP-tagged rat mGluR2 (SNAP-rmGluR2), it does not activate the rat SNAP-rmGluR6, but it does activate the human variant SNAP-hmGluR6.

Branched Multivalent BGAG Increases Efficacy and Sensitivity of SNAP-mGluR2 Activation in HEK293 Cells To increase the sensitivity of $BGAG_{12,460}$ to light the single branch that bears one light-activated glutamate (AG) per receptor attachment site (BG), (i.e. places one ligand on each mGluR subunit) was replaced with multiple branches, each bearing a light-activated glutamate (thereby yielding an excess of ligands per subunit) (FIG. 4A) (Acosta et al., 2020). In HEK293 cells, increasing ligand number to 2 ($^{2\times}BGAG_{12,460}$) and 4 ($^{4\times}BGAG_{12,460}$) progressively increases light-induced binding and activation of the receptor. $^{4\times}BGAG_{12,460}$ approximately doubles efficacy over $BGAG_{12,460}$, reaching close to the maximum activation that is achieved with saturating glutamate (FIG. 4B-4C). Importantly, $^{4\times}BGAG_{12,460}$ increases sensitivity (shifts the midpoint of the intensity-response curve) by ~5-fold in HEK293 cells (FIG. 4D).

Figure 4A:
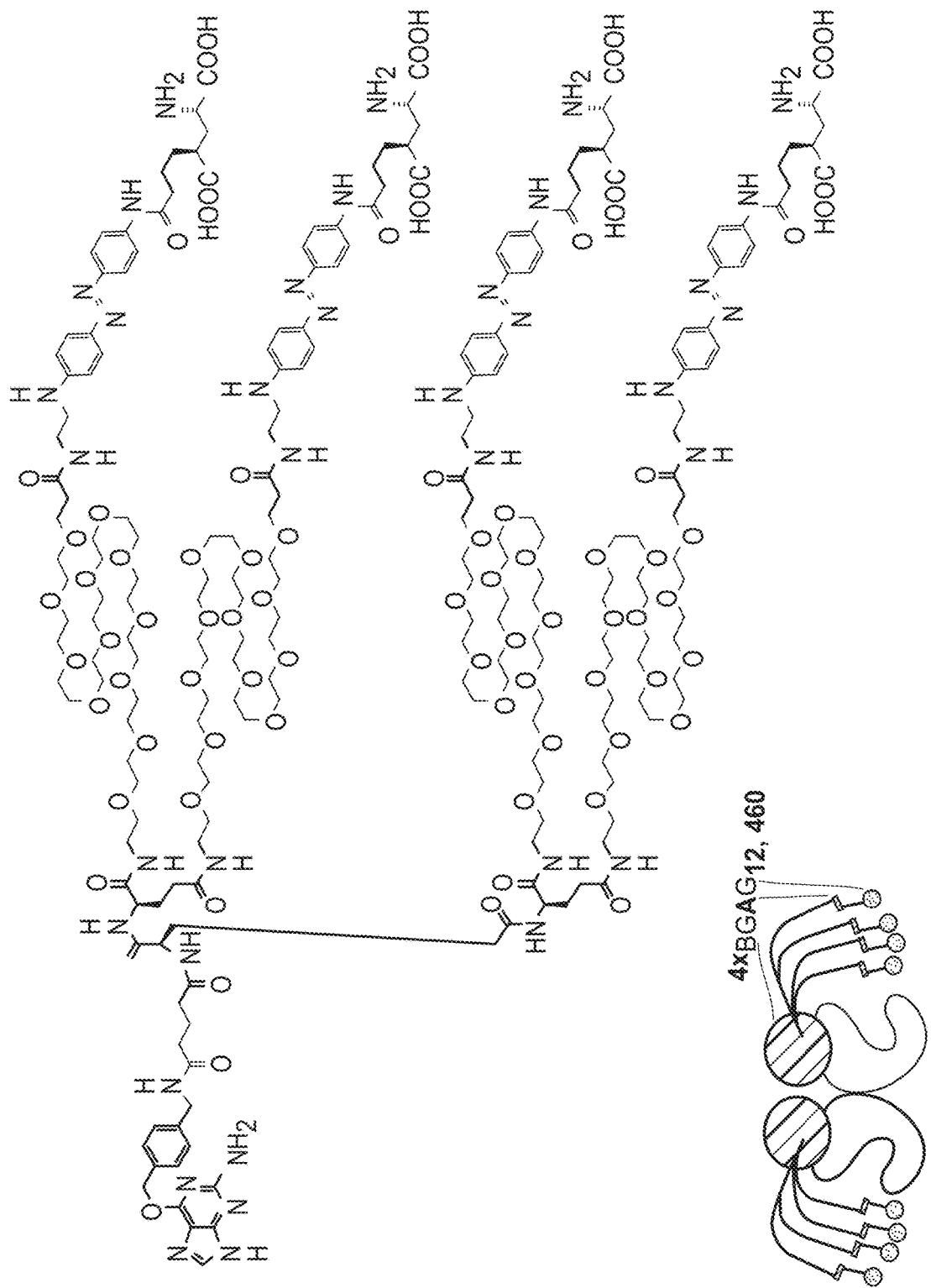
FIG. 4A-4D depict the effect of multibranched $BGAG_{12,460}$ on potency and sensitivity of SNAP-mGluR2 activation of GIRK channels in HEK293 cells.
Figure 4B:
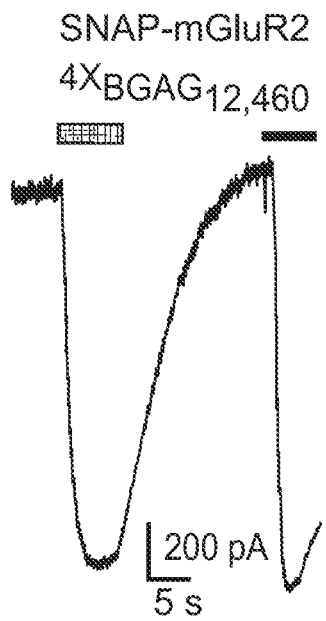
Figure 4C:
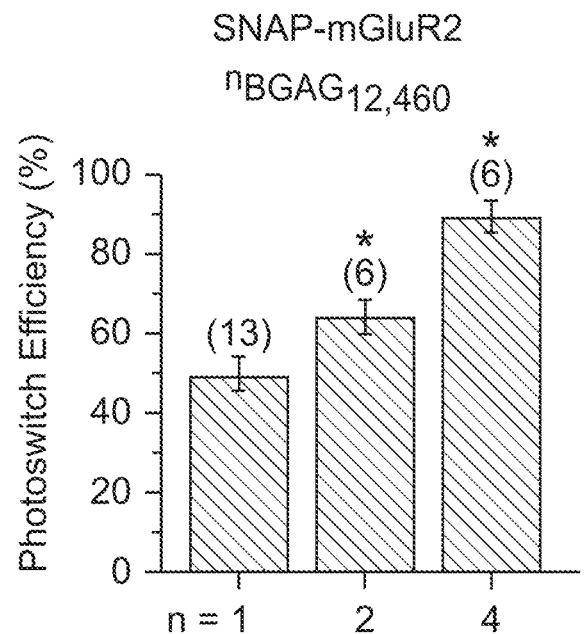
Figure 4D:
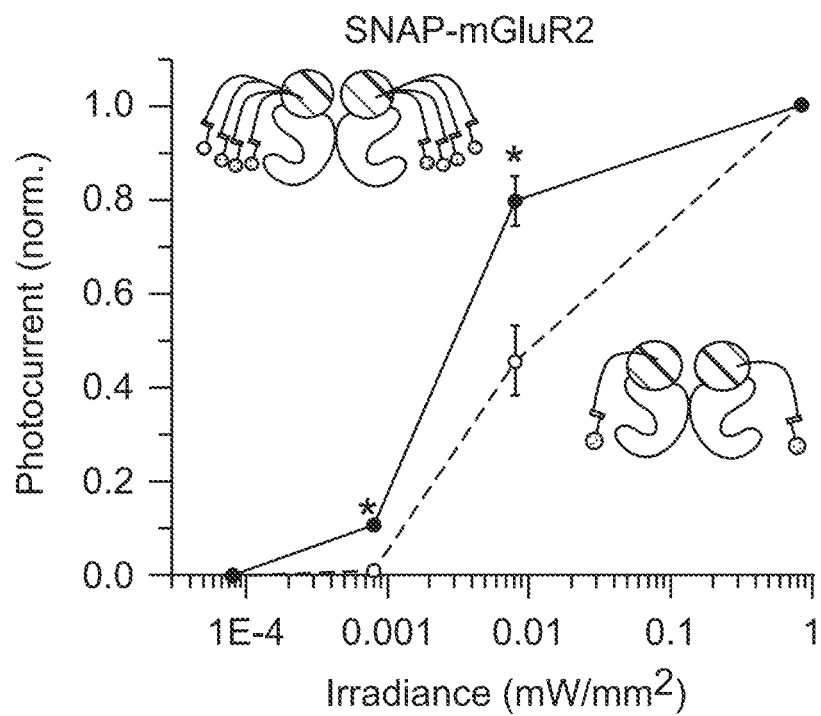

FIG. 4A-4D. Multibranched $BGAG_{12,460}$ increases potency and sensitivity of SNAP-mGluR2 activation of GIRK channels in HEK293 cells. FIG. 4A. $^{4\times}BGAG_{12,460}$ consists of a single BG end for 1:1 attachment to SNAP on each subunit of the mGluR and 4 branches of a 12-PEG linker, with each branch bearing a photoswitchable azobenzene-glutamate (AG). FIG. 4B. Representative example of $^{4\times}BGAG_{12,460}$ conjugated to SNA-mGluR2 photo-activates co-expressed GIRK channels to close to the maximal level obtained with saturating (1 mM) glutamate. FIG. 4C. Dependence of SNAP-mGluR2 photo-activation efficiency, read out as GIRK current, with single, 2-branch and 4-branch $BGAG_{12,460}$. FIG. 4D. Intensity-response curve shifts to the left (higher sensitivity) with $^{4\times}BGAG_{12,460}$.

4-Branched BGAG Restores High-Sensitivity Light Aversion

Figure 5A:
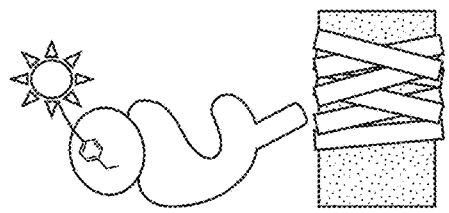
FIG. 5A-5D depict expression of SNAP-mGluR2 in RGCs of the rd1 mouse following intravitreal injection of AAV2 4YF hSyn-SNAP-mGluR2.

To examine whether this increase in sensitivity seen in cultured cells in vitro would translate to the retina in vivo, AAV was used to introduce the gene encoding SNAP-mGluR2 into retinal ganglion cells (RGCs) of blind rd1 mice under the human Synapsin promoter (hSyn) (AAV2 4YF: hSyn-SNAP-mGluR2) (FIG. 5A). Several weeks later, to gauge expression of SNAP-mGluR2 and the specificity of its BG labeling, a BG dye (FIG. 5B) was injected into the vitreous of the mice, at a time when their photoreceptor cells had degenerated (FIG. 5C). In cross-sections of the retina, dye was observed primarily in the dendrite layers of the RGCs (FIG. 5D).

Figure 5B:
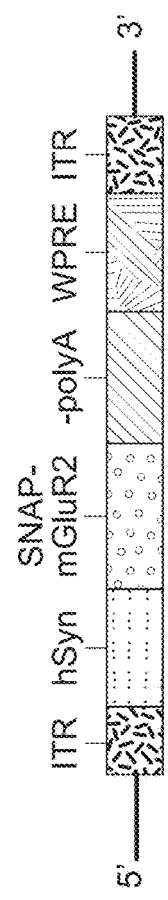
Figure 5C:
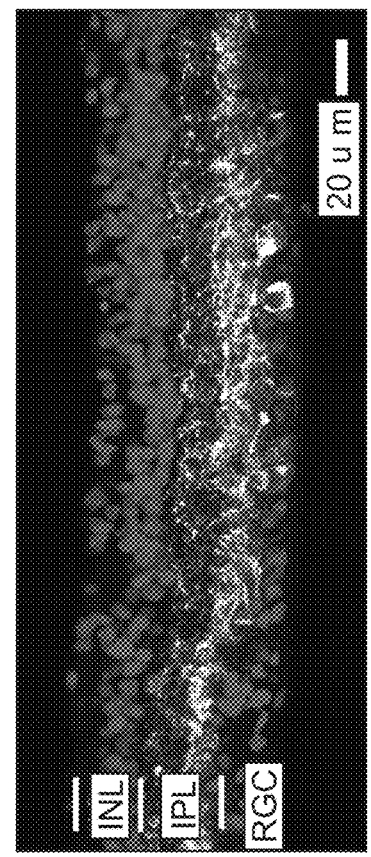
Figure 5D:
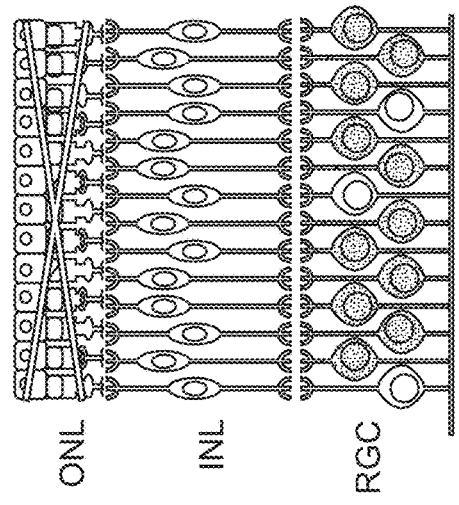

FIG. 5A-5D. Intravitreal injection of AAV2 4YF hSyn-SNAP-mGluR2 drives expression in RGCs of the rd1 mouse. FIG. 5A. AAV2 4YF hSyn-SNAP-mGluR2 viral delivery construct. FIG. 5B. SNAP tag on mGluR2 can be labeled with a fluorescent BG-dye.

FIG. 5C. Schematic of retina with loss of photoreceptor cell layer due to inherited retinal degeneration. FIG. 5D. Cross-section of isolated retina from rd1 mouse infected 6 weeks earlier with AAV2 4YF hSyn-SNAP-mGluR2 and labeled with BG-dye shows that expression of SNAP-mGluR2 is restricted to dendrites of RGCs.

To determine if $BGAG_{12,460}$:SNAP-mGluR2 could restore vision, another cohort of rd1 mice that received intravitreal injection of AAV2 4YF:hSyn-SNAP-mGluR2 underwent a second intravitreal injection≥6 weeks later with $^{4\times}BGAG_{12,460}$. Over the next 3-6 days, vision was tested in two paradigms, the first to assess whether the animals could distinguish light from dark and, if so, to determine the intensity of light that could be detected, and the second to test the ability to distinguish between two different spatial line patterns.

Natural light aversion behavior was tested. A 2-chamber shuttle box had an iPad-mini installed in each chamber, one of which was set to a completely illuminated white screen (88 uW/cm$^2$) and the other to black (FIG. 6C). Sighted mice are photophobic and spend less time in the illuminated chamber, whereas blind rd1 mice spend equal times in the two chambers. Rd1 mice expressing SNAP-mGluR2 in RGCs were injected intravitreally with $^{4\times}BGAG_{12,460}$ in PBS. In the first week after the $^{4\times}BGAG_{12,460}$ injection, these mice spent more time in the dark chamber than in the illuminated chamber (FIG. 6D, green symbols), contrasting with control rd1 littermates (that neither expressed SNAP-mGluR2 nor were injected with $^{4\times}BGAG_{12,460}$) which spent equal time in the two chambers (FIG. 6D, dashed violet line).

Three weeks after the $^{4\times}BGAG_{12,460}$ injection the dark preference of the SNAP-mGluR2 expressing rd1 mice disappeared (FIG. 6D, green symbols), consisting with the decline seen earlier with monovalent $BGAG_{12,460}$ (Berry et al. (2017) supra), and due, presumably, to clearing of $BGAG_{12,460}$ from the eye. Whether formulating $^{4\times}BGAG_{12,460}$ in β-cyclodextrin would extend the duration of restoration of light perception by prolonging persistence in the eye was tested. It was observed that $^{4\times}BGAG_{12,460}$ in β-cyclodextrin did indeed restore light perception for 4 weeks (FIG. 6D, red symbols), the longest observation period to date. This initial analysis was followed with a longer study; it was found that $^{4\times}BGAG_{12,460}$ in β-cyclodextrin restored light aversion for 6 weeks after the intravitreal injection, declined to about one half at week 7 and to background at 8 weeks (FIG. 6E).

These results indicate that $^{4\times}BGAG_{12,460}$:SNAP-mGluR2 in RGCs enables previously blind mice to detect dim room light. This represents a striking enhancement in sensitivity by almost 100-fold compared to that observed earlier with the monovalent $BGAG_{12,460}$, which required much higher intensity light (5 mW/cm$^2$), requiring a bright LED light source (Berry et al. (2017) supra).

Whether $^{4\times}BGAG_{12,460}$:SNAP-mGluR2 would also restore light perception in ON-BCs was tested. To test this, the gene encoding SNAP-mGluR2 was introduced into ON-BCs using the same AAV 4YF vector but replacing the hSyn promoter with the ON-BC selective promoter of the mGluR6 gene, which is exclusively expressed in ON-BCs. A concatemer of four copies of a minimal grm6 promoter (4×grm6) was used. Approximately 6 weeks after intravitreal injection of AAV2 4YF:4×grm6-SNAP-mGluR2 in rd1 mice, $^{4\times}BGAG_{12,460}$ in PBS was injected intravitreally, and the light/dark photo-aversion assay was used to test. In the first week after injection, these treated rd1 mice spent more time in the dark chamber, but this dark preference disappeared by week 3 post-injection of $^{4\times}BGAG_{12,460}$ in PBS (FIG. 6D, grey symbols). However, as seen above in RGCs, formulation in β-cyclodextrin extended the restoration of dark avoidance to 4 weeks (FIG. 6D, blue symbols).

Thus, the multivalent $^{4\times}BGAG_{12,460}$ activates SNAP-mGluR2 strongly enough in both RGCs and ON-BCs to support detection of dim light, at the level of room light and formulation in an excipient that is used for ocular delivery of steroid extends action for weeks after a single injection.

To quantify the sensitivity to light, the restoration of natural light aversion in the 2-chamber light/dark system was compared at different levels of illumination of the lighted chamber. Maximal light-aversion behavior was observed at 25 μW/cm$^2$, with a half-maximal response between 5 and 25 μW/cm$^2$ (FIG. 6F), an increase in sensitivity of ~250-fold compared to what was observed earlier with unbranched BGAG.

Figure 6A:
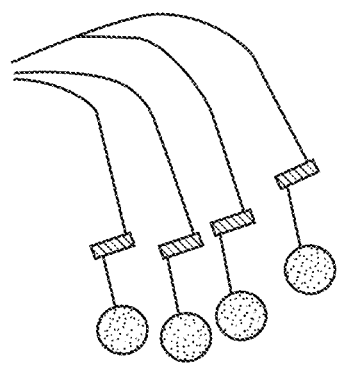
FIG. 6A-6F depict the effect of $^{4\times}BGAG_{12,460}$:SNAP-mGluR2 in retinal ganglion cells (RGCs) or ON-bipolar cells (ON-BCs) on light avoidance behavior in the rd1 mouse.
Figure 6C:
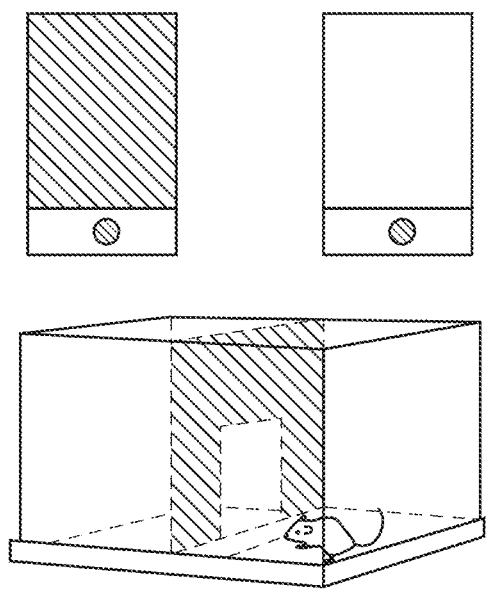
Figure 6B:
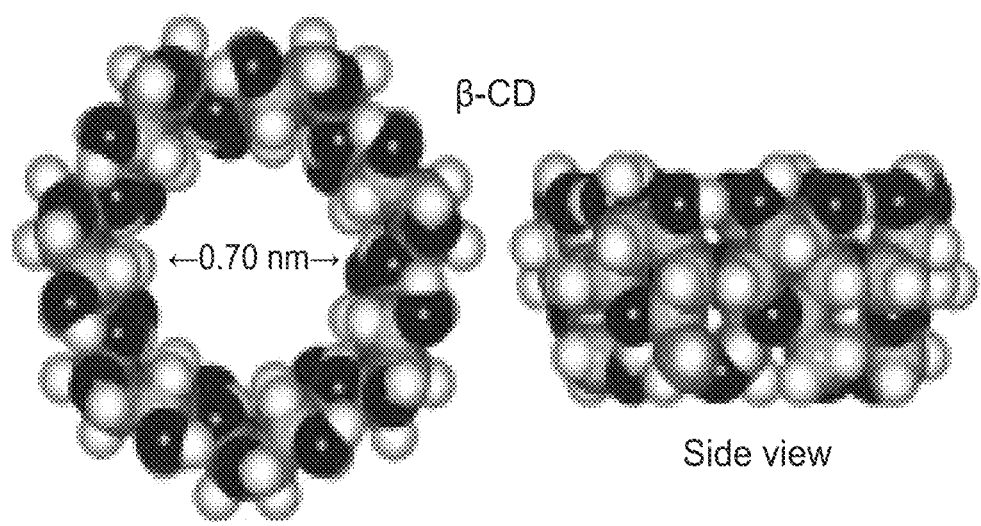
Figure 6D:
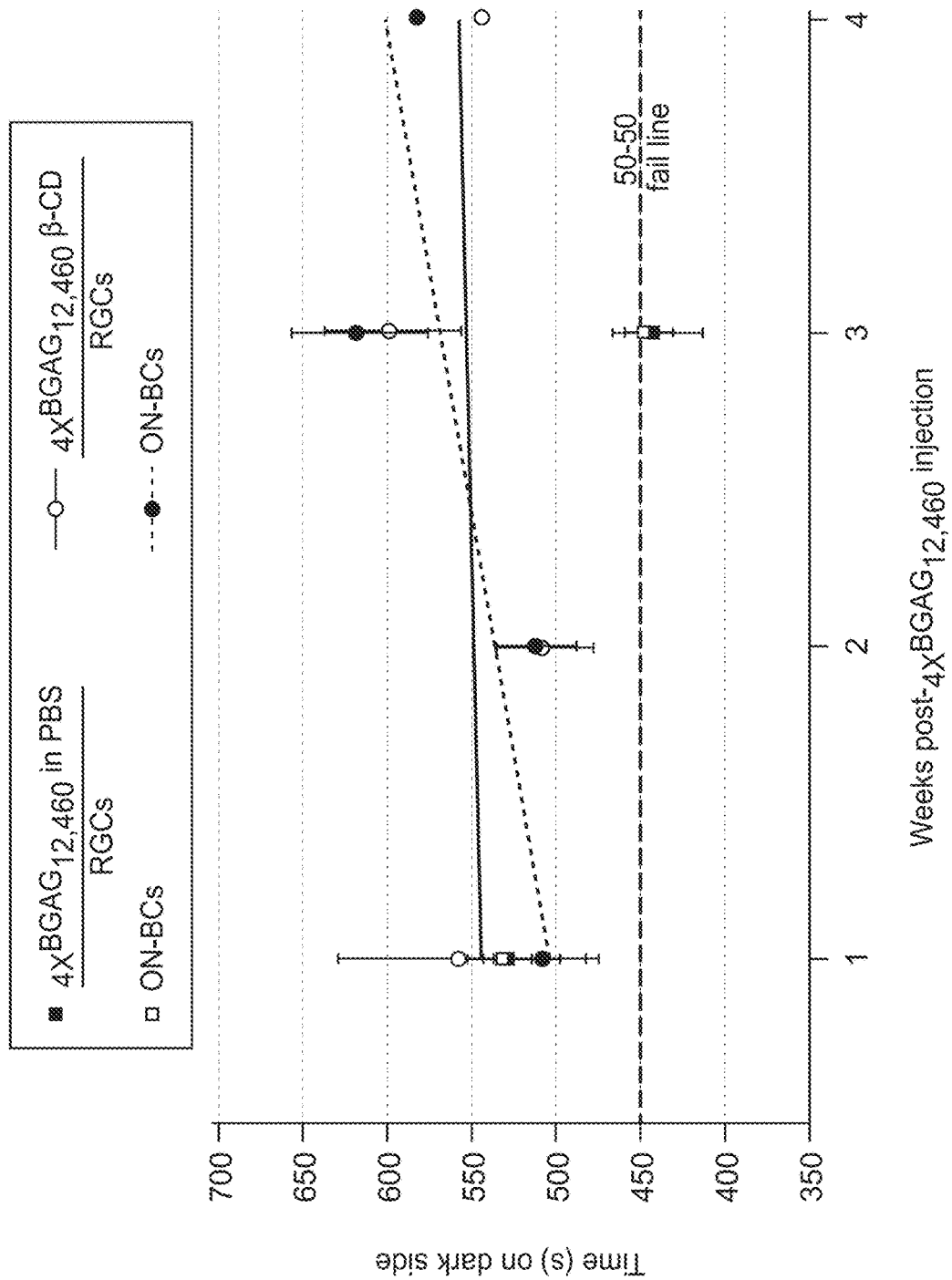
Figure 6E:
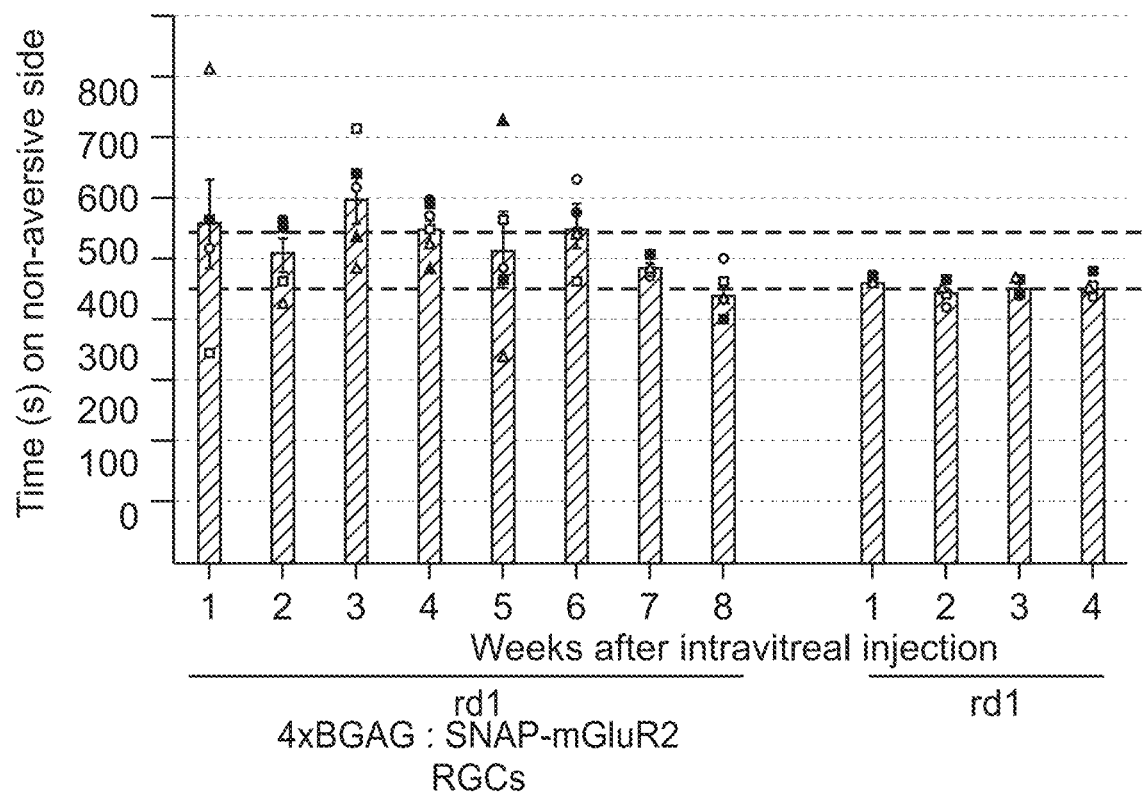
Figure 6F:
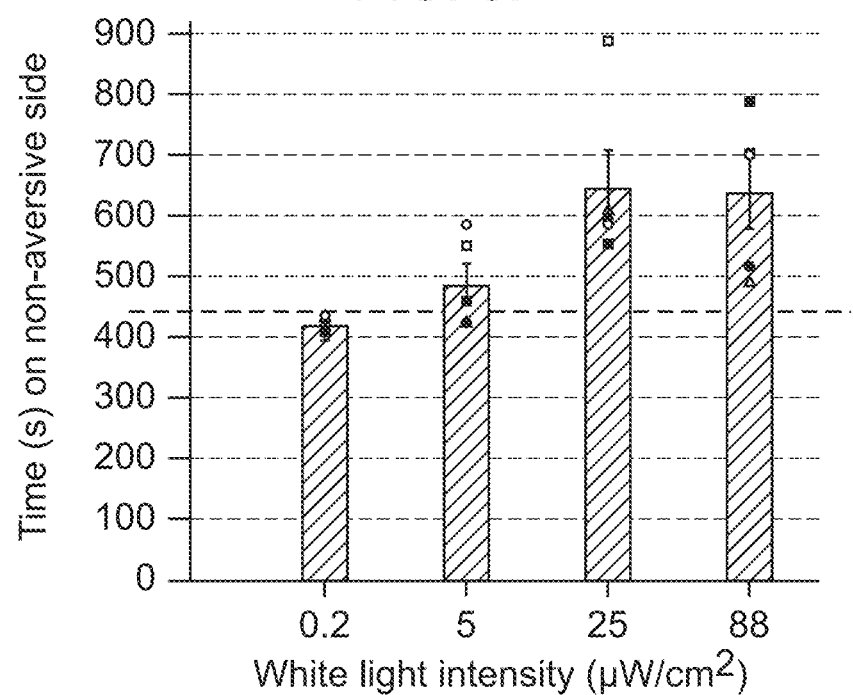

FIG. 6A-6F. $^{4\times}BGAG_{12,460}$:SNAP-mGluR2 in RGCs or ON-BCs RGCs restores light avoidance behavior in the rd1 mouse. FIGS. 6A and 6B. Cartoon of $^{4\times}BGAG_{12,460}$ (A) and molecular depiction of β-cyclodextrin (B). FIG. 6C. Light/dark 2-chamber shuttle box with two iPad mini displays, one illuminated white (88 μW/cm$^2$) and the other turned off. FIG. 6D. Untreated rd1 mice spend half of the 900 s observation period in the dark and half in the light compartments (violet dotted line), rd1 mice that had been injected intravitreally with AAV encoding hSyn-SNAP-mGluR2 for expression in RGCs (green and red) or 4×grm6-SNAP-mGluR for expression in ON-BCs (grey and blue) spend more time in the dark chamber 1 week after injection with $^{4\times}BGAG_{12,460}$ formulated in either PBS (green and grey) or β-cyclodextrin (red and blue). However, while effect wears off by 3 weeks with $^{4\times}BGAG_{12,460}$ formulated in PBS, it persists for 4 weeks when formulated in β-cyclodextrin. FIG. 6E. Untreated rd1 mice spend half of the 900 s observation period in the dark and half in the light compartments (lower red dashed line), rd1 mice that had been injected intravitreally with AAV encoding hSyn-SNAP-mGluR2 for expression in RGCs spend more time in the dark chamber (upper red dashed line) starting at 1 week after injection with $^{4\times}BGAG_{12,460}$ formulated in β-cyclodextrin and continuing through week 6. The effect declines and performance is the same as that of untreated rd1 mice by week 8. FIG. 6F. Light aversion analysis in the two-chamber Light/Dark box with different intensities of light provides an intensity-response relation. $^{4\times}BGAG_{12,460}$:SNAP-mGluR2 in RGCs supports a maximal light aversion response at 25 μW/cm$^2$ and has a half maximal response between 5 and 25 μW/cm$^2$, with 0.2 μW/cm$^2$ operating at chance.

4-Branched BGAG Restores High-Sensitivity Line Pattern Recognition

As shown above, $^{4\times}BGAG_{12,460}$:SNAP-mGluR2 in either RGCs or ON-BCs confers high sensitivity light perception. It was asked whether $^{4\times}BGAG_{12,460}$:SNAP-mGluR2 would support patterned vision. The ability of treated and untreated rd1 mice to discriminate between two different line patterns in a learned negative association task was tested. The task is carried out in a 2-chamber arena, where the floor in each chamber is conductive and can apply an independent aversive mild foot shock. Each chamber had an iPad mini at its far end, which displayed a unique line pattern, consisting of parallel vertical lines at one of two spacings (1 versus 6 cm) (FIG. 7B). The mouse was trained for two days, during which a mild foot shock was given in one of the chambers. The line pattern associated with the foot shock was assigned randomly initially but then kept consistent for that animal throughout the 2 days of training. On the third day, no foot shock was given, and only the displays were shown. The chambers were cleaned thoroughly before and after each training or test session to remove olfactory clues. The room was kept dark to avoid room reference visual cues. And the aversive and non-aversive cues were switched between the end of the second day of training and the test day to avoid location bias. Provided they have sufficient visual acuity to distinguish between the two line patterns, sighted animals avoid the side with the line pattern that had been previously associated with the foot shock, whereas untreated blind rd1 show a location bias that reduces their time on the side that had been aversive during training and on the test day displayed the non-aversive visual cue (Berry et al. (2017) supra; and Berry et al. (2019) *Nature Commun.* 10:1221).

Figure 7A:
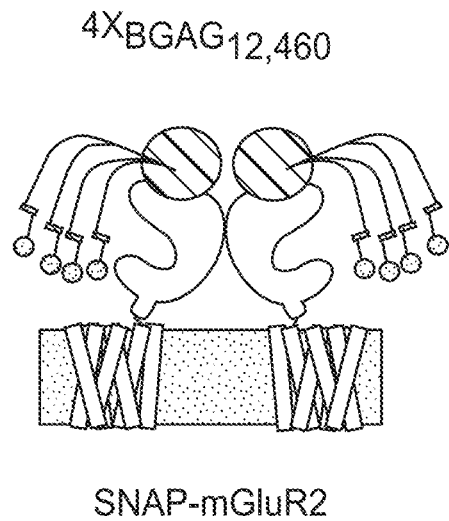
FIG. 7A-7C depict the effect of $^{4\times}BGAG_{12,460}$:SNAP-mGluR2 in RGCs or ON-BCs RGCs on learned spatial pattern recognition guided behavior in the rd1 mouse.
Figure 7B:
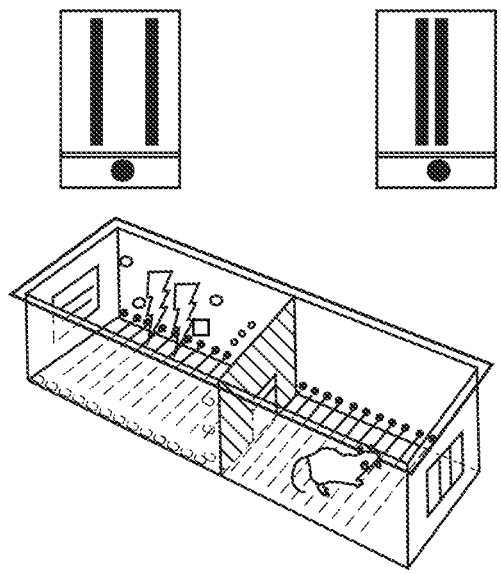
Figure 7C:
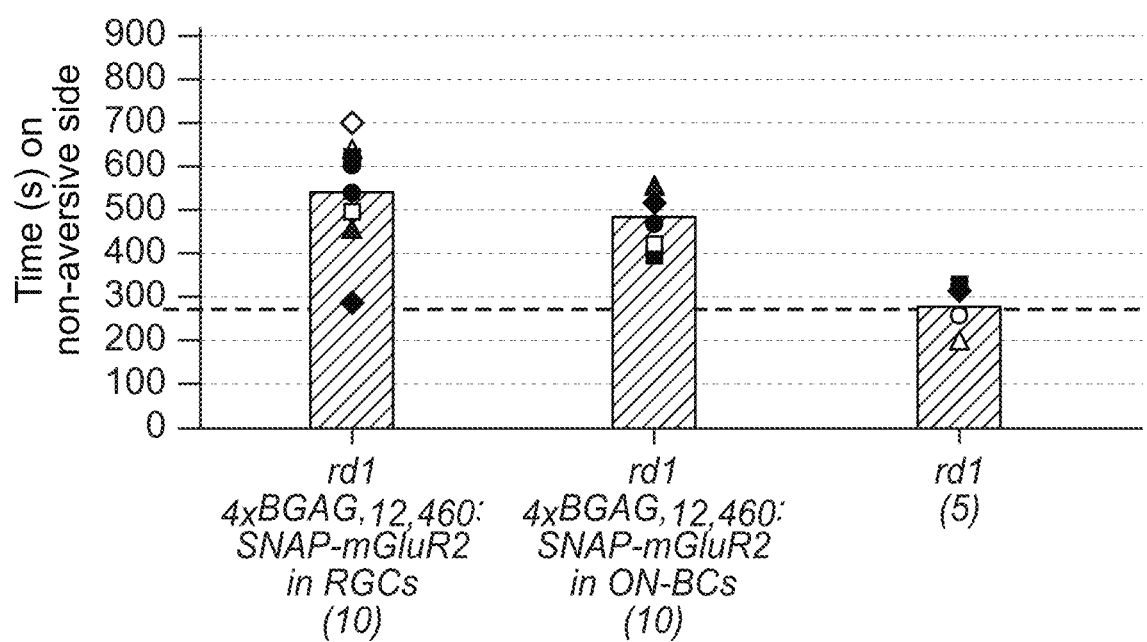
Figure 8A:
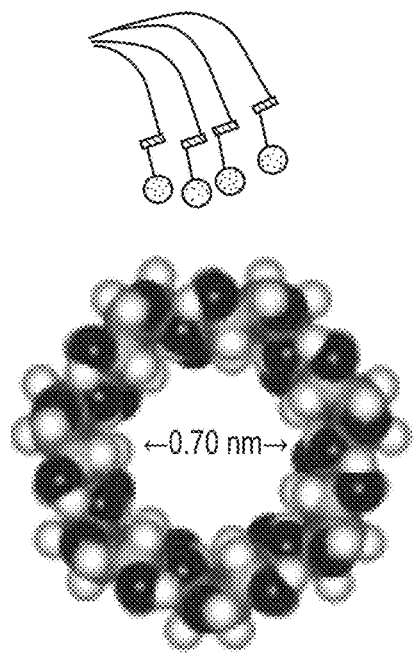
FIG. 8A-8C depict the effect of $^{4\times}BGAG_{12,460}$ in β-cyclodextrin on restoration of pattern recognition in a SNAP-mGluR2 rd1 mouse.
Figure 8B:
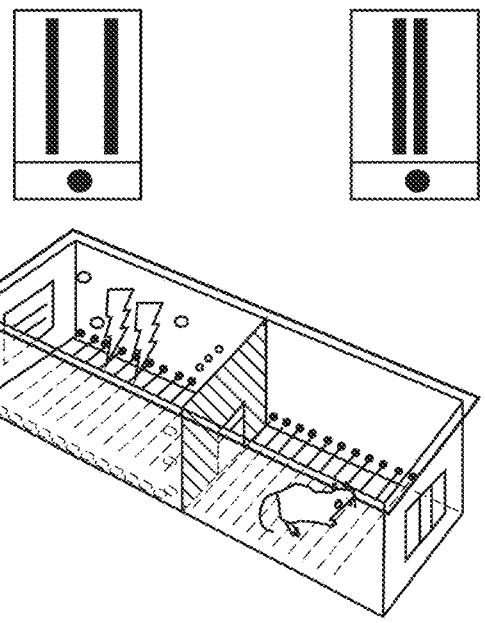
Figure 8C:
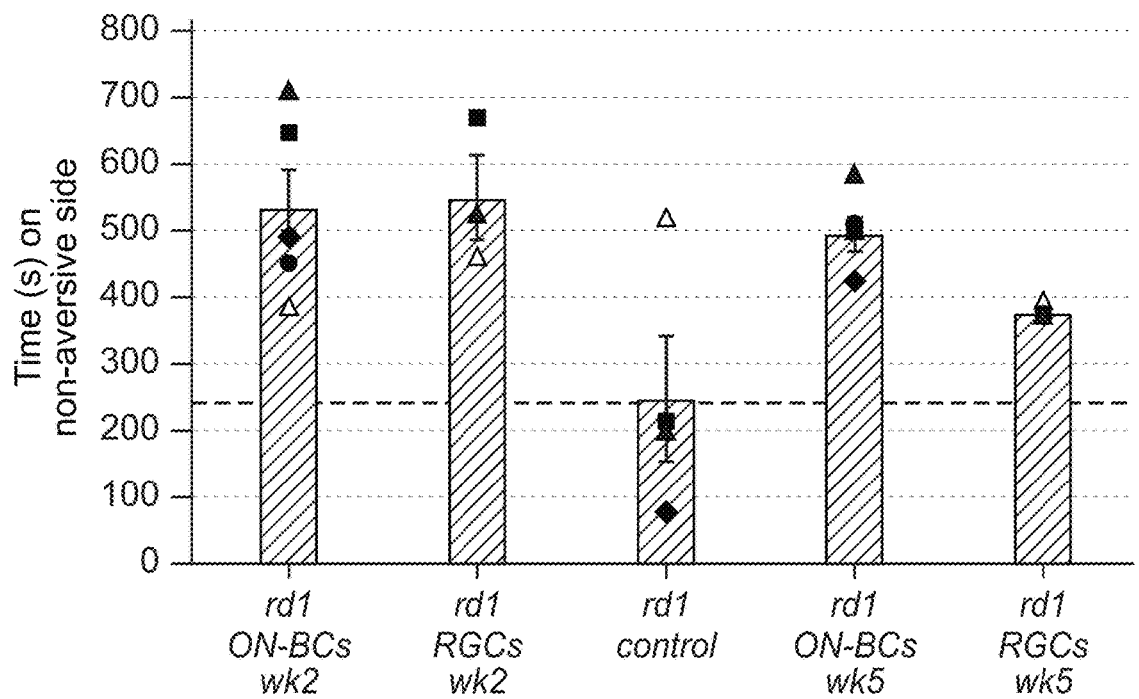

Rd1 mice expressing SNAP-mGluR2 in RGCs, which were trained and tested within a week after intravitreal injection with $^{4\times}BGAG_{12,460}$ in PBS, spent more time on the side of the non-aversive visual display (FIG. 7C). This behavior stood in stark contrast to that of untreated rd1 mice whose location bias had them favor the chamber that during the training period displayed the aversive cue, but during the test period displayed the non-aversive cue (FIG. 7C). Rd1 mice expressing SNAP-mGluR2 in ON-BCs and trained and tested within a week after intravitreal injection with $^{4\times}BGAG_{12,460}$ in PBS, spent also more time on the side of the non-aversive visual display to a similar (FIG. 7C). The strong preference for the chamber with the non-aversive-associated visual cues indicates that $^{4\times}BGAG_{12,460}$:SNAP-mGluR2 in either RGCs or ON-BCs restores spatial pattern recognition and provides sufficient acuity to distinguish a pair of parallel lines spaced 1 versus 6 cm apart. Restoration of the ability to distinguish between these two line patterns persisted for 5 weeks following intravitreal injection when $^{4\times}BGAG_{12,460}$ was formulated in β-cyclodextrin (FIG. 8A-8C).

Since formulation of $^{4\times}BGAG_{12,460}$ in β-cyclodextrin extended its restoration of light perception for several weeks (FIGS. 6D and 6E), it was asked whether β-cyclodextrin would also extend the duration of restoration of line pattern recognition. It was found that $^{4\times}BGAG_{12,460}$ in β-cyclodextrin restored the ability of rd1 mice with SNAP-mGluR2 in either ON-BCs or RGCs to distinguish between iPad displays showing a pair of lines separated by 1 and 6 cm for 5 weeks after intravitreal injection (FIG. 8A-8C). The efficacy at 5 weeks was unchanged compared to that at 2 weeks post-injection with SNAP-mGluR2 in ON-BCs but was reduced to ~ half in animals with SNAP-mGluR2 in RGCs.

To further assess the restored line pattern recognition, the lines were made thinner and the separation between the lines was reduced. Displays of 0.5 cm wide lines separated by either 0.25 or 0.5 cm were compared. In the two-chamber system, given the 18 cm distance from the point of decision to the iPad, the display with 0.5 cm thick lines separated by 0.5 cm is comparable to an optomotor drum spatial frequency of 0.2 cycles per degree, and is close to the acuity limit for wildtype mouse (Kretschmer et al., 2017). Mice were trained by pairing either the line pair separated by 0.25 or 0.5 cm with foot shock in untreated rd1 mice and rd1 mice expressing SNAP-mGluR2 in RGCs following intravitreal injection with $^{4\times}BGAG_{12,460}$ in PBS. $^{4\times}BGAG_{12,460}$ enabled the rd1 mice to perform the task and to do so as well as wildtype mice (FIG. 9).

FIG. 7A-7C. $^{4\times}BGAG_{12,460}$:SNAP-mGluR2 in RGCs or ON-BCs RGCs restores learned spatial pattern recognition guided behavior in the rd1 mouse. FIG. 7A. Cartoon of $^{4\times}BGAG_{12,460}$:SNAP-mGluR2. FIG. 7B. 2-chamber shuttle box configured for aversive associated conditioning using iPad mini displays with 2 parallel black vertical bars on a white background separated by 1 cm in one chamber and 6 cm in the other chamber. FIG. 7C. Untreated rd1 mice spend less than half of the 900 s observation time on the aversive side because of location bias against the other side that was aversive during the training period. Within a week of $^{4\times}BGAG_{12,460}$ injection, rd1 mice expressing SNAP-mGluR2 in RGCs or ON-BCs both show preference for the non-aversive line pattern display. 4×BGAG supports close line differentiation acuity task when SNAP-mGluR2 is expressed in either RGCs or in ON-BCs.

FIG. 8A-8C. FIG. 8A. $^{4\times}BGAG_{12,460}$ and β-cyclodextrin. FIG. 8B. 2-chamber shuttle box configured for aversive associated conditioning showing the visual cues displayed on iPads in each chamber: 1 cm wide black bars on a white background separated by 1 or 6 cm. FIG. 8C. $^{4\times}BGAG_{12,460}$ in β-cyclodextrin restores line pattern recognition (favoring chamber with non-aversive associated display) for 2 and 5 weeks after intravitreal injection in rd1 mice expressing SNAP-mGluR2 in either ON-BCs or RGCs compared to the untreated rd1 control.

Figure 9:
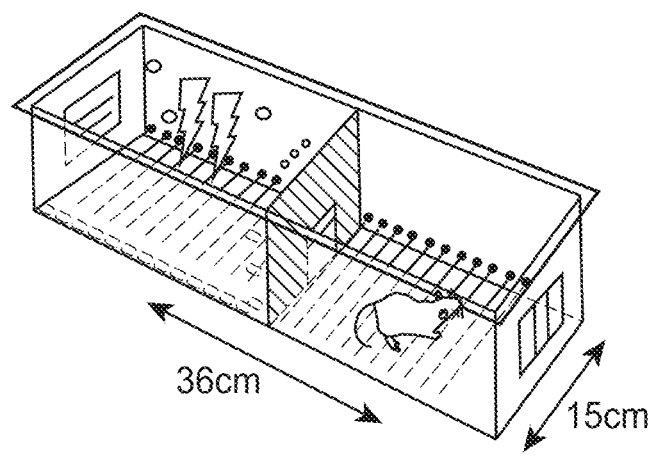
FIG. 9 depicts restoration of high-acuity line pattern recognition in an rd1 mouse following intravitreal injection of $^{4\times}BGAG_{12,460}$.
Figure 9:
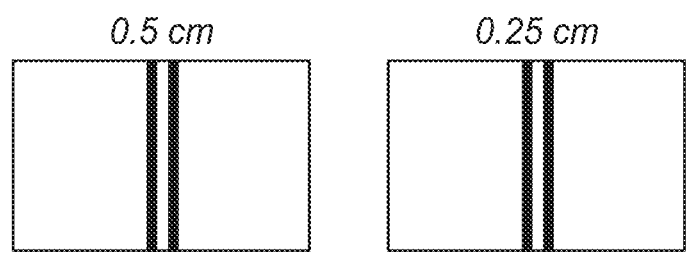
Figure 9:
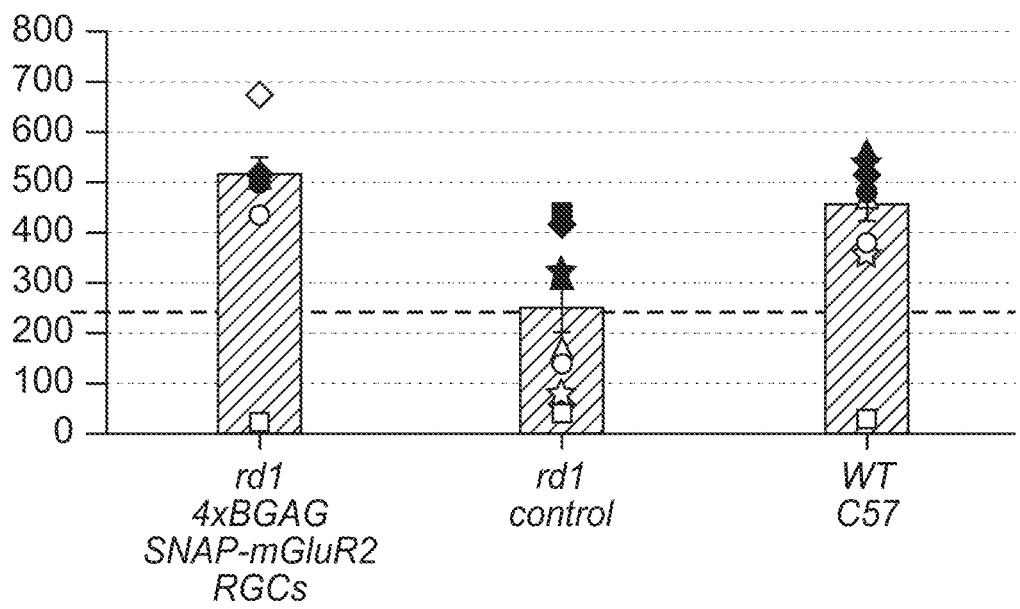

FIG. 9. $^{4\times}BGAG_{12,460}$ restores high-acuity line pattern recognition in RGCs of rd1 mouse. $^{4\times}BGAG_{12,460}$ in PBS following intravitreal injection in rd1 mice expressing SNAP-mGluR2 in RGCs restores line pattern recognition as well as with normal vision in C57 wildtype animals. The displays used 0.5 cm wide bars separated by either 0.25 or 0.5 cm, a spatial frequency approaching the resolution limit of normal mouse vision.

Branched BGAG Restores Line Pattern Recognition in a Moving Display

The kinetics of onset, decay and recovery of the restored light response are expected to affect the ability to recognize a visual pattern. Faster return to baseline upon termination of illumination and faster recovery of responsiveness to a subsequent light pulse have been proposed to explain why medium wave cone opsin in RGCs supports line pattern recognition in both stationary and moving visual displays, whereas rhodopsin, which is slower, does not, even then the display is stationary (Berry et al. (2019) supra). Since signaling and recovery with $BGAG_{12,460}$:SNAP-mGluR2 has a shorter delay in response to light and a faster return to baseline following termination of illumination than medium wave cone opsin (FIG. 10A-10C) (Berry et al. (2017) supra; (Berry et al. (2019) supra), the question was asked if $BGAG_{12,460}$:SNAP-mGluR2 would also support line pattern recognition at faster speeds of movement. This was tested in the line pattern differentiation task, with lines separated by 6 cm in one display and 1 cm in the other, as above (FIG. 8A-8C), except now with the lines in motion. It was found that rd1 animals with $^{4\times}BGAG_{12,460}$:SNAP-mGluR2 in RGCs performed as well as wildtype animals when the line displays moved at either 4 or 8 cm/s (FIG. 11). In contrast, rd1 animals expressing medium wave cone opsin in RGCs, which was shown to perform well when the displays move at 1 cm/s (Berry et al. (2019) supra), performed at the level of the untreated rd1 animals when the display moved at 4 cm/s (FIG. 11). Thus, the speed limit of $^{4\times}$BGAG$_{12,460}$:SNAP-mGluR2 in RGCs is ≥8 cm/s, whereas that of medium wave cone opsin in RGCs is ≤4 cm/s.

Figure 10A:
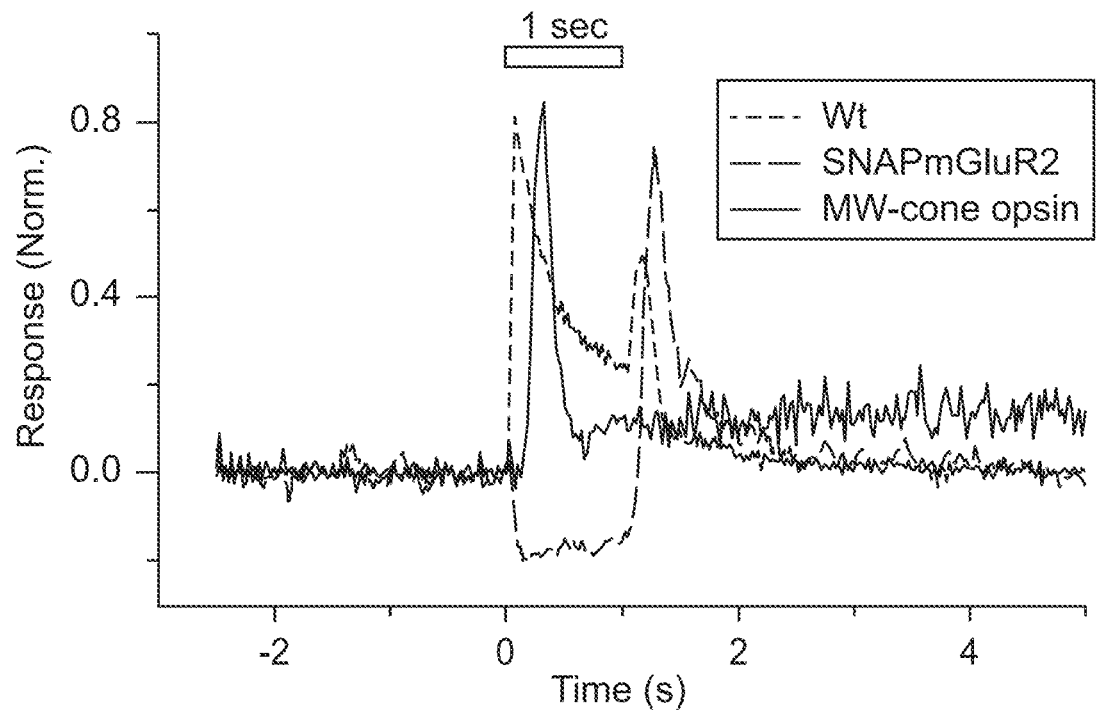
FIG. 10A-10C depict microelectrode array (MEA) recordings of RGCs from isolated rd1 retina with either $BGAG_{12,460}$:SNAP-mGluR2 or medium wave cone opsin (MW opsin) in RGCs.
Figure 10B:
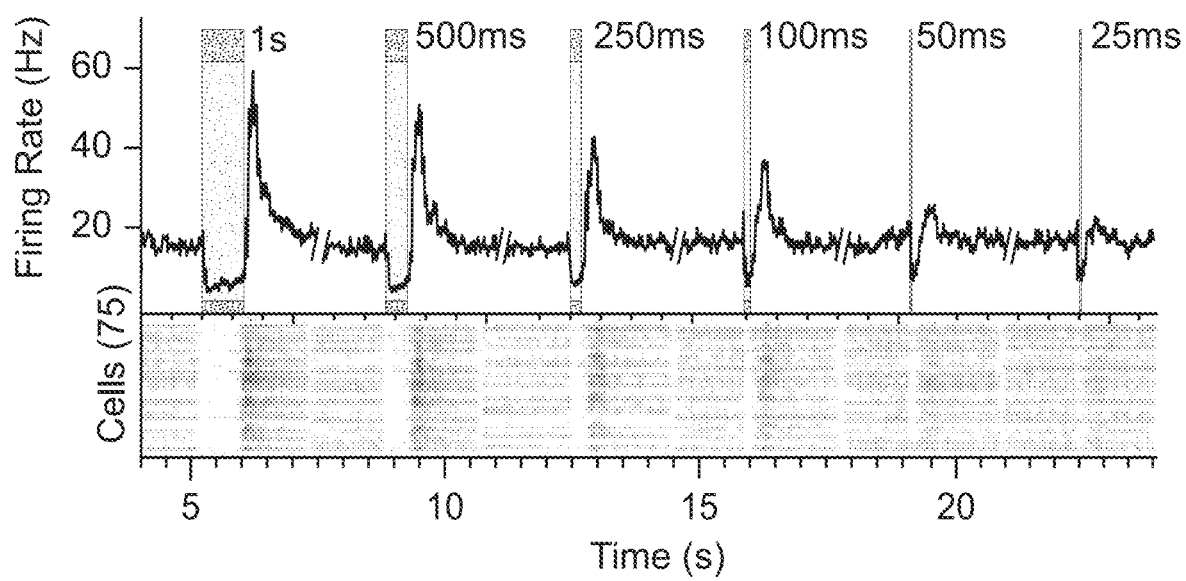
Figure 10C:
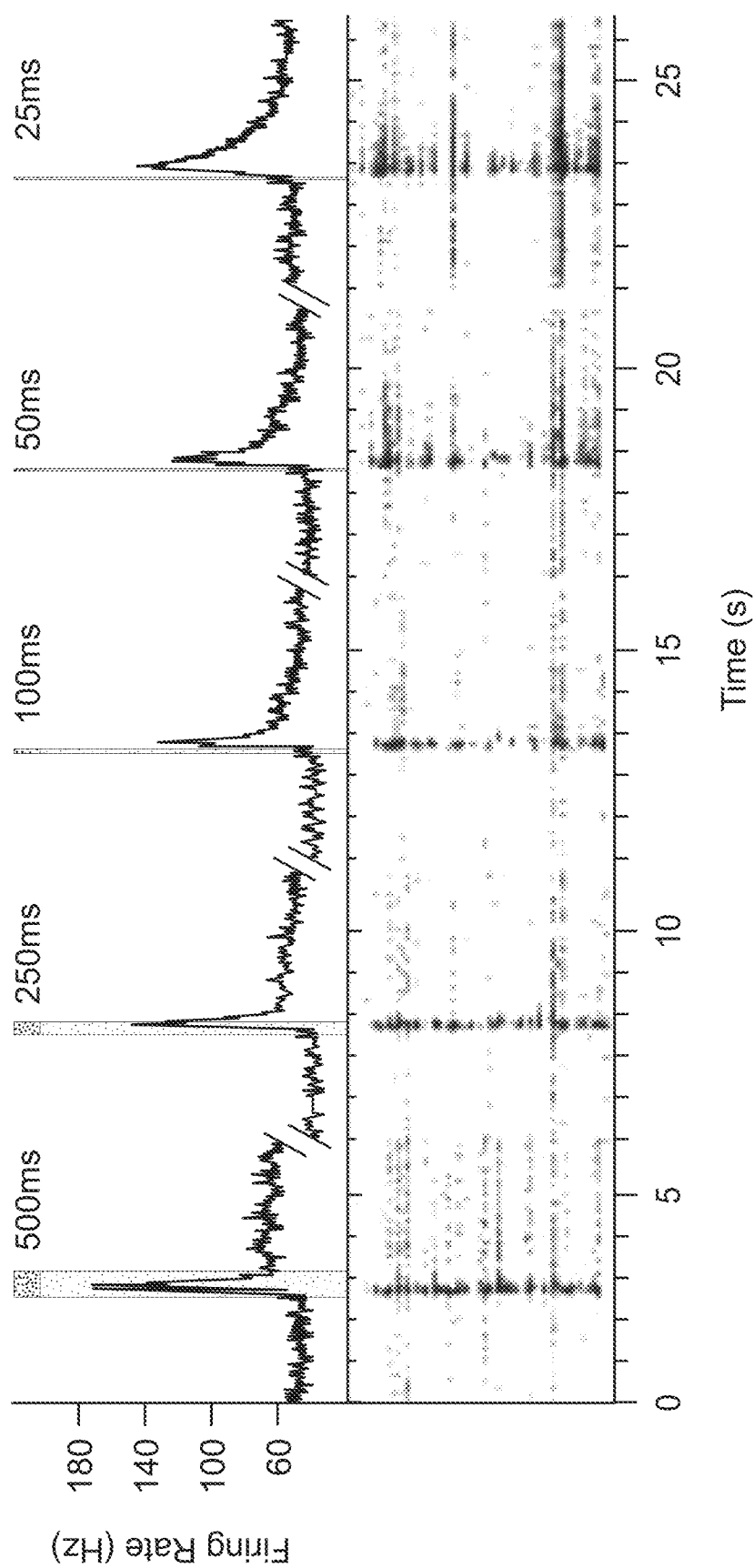
Figure 11:
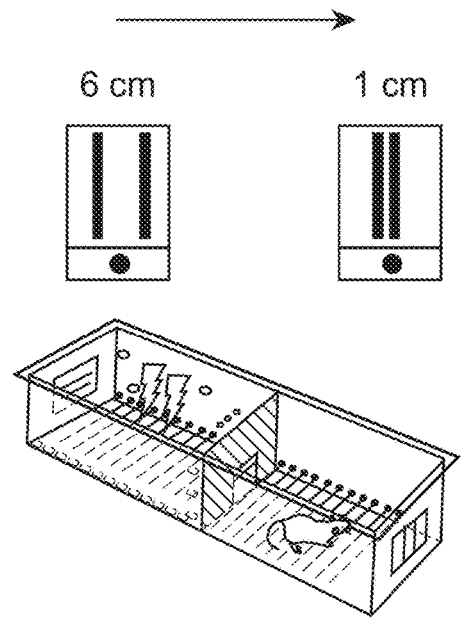
FIG. 11 depicts the effect of $^{4\times}BGAG_{12,460}$:SNAP-mGluR2 in RGCs of rd1 mice on restoration of line pattern recognition in moving displays, compared with MW opsin.
Figure 11:
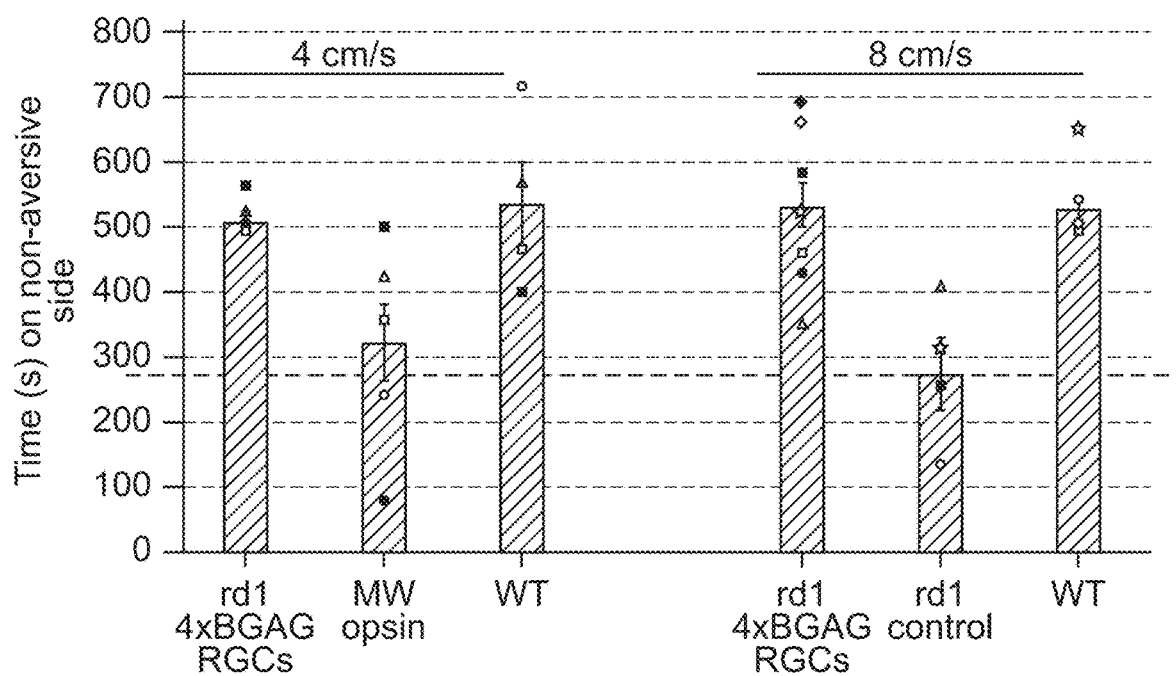

FIG. 10A-10C. MEA recordings of RGCs from isolated rd1 retina with either BGAG$_{12,460}$:SNAP-mGluR2 or medium wave cone opsin in RGCs. A) Superimposed average responses to 1 s light flashes in dozens of RGCs in 3 representative retinas isolated from: wildtype mice (Wt; red), rd1 mice expressing medium wave (MW) cone opsin in RGCs (black), and rd1 mice expressing SNAP-mGluR2 in RGCs (blue) following intravitreal injection of BGAG$_{12,460}$. Note short latency responses to light onset in Wt and BGAG$_{12,460}$:SNAP-mGluR2 compared to delayed response in MW-opsin. B) Blue light activation of BGAG$_{12,460}$:SNAP-mGluR2 evokes an immediate inhibition with a sustained amplitude during illumination, followed by a transient excitatory rebound after termination of illumination. As light pulses are shortened (number of photons decreased) the inhibition and rebound excitation diminish in amplitude but do not change kinetics, maintaining the short latency and fast activation and deactivation, (from (Berry et al. (2017) supra). C) Green light activation of medium wave cone opsin evokes a transient excitation after a delay. As light pulses are shortened, the delay to peak response increases and deactivation slows, (from (Berry et al. (2019) supra).

FIG. 11. $^{4\times}$BGAG$_{12,460}$:SNAP-mGluR2 in RGCs of rd1 mouse restores line pattern recognition in moving displays. 2-chamber shuttle box configured for aversive associated conditioning showing the visual cues displayed on iPads in each chamber: 1 cm wide black bars on a white background separated by 1 or 6 cm moving left to right at 4 cm/s or 8 cm/s.

$^{4\times}$BGAG$_{12,460}$:SNAP-mGluR2 Restores Novel Object Exploration

Figure 12:
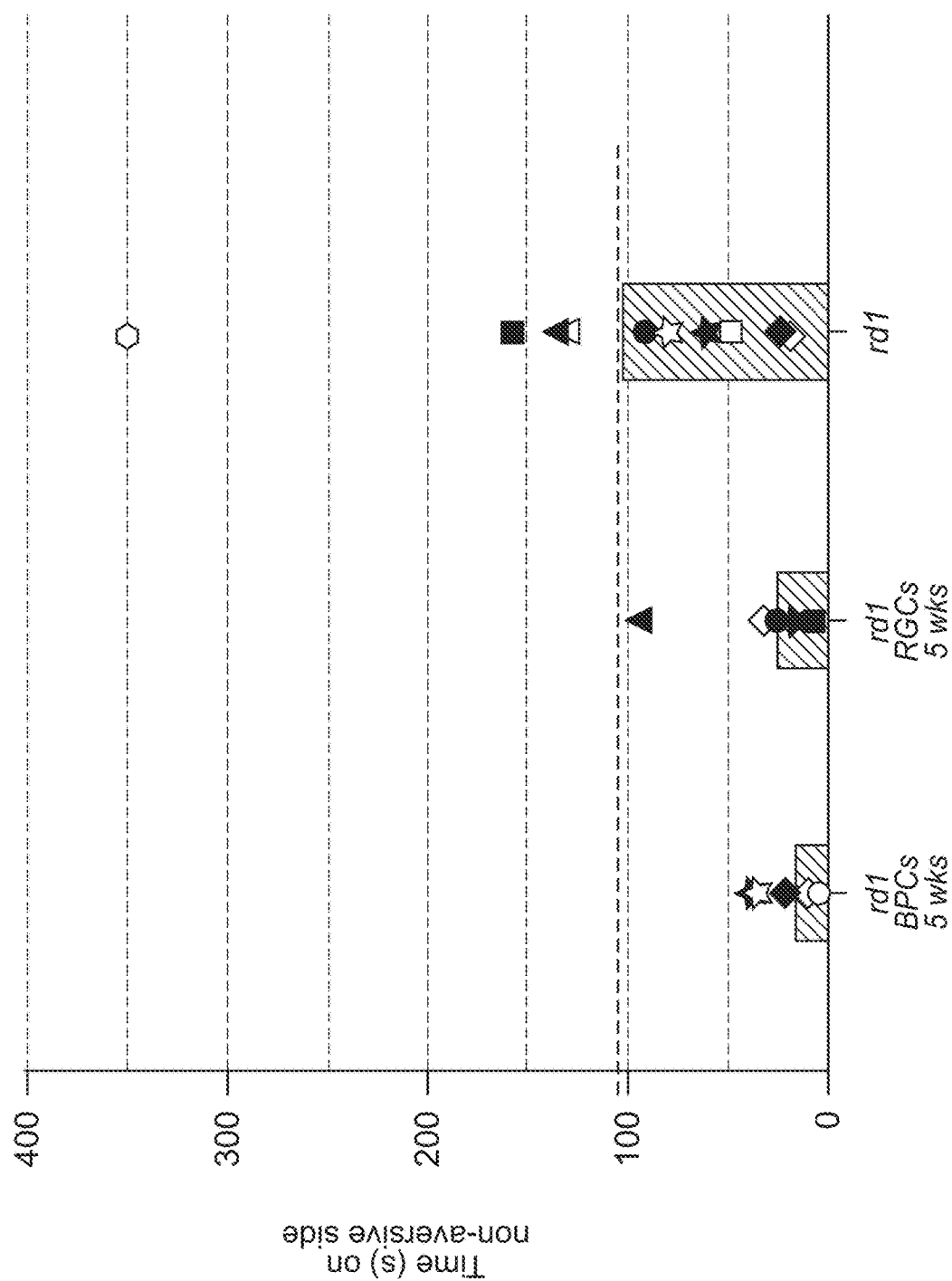
FIG. 12 depicts the effect of $^{4\times}BGAG_{12,460}$:SNAP-mGluR2 in RGCs or ON-BCs of rd1 mice on novel object recognition.

The experiments above showed that $^{4\times}$BGAG$_{12,460}$:SNAP-mGluR2 enables pattern recognition using computer displays. It was asked whether $^{4\times}$BGAG$_{12,460}$:SNAP-mGluR2 would operate in a natural environment, where ambient, incidental light illuminates three-dimensional objects. To address this, an open field arena that is commonly used to test novel object recognition and exploratory behavior was employed. Mice naturally avoid open spaces and maintain proximity to walls of their environment. Exploratory excursions from these places of safety can be motivated by novel stimuli. Although mice employ multiple sensory modalities during exploration, vision has been shown to be critical for spatial navigation. The arena consisted of a cube containing two distinct novel objects. The mouse was placed against the arena wall, far enough from the objects, which themselves were far enough apart, so that the chance of an accidental encounter was low whether the animal walked along the wall or explored the other object. Untreated rd1 mice, and rd1 mice expressing $^{4\times}$BGAG$_{12,460}$:SNAP-mGluR2 in either RGCs or ON-BCs, were filmed. Their movements were tracked for 10 minutes the first time that they were placed into the arena. The aspect of exploratory behavior that most likely depends on vision at a distance, i.e., the latency to exploration of the novel objects, was assessed. Untreated rd1 mice had long latencies to the first object, and often appeared to encounter the object accidentally when turning around. The data are shown in FIG. 12. Rd1 mice with SNAP-mGluR2 in either RGCs or ON-BCs had shorter latencies 5 weeks after intravitreal injection of $^{4\times}$BGAG$_{12,460}$ in β-cyclodextrin. These results suggest that $^{4\times}$BGAG$_{12,460}$:SNAP-mGluR2 in either ON-BCs or RGCs provides previously blind animals with naturalistic vision of objects under ambient light.

FIG. 12. $^{4\times}$BGAG$_{12,460}$:SNAP-mGluR2 in RGCs or ON-BCs of rd1 mouse support novel object recognition. Open field behavioral arena contained two novel objects. Mice were tracked to measure the speed of locomotion and latency to exploration of the objects. Latency to exploration of the first object in untreated rd1 mice and in rd1 mice expressing SNAP-mGluR2 in either ON-BCs or RGCs 5 weeks after intravitreal injection of $^{4\times}$BGAG$_{12,460}$ in β-cyclodextrin.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition for intraocular administration, the composition comprising:
   A) a conjugate comprising:
      a) an affinity agent that specifically binds:
         i) a target ligand-binding polypeptide; or
         ii) a polypeptide that binds to a target ligand-binding polypeptide;
      b) a branched linker; and
      c) two or more photoisomerizable regulators, each independently comprising:
         i) an azobenzene 460 photoisomerizable group; and
         ii) a ligand that binds to the target ligand-binding polypeptide; and
   B) a pharmaceutically acceptable excipient suitable for intraocular administration.

2. The composition of claim 1, wherein the affinity agent comprises benzylguanine, chloroalkane, or benzylcytosine.

3. The composition of claim 1, wherein the affinity agent comprises an antibody.

4. The composition of claim 3, wherein the antibody is a single-chain Fv (scFv) or a nanobody.

5. The composition of claim 4, wherein the antibody is specific for a metabotropic glutamate receptor (mGluR), optionally wherein the mGluR is mGluR2, mGluR3, mGluR4, mGluR5, or mGluR6.

6. The composition of claim 1, wherein the affinity agent comprises an aptamer, a small molecule, or a peptide.

7. The composition of claim 1, wherein the branched linker comprises two or more arms, each independently comprising a photoisomerizable regulator.

8. The composition of claim 7, wherein the branched linker comprises two arms or four arms.

9. The composition of claim 1, wherein the branched linker comprises a moiety of formula (BL):

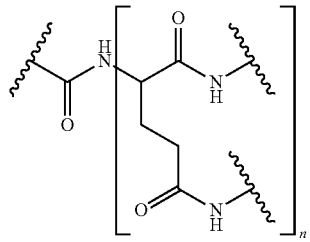

wherein n is an integer from 1 to 10.

10. The composition of claim 9, wherein n is 1 or 3.

11. The composition of claim 1, wherein the ligand is an agonist, an antagonist, an allosteric modulator, or a blocker.

12. The composition of claim 1, wherein the target ligand-binding polypeptide is selected from a transcription regulator, an ion channel, a cation channel, a ligand-gated ion channel, a voltage-gated ion channel, a quorum sensor, a pheromone receptor, a neurotransmitter receptor, a G-protein-coupled receptor, and an enzyme.

13. The composition of claim 1, wherein the target ligand-binding polypeptide is a glutamate receptor, a metabotropic glutamate receptor, an ionotropic glutamate receptor, an ionotropic nicotinic acetylcholine receptor, an ionotropic GABA-A receptor, a metabotropic GABA-B receptor, a metabotropic dopamine receptor, an ionotropic purinergic P2X receptor, a metabotropic purinergic P2Y receptor, a metabotropic serotonin receptor, an ionotropic serotonin receptor, an ionotropic glycine receptor, a cation channel, a potassium channel, a calcium channel, a sodium channel, a proton channel, an anion channel, or a chloride channel.

14. The composition of claim 1, wherein the ligand is glutamate.

15. The composition of claim 1, wherein the composition is sterile and free of pyrogens.

16. The composition of claim 1, wherein the pharmaceutically acceptable excipient comprises a cyclodextrin.

17. The composition of claim 16, wherein the cyclodextrin is α-cyclodextrin, β-cyclodextrin, γ-cyclodextrin, hydroxypropyl-β-cyclodextrin, sulfobutylether-β-cyclodextrin, methylated cyclodextrin, CRYSMEB, RAMEB, TRIMEB, or maltosyl-β-cyclodextrin.

18. The composition of claim 1, wherein the conjugate is encapsulated within a nanoparticle.

19. A composition for intraocular administration, the composition comprising:
A) a system comprising:
a) a conjugate of claim 1;
b) a fusion polypeptide comprising:
i) a target ligand-binding polypeptide that comprises a binding site for the ligand present in the conjugate; and
ii) a heterologous fusion partner that binds the affinity agent; and
B) a pharmaceutically acceptable excipient suitable for intraocular administration.

20. The composition of claim 19, wherein the heterologous fusion partner comprises:
a) an amino acid sequence having at least 80% amino acid sequence identity to the SNAP polypeptide amino acid sequence set forth in SEQ ID NO:1 or SEQ ID NO:4; or
b) an amino acid sequence having at least 80% amino acid sequence identity to the CLIP polypeptide amino acid sequence set forth in SEQ ID NO:2; or
c) an amino acid sequence having at least 80% amino acid sequence identity to the HALO polypeptide amino acid sequence set forth in SEQ ID NO:3.

21. A composition for intraocular administration, the composition comprising:
A) a system comprising:
a) a conjugate of claim 1;
b) nucleic acid comprising a nucleotide sequence encoding a fusion polypeptide comprising:
i) a target ligand-binding polypeptide that comprises a binding site for the ligand; and
ii) a heterologous fusion partner that binds the affinity agent; and
B) a pharmaceutically acceptable excipient suitable for intraocular administration.

22. The composition of claim 21, wherein the heterologous fusion partner comprises:
a) an amino acid sequence having at least 80% amino acid sequence identity to the SNAP polypeptide amino acid sequence set forth in SEQ ID NO:1 or SEQ ID NO:4;
b) an amino acid sequence having at least 80% amino acid sequence identity to the HALO polypeptide amino acid sequence set forth in SEQ ID NO:3; or
c) an amino acid sequence having at least 80% amino acid sequence identity to the CLIP polypeptide amino acid sequence set forth in SEQ ID NO:2.

23. The composition of claim 21, wherein the nucleic acid is present in a recombinant adenovirus-associated virus (AAV) virion.

24. The composition of claim 23, wherein the AAV virion comprises a variant capsid polypeptide that provides for increased infectivity of a retinal cell by the AAV virion, compared to an AAV virion comprising a corresponding wild-type capsid polypeptide.

25. A composition for intraocular administration, the composition comprising:
A) a system comprising:
a) a conjugate of claim 1;
b) a first fusion polypeptide comprising:
i) a target ligand-binding polypeptide that comprises a binding site for the ligand; and
ii) a heterologous polypeptide; and
c) a second fusion polypeptide comprising:
i) an antibody that binds the heterologous polypeptide; and
ii) a heterologous fusion partner that binds the affinity agent; and
B) a pharmaceutically acceptable excipient suitable for intraocular administration.

26. A composition for intraocular administration, the composition comprising:
A) a system comprising:
a) a conjugate of claim 1;
b) a fusion polypeptide comprising:
i) an antibody that binds specifically to the target ligand-binding polypeptide; and
ii) a polypeptide that binds to the affinity agent, wherein the polypeptide is selected from a SNAP polypeptide, a HALO polypeptide, and a CLIP polypeptide; and
B) a pharmaceutically acceptable excipient suitable for intraocular administration.

27. A method of increasing the sensitivity of a retinal cell to light, the method comprising:
exposing the retinal cell to light, wherein the retinal cell comprises a conjugate of claim 1, wherein the light is of a wavelength that results in binding of the ligand to the light-regulatable polypeptide, and wherein binding of the ligand to the light-regulatable polypeptide increases the sensitivity of the retinal cell to light.

28. A method of conferring light responsiveness on a retinal cell, the method comprising introducing into the retinal cell a conjugate of claim 1.

29. A method of treating an ocular disorder characterized by reduced responsiveness to light, the method comprising administering a composition according to claim 1 to an eye of an individual having the ocular disorder.

30. A medical device comprising:
a) a container comprising a composition according to claim 1; and
b) a means for introducing the composition into the eye of an individual.

* * * * *